(12) United States Patent
Tian et al.

(10) Patent No.: US 9,181,375 B2
(45) Date of Patent: Nov. 10, 2015

(54) FLUORESCENT POTASSIUM ION SENSORS

(75) Inventors: Yanqing Tian, Tempe, AZ (US);
Deirdre Meldrum, Phoenix, AZ (US);
Xianfeng Zhou, Tempe, AZ (US);
Fengyu Su, Tempe, AZ (US); Roger H. Johnson, Phoenix, AZ (US); Cody Youngbull, Tempe, AZ (US)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 90 days.

(21) Appl. No.: 13/985,260

(22) PCT Filed: Feb. 13, 2012

(86) PCT No.: PCT/US2012/024856
§ 371 (c)(1),
(2), (4) Date: Mar. 26, 2014

(87) PCT Pub. No.: WO2012/112440
PCT Pub. Date: Aug. 23, 2012

(65) Prior Publication Data
US 2014/0200319 A1 Jul. 17, 2014

Related U.S. Application Data

(60) Provisional application No. 61/442,518, filed on Feb. 14, 2011.

(51) Int. Cl.
| | |
|---|---|
| *C08F 226/06* | (2006.01) |
| *C07D 498/08* | (2006.01) |
| *C07D 519/00* | (2006.01) |
| *G01N 33/84* | (2006.01) |
| *C07F 15/00* | (2006.01) |
| *C08F 230/04* | (2006.01) |

(52) U.S. Cl.
CPC ............ *C08F 226/06* (2013.01); *C07D 498/08* (2013.01); *C07D 519/00* (2013.01); *C07F 15/0093* (2013.01); *C08F 230/04* (2013.01); *G01N 33/84* (2013.01); *C08G 2261/226* (2013.01); *C08G 2261/3223* (2013.01)

(58) Field of Classification Search
CPC .................................................... C08F 226/06
USPC ........................................................ 526/241
See application file for complete search history.

(56) References Cited

U.S. PATENT DOCUMENTS

| | | | |
|---|---|---|---|
| 5,641,684 | A | 6/1997 | Moore et al. |
| 6,211,359 | B1 | 4/2001 | He et al. |
| 6,399,392 | B1 | 6/2002 | Haugland et al. |
| 7,208,121 | B2 | 4/2007 | Peper et al. |
| 7,226,563 | B2 | 6/2007 | Bakker et al. |
| 7,390,462 | B2 | 6/2008 | Rao et al. |
| 2004/0180391 | A1 | 9/2004 | Gratzl et al. |
| 2007/0259443 | A1 | 11/2007 | He et al. |

FOREIGN PATENT DOCUMENTS

| | | |
|---|---|---|
| WO | WO 0200196 | 1/2002 |
| WO | WO 2007006454 | 1/2007 |
| WO | WO 2007044866 | 4/2007 |
| WO | WO 2007131042 | 11/2007 |

OTHER PUBLICATIONS

Blom et al., Preparative LC-MS purification: improved compound specific method optimization, Journal of Combinatorial Chemistry, 2004, vol. 6, No. 6, 874-883.
Carpenter et al., Synthesis of a sensitive and selective potassium-sensing fluoroionophore, Org Lett., Mar. 19, 2010, vol. 12, No. 6, pp. 1160-1163.
Carpenter et al., Function-oriented synthesis of a didesmethyl triazacryptand and analogue for fluorescent potassium ion sensing, European Journal of Organic Chemistry, Mar. 2011, vol. 2011, No. 7, pp. 1242-1248.
Gopalan et al., Star-shaped azo-based dipolar chromophores: design, synthesis, matrix compatibility, and electro-optic activity, Journal of the American Chemical Society, 2004, vol. 126, pp. 1741-1747.
He et al., A fluorescent sensor with high selectivity and sensitivity for potassium in water, Journal of the American Chemical Society, 2003, vol. 125, pp. 1468-1469.
Konstantinova et al., Synthesis and properties of some fluorescent 1,8-Naphthalimide derivatives and their copolymers with methyl methacrylate, Journal of Applied Polymer Science, 2009, vol. 111, pp. 1991-1998.
Magzoub et al., Millisecond Association Kinetics of K+ with triazacryptand-based K+ indicators measured by fluorescence correlation spectroscopy, Journal of Physical Chemistry B, 2006, vol. 110, pp. 21216-21221.
Namkung et al., Cell-based fluorescence screen for K+ channels and transporters using an extracellular triazacryptand-based K+ sensor, Journal of the American Chemical Society, 2008, vol. 130, No. 25, pp. 7794-7795.
Padmawar et al., K+ waves in brain cortex visualized using a long wavelength K+-sensing fluorescent indicator, Nature Methods, 2005, vol. 2, No. 11, pp. 825-827.
Stoll et al., A new fluorescent calix crown ether: synthesis and complex formation with alkali metal ions, Chemistry: A European Journal, 2008, vol. 14, No. 4, pp. 1155-1163.

(Continued)

*Primary Examiner* — Taofiq A Solola
(74) *Attorney, Agent, or Firm* — Fish & Richardson P.C.

(57) ABSTRACT

This disclosure relates generally to potassium ion sensors and monomers derived from such sensors. The disclosure also provides for polymers (e.g., random copolymers, nanoparticles, polymer thin films, and sensors) having polymerized monomeric potassium ion sensors as described herein. These compounds and polymers are useful for measuring intracellular and extracellular potassium ion concentrations.

4 Claims, 24 Drawing Sheets

(56) References Cited

OTHER PUBLICATIONS

Tian et al., A new crosslinkable oxygen sensor covalently bonded into poly (2-hydroxyethyl methacrylate)-CO-Polyacrylamide thin film for dissolved oxygen sensing, Chemistry of Materials, 2010, vol. 22, No. 6, pp. 2069-2078.

Tian et al., A series of naphthalimide derivatives as intra- and extracellular pH sensors, Biomaterials, 2010, vol. 31, No. 29, pp. 7411-7422.

Tusa et al., Critical care analyzer with fluorescent optical chemosensors for blood analytes, Journal of Materials Chemistry, 2005, vol. 15, No. 27-28, pp. 2640-2647.

Authorized Officer Kim Mi Hwa, International Search Report and Written Opinion for International Application No. PCT/US2012/024856, mailed Sep. 26, 2012, 11 pages.

Authorized Officer Mineko Mohri, International Preliminary Report on Patentability for International Application No. PCT/US2012/024856, mailed Aug. 29, 2013, 7 pages.

SM3

FLUORESCENT POTASSIUM ION SENSORS

CROSS-REFERENCE TO RELATED APPLICATIONS

This application is the U.S. National Stage under 35 U.S.C. 371 of International Application No. PCT/US2012/024856, filed on Feb. 13, 2012, which claims priority to U.S. Provisional Application Ser. No. 61/442,518, filed on Feb. 14, 2011. The entire contents of the foregoing are incorporated by reference herein.

GRANT INFORMATION

This invention was made with government support under 5P50 HG002360 awarded by the National Institute of Health. The government has certain rights in the invention.

TECHNICAL FIELD

This disclosure relates generally to potassium ion sensors and monomers derived from such sensors. The disclosure also provides for polymers (e.g., random copolymers, nanoparticles, polymer thin films) and sensing films comprising polymerized monomeric potassium ion sensors. These compounds and polymers are useful for measuring intracellular and extracellular potassium ion concentrations.

BACKGROUND

The accurate measurement of potassium ion ($K^+$) levels in biological samples, in vivo, in vitro, extracellular or intracellular, is essential, given the impact ion levels have on many aspects of homeostasis. Normal levels of potassium are important for the maintenance of heart, and nervous system function. Potassium ion levels that differ from a normal baseline can be associated with various disease states. For example, high levels of potassium are associated with hyperkalemia, kidney damage and diabetes, adrenal dysfunction, and trauma. Low levels of potassium, on the other hand, are associated with hypokalemia, myalgia and muscular weakness, skin related problems, and heart related problems. Traditionally, potassium ions have been measured in plasma or serum using ion-selective electrodes, which are cumbersome to use and costly to maintain. There is a need for the development of alternative methods of measuring potassium ion concentration in a variety of sample mediums.

SUMMARY

This disclosure provides new potassium ion sensors which are suitable for both intracellular and extracellular sensing. For extracellular sensing, for example, sensors were prepared having a double bond functional moiety, enabling the polymerization of the sensors with other commercially available monomers to create a polymeric sensor polymer, nanoparticle, or sensing film. In addition, the potassium ion sensors provided herein show high selectivity to sodium ion. For example, the sensors exhibit no affect in performance in the presence of up to about 150 mM of sodium ions. Further provided herein are dual sensors for multi-biological parameters measurements. For example, a potassium ion and dissolved oxygen dual sensor.

Provided herein is a compound of formula (1):

or a salt form thereof, wherein: m is 0 or 1; n is an integer from 0 to 3; and X is selected from the group consisting of:

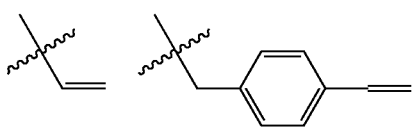

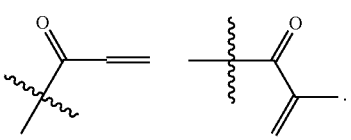

Non-limiting examples of a compound of formula (1) include:
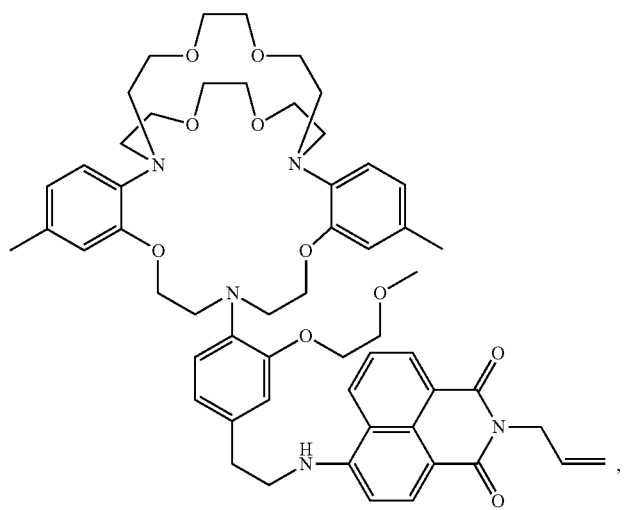
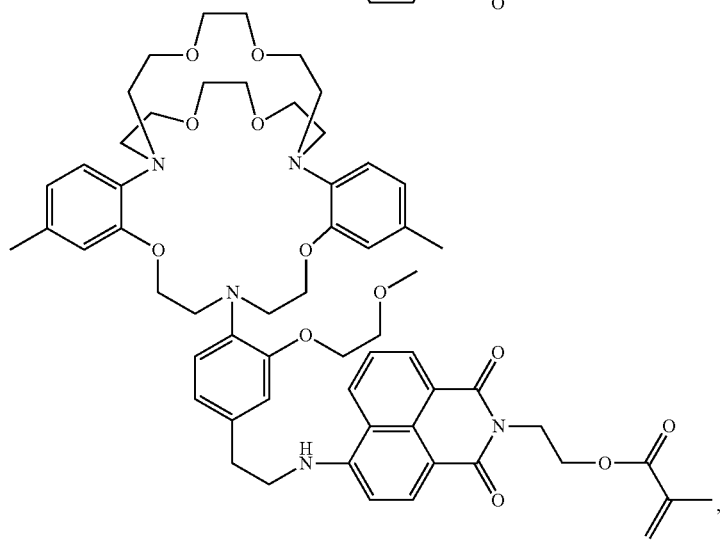
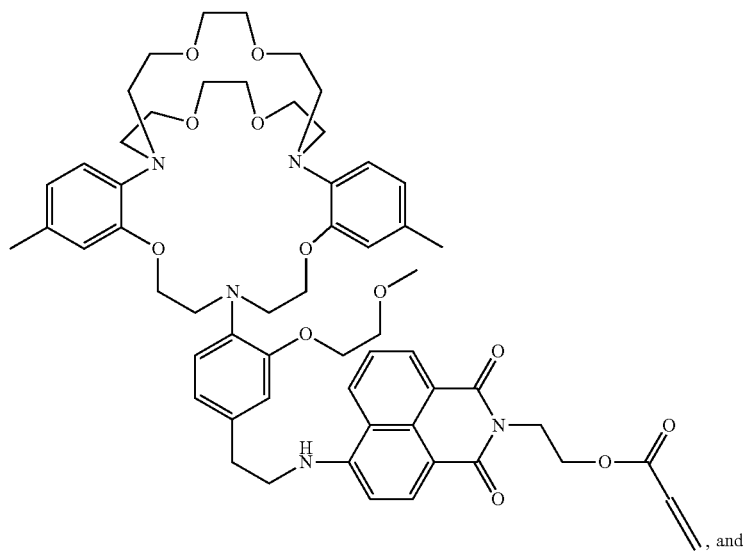
, and

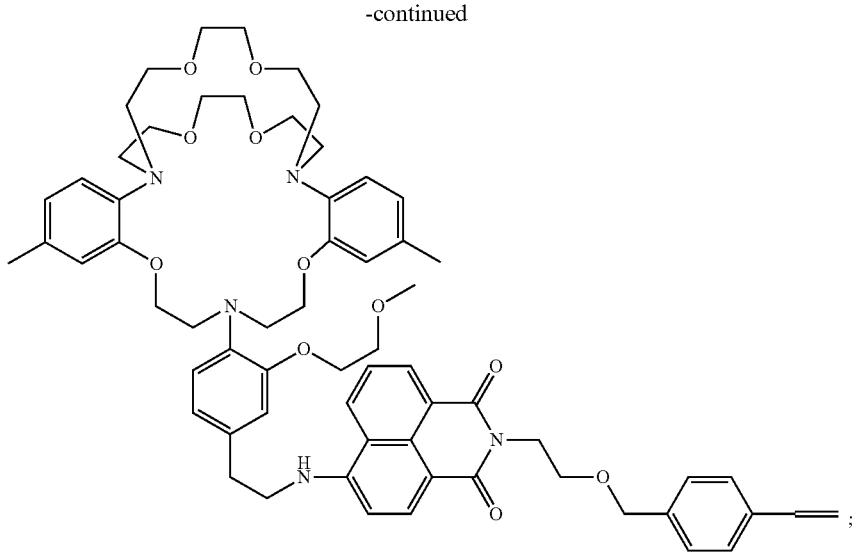
or a salt form thereof.
Also provided herein is a compound of formula (2):
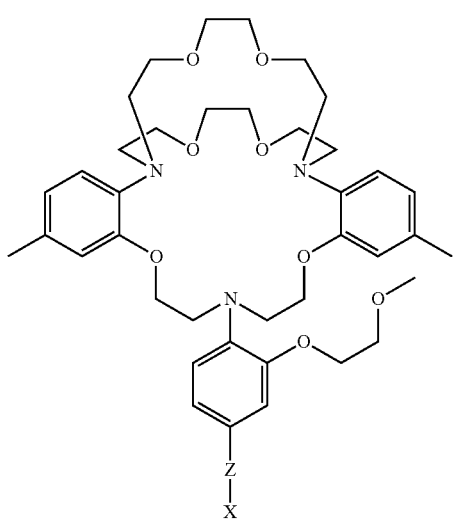
or a salt form thereof, wherein: Z is selected from the group consisting of:
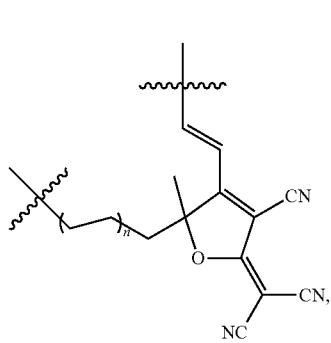
n is an integer from 0 to 3; and X is selected from the group consisting of: H, OH,
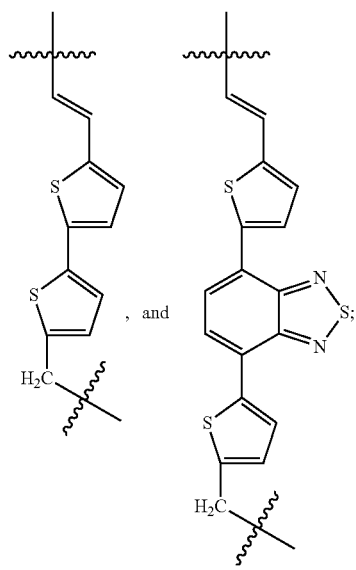
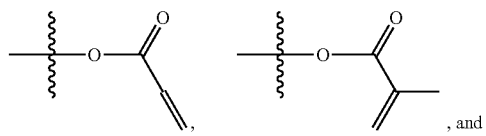, and
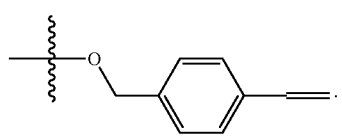

Non-limiting examples of a compound of formula (2) include:
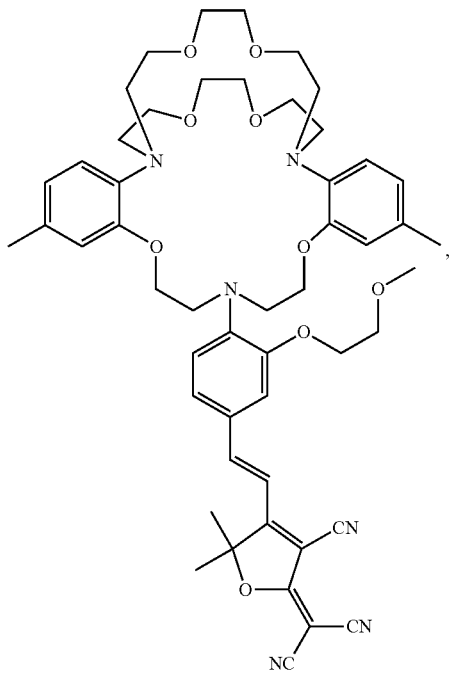,
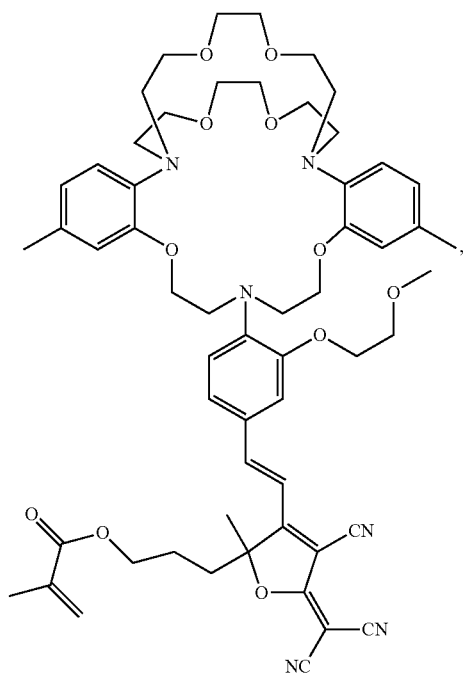,
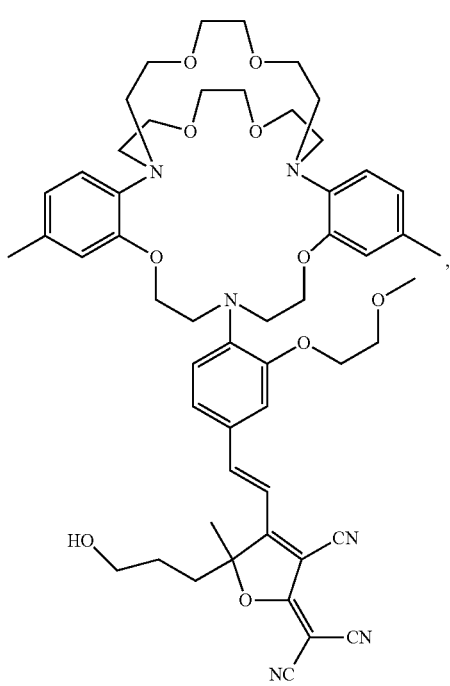,
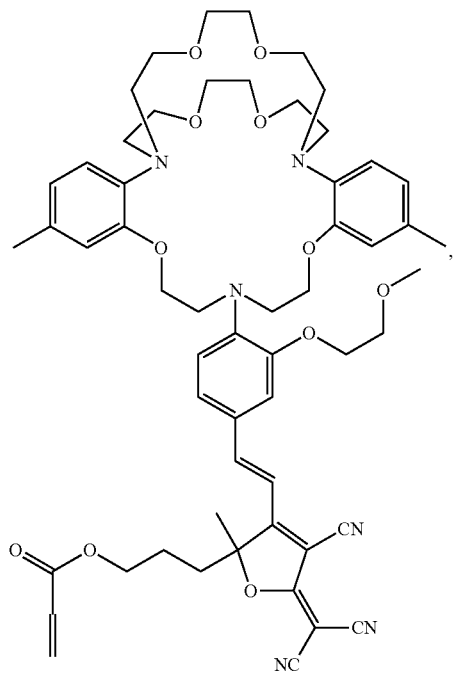, 9
-continued
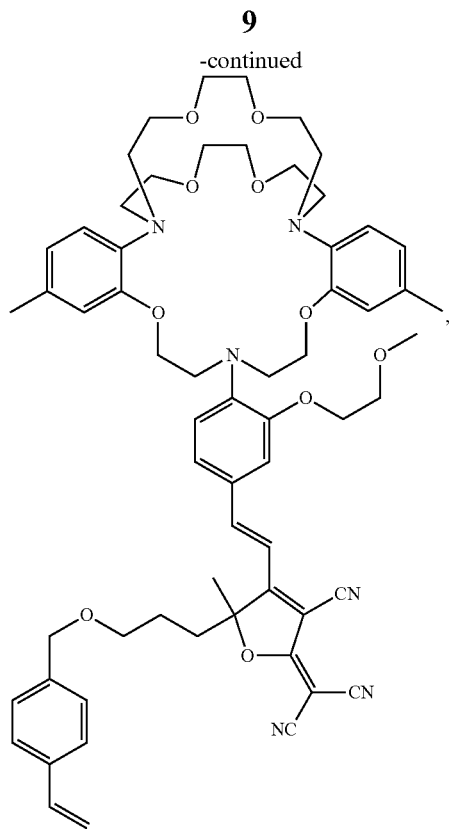
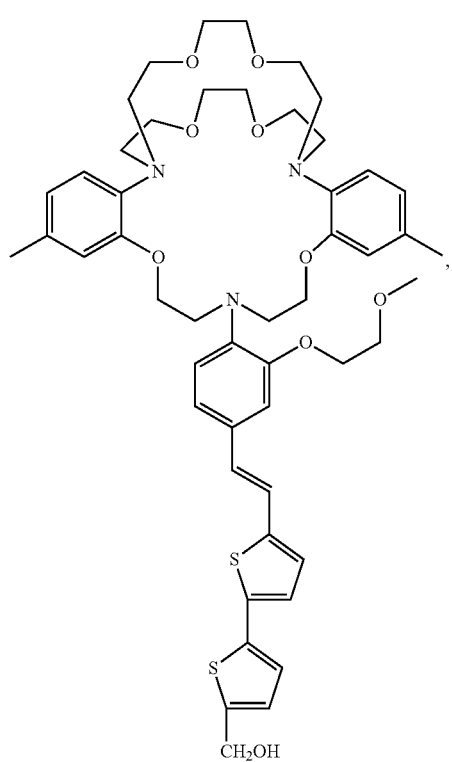
10
-continued
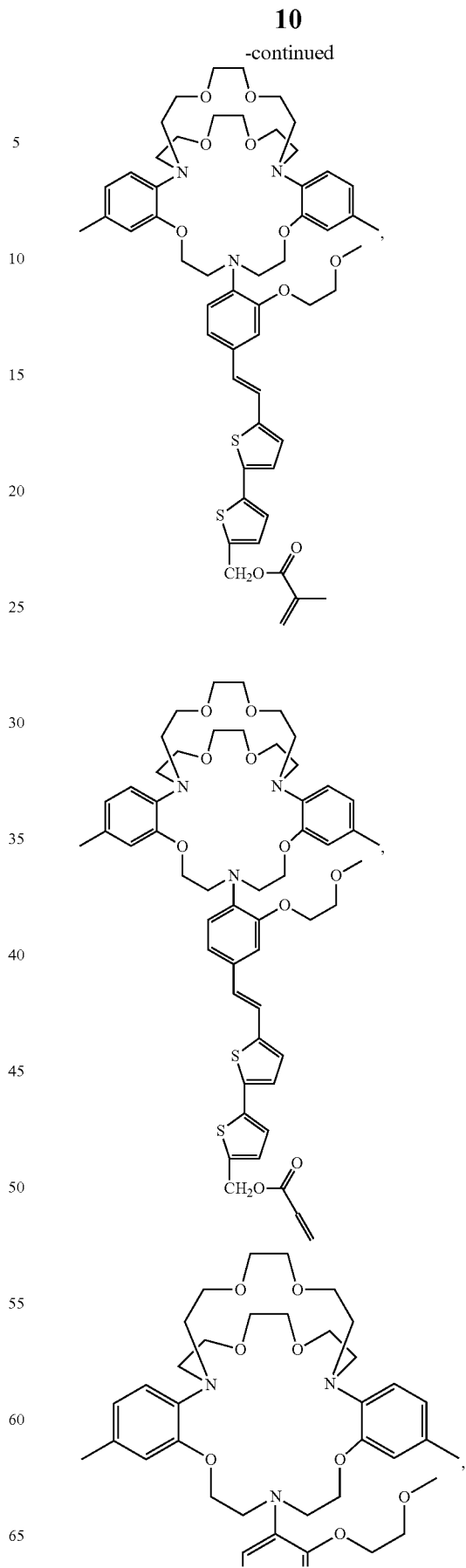

11
-continued
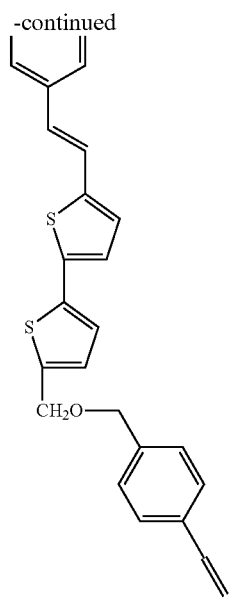
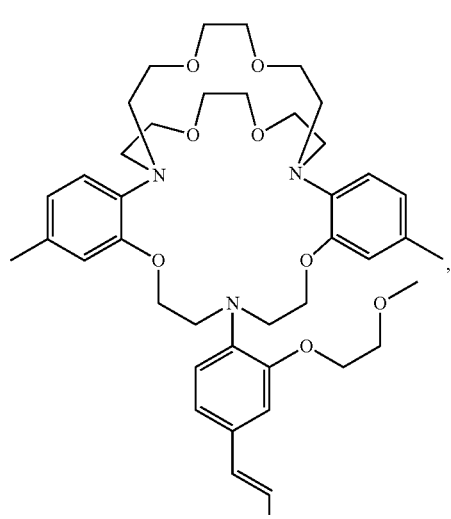
12
-continued
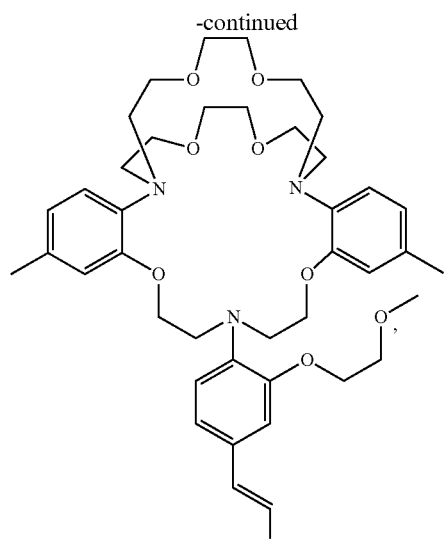
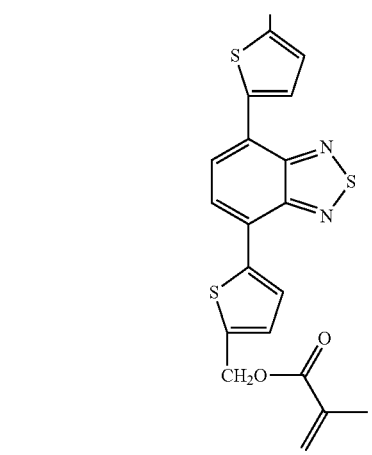
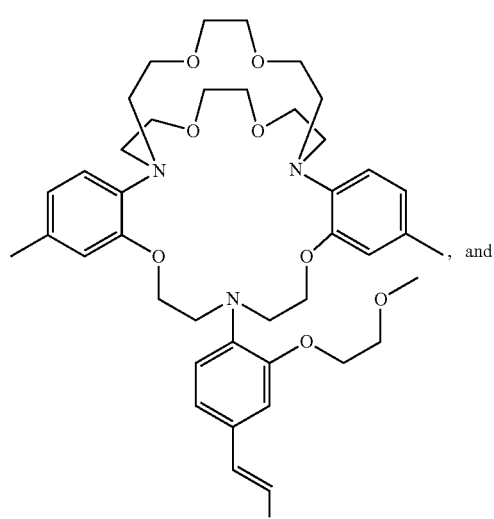
, and

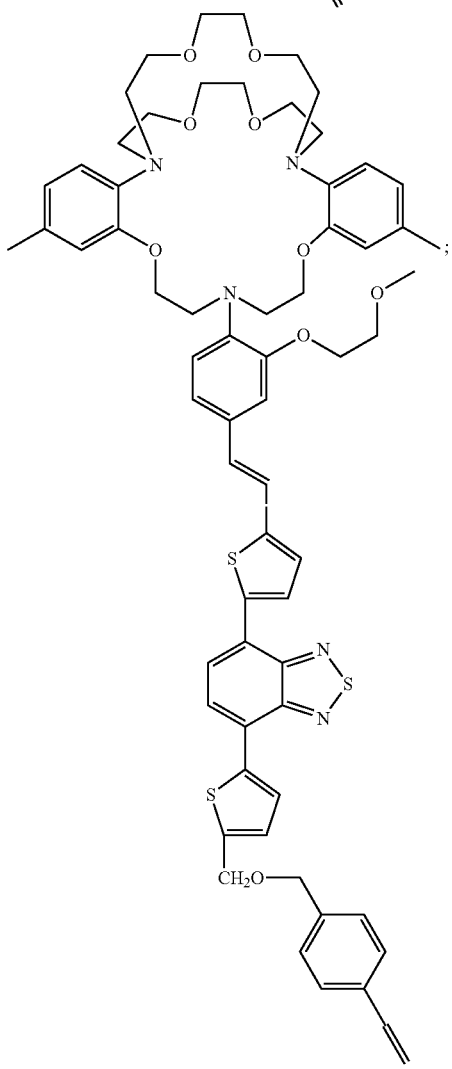

or a salt form thereof.

The compounds described above can be incorporated into a random copolymer comprising: from about 0.01 to about 10% by weight A; from about 10 to about 90% by weight B; from about 10 to about 90% by weight C; wherein A is a compound of formula (1) or (2); B is a biocompatible polymer; and C is a targeting group. In some embodiments, the sum of A, B, and C is 100% by weight of the copolymer.

A biocompatible polymer (B) can include any suitable polymer capable of polymerizing with A and C. For example, a biocompatible polymer can be selected from the group consisting of: dextran, chitosan, glycol chitosan, poly-L-lysine, poly-aspartic acid, PEG and derivatives thereof, poly(amino acid)s, poly(N-isopropyl acrylamide) (PNIPAAm), poly(dimethylaminoethyl methacrylate) (PDMEM), poly(aminoethyl methacrylamide) (PAMEM), poly[(N-2-hydroxypropyl)methacrylamide] (PHPMA), polyacrylamide, poly(2-hydroxyethyl methacrylate), poly(2-methacryloxyethyl sulfonic acid), poly(methacryloxyethyl trimethyl ammonium chloride), poly(vinyl pyridine), and poly[poly(ethylene glycol)methacrylate]. In some embodiments, a biocompatible polymer (B) is selected from the group consisting of:

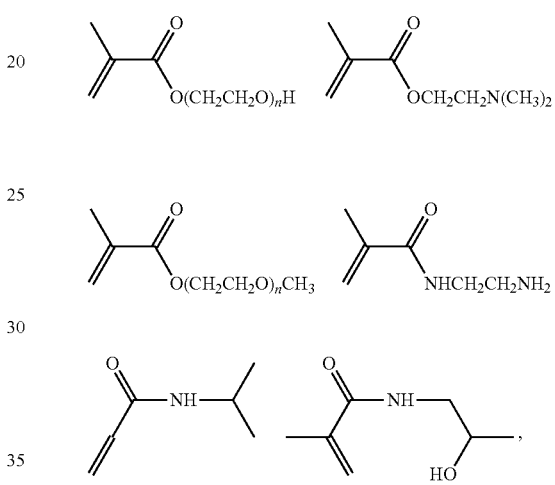

wherein each n is independently an integer from 0 to 30.

A targeting group (C) can be selected from the group consisting of: polypeptides, antibodies, receptor ligands, carbohydrates, lipids, folic acid, hormones, growth factors, antigens, aptamers, chlorotoxin, and nucleic acids. In some embodiments, the targeting group (C) further comprises a linking group. For example, the targeting group can be selected from:

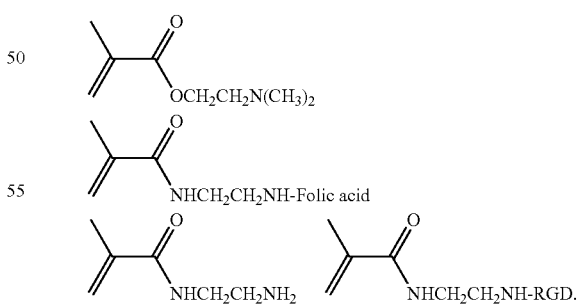

In some embodiments, the random copolymer can further comprise from about 10 to about 100% by weight D, wherein D is a fluorescent oxygen sensor. For example, the sum of A, B, C, and D are 100% by weight of the copolymer. In some embodiments, a fluorescent oxygen sensor (D) can include a compound having the formula:

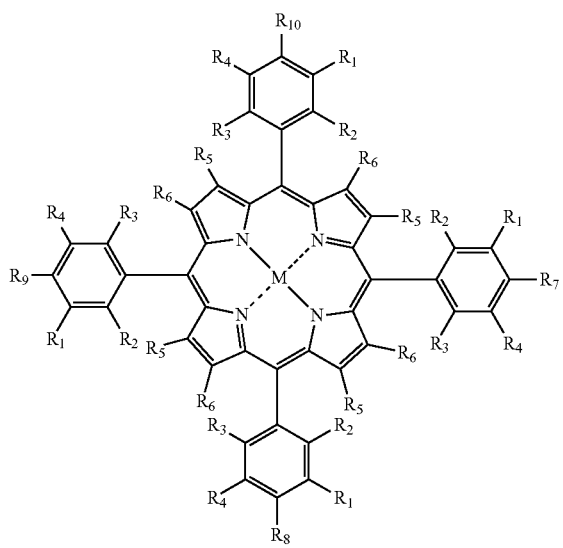

or a salt form thereof, wherein: M is Pt or Pd; $R_1$, $R_2$, $R_3$, $R_4$, $R_5$, and $R_6$ are independently selected from the group consisting of: H, F, Cl, Br, I, $CH_3$, $OCH_3$, and $OC_2H_5$; $R_7$, $R_8$, $R_9$, and $R_{10}$ are independently selected from the group consisting of: $(CH_2)_nOH$, $O(CH_2)_nOH$, $NH(CH_2)_nOH$, $(CH_2)_nOW$, $O(CH_2)_nOW$, $NH(CH_2)_nOW$, $(OCH_2CH_2)_nOH$, $NH(CH_2CH_2O)_nH$, $(OCH_2CH_2)_nOW$, $NH(CH_2CH_2O)_nW$; W is selected from the group consisting of:

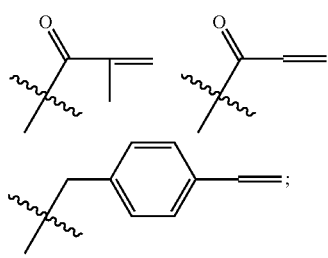

and
n is an integer from 0 to 10. For example, D can be:

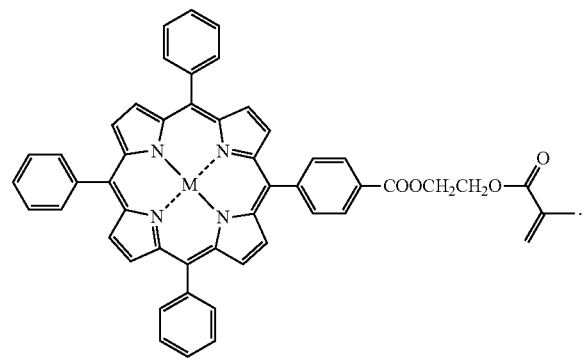

This disclosure also provides a nanoparticle comprising polymerized monomers of one or more compounds of formula (1) and (2). In some embodiments, the nanoparticles can further comprise polymerized monomers of a targeting group (e.g., folic acid and cRGD), biocompatible polymer, and/or fluorescent oxygen sensor or pH sensor as described herein. For example, the monomers can be polymerized in a random copolymer. In some embodiments, the diameter of the nanoparticle is about 1 nm to about 300 nm.

The polymerized monomers of formula (1) and (2) can also be used in a polymer thin film. In some embodiments, the thin film is formed on a substrate. For example, glass (e.g., organic or inorganic glass), transparent polymer, and transparent copolymer polymeric mixture. In some embodiments, the substrate is selected from the group consisting of plasticized or non-plasticized poly(vinyl chloride) (PVC), sol-gel materials, polyvinylformal-silica mixtures, hydrogels, polyurethanes, poly(2-hydroxyethyl methacrylate), polyacrylamide, polydimethylsiloxane, polyethylene terephthalate, polystyrene, and mixtures thereof. In some embodiments, the substrate is quartz glass. In other embodiments, the substrate is an optic fiber bundle. The thickness of the polymer thin film can be from about 0.1 to about 100 μm.

Also provided herein is a sensing film comprising a substrate, as described above, covalently bound to a compound of formula (1) and/or (2). In some embodiments, the compound is covalently bound to the substrate through a linker. The sensing film can further comprise, for example, a fluorescent oxygen sensor, a fluorescent pH sensor, or mixtures thereof.

Intracellular sensors as described herein can also include a targeted compound having the formula:

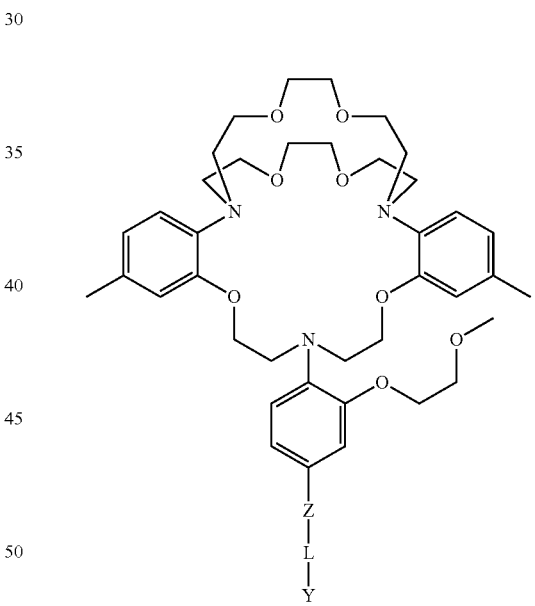

or a salt form thereof, wherein: Z is selected from the group consisting of:

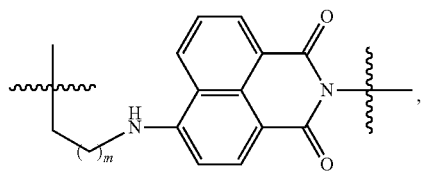

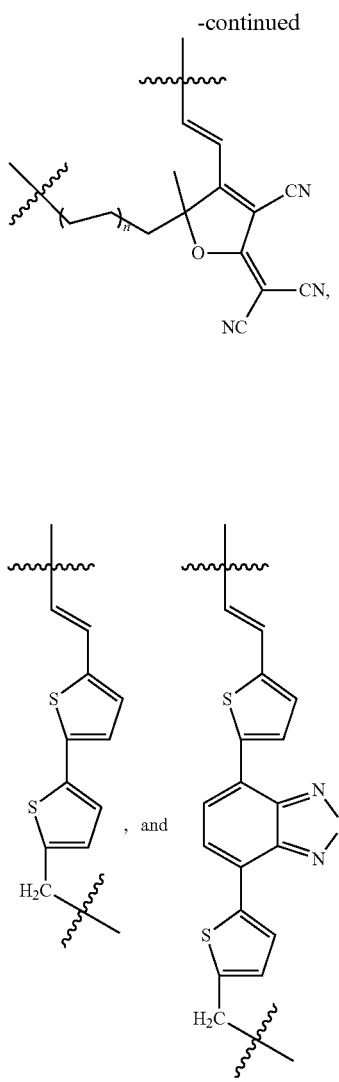

m is 0 or 1; n is 0 or 1; L is a linker; and Y is a targeting group.

A targeted compound includes, for example, a compound having the formula:

or a salt form thereof, wherein: m is 0 or 1; L is a linker; and Y is a targeting group.

A targeting group can include, for example, polypeptides, antibodies, receptor ligands, carbohydrates, lipids, folic acid, hormones, growth factors, antigens, aptamers, chlorotoxin, and nucleic acids. In some embodiments, the targeting group is selected from the group consisting of: folic acid, cyclo (arginine-glycine-aspartic acid) (cRGD), TAT peptides, and galactose. Non-limiting examples of a targeted compound include:

-continued

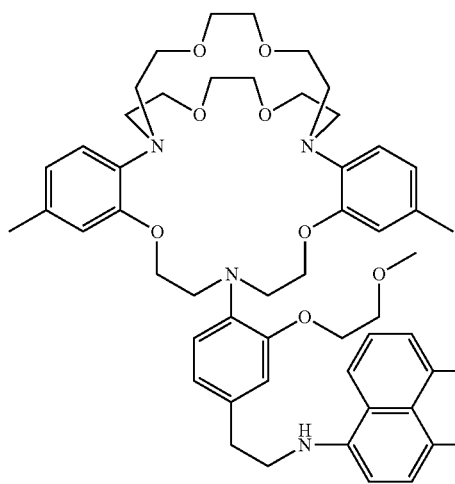
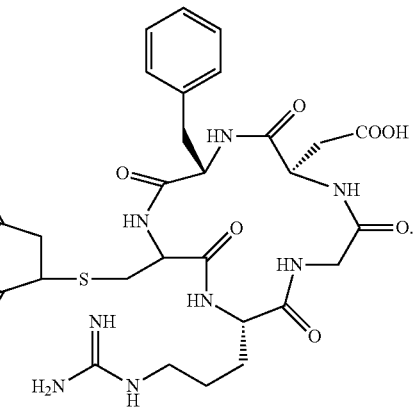

This disclosure also provides a method of measuring potassium ion concentration in a sample. In some embodiments, the method can include contacting the sample with a compound of formula (1), formula (2), or a targeted compound and measuring the fluorescence emitted by the compound. In some embodiments, the sample is a fluid sample. For example, a fluid sample comprising one or more cells. The potassium ion concentration can be measured in the extracellular fluid of the sample or in the intracellular fluid of the cells.

For example, a method of measuring potassium ion concentration in a cell is provided, the method comprising contacting the cell with a compound as described herein and measuring the fluorescence emitted by the compound. In some embodiments, the fluorescence is measured using spectrofluorimetry. Any suitable cell can be used, for example, a cancer cell. In some embodiments, the compound is contacted with the cell using microinjection. The compounds described herein can be used as discrete compounds or as a polymerized monomer in a polymer thin film or a nanoparticle. For example, in some embodiments the compound is covalently attached to a surface.

In addition, a method of imaging a cancer cell in a patient is provided, the method comprising administering to the patient an effective amount of a compound as described herein and imaging the patient.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
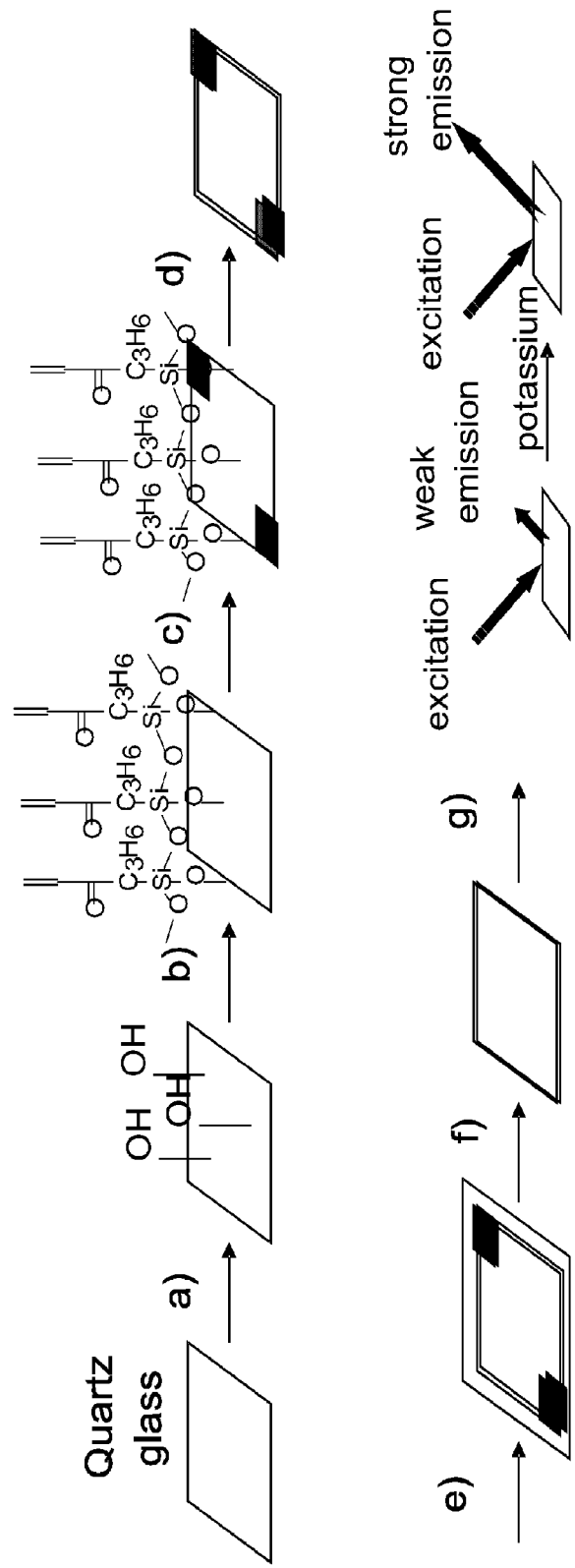
FIG. 1 is a schematic illustration of the preparation of a sensing film: (a) oxygen plasma treatment is used to generate active hydroxyl groups; (b) vapor deposition of thin trimethylsilylpropyl acrylate (TMPSA) layer; (c) 25 μm tape used to control membrane thickness; (d) sensor solution dispensed onto modified quartz surface; (e) solution covered with a cover glass and polymerized at 80° C. for 1.5 h; (f) cover glass and tape removed; film rinsed using methanol and double-distilled water; and (g) sensing membrane responding to potassium ions.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one of ordinary skill in the art to which this disclosure belongs. All patents, applications, published applications, and other publications cited herein are incorporated by reference in their entirety. In the event that there is a plurality of definitions for terms cited herein, those in this section prevail unless otherwise stated.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzensulfonate, p-toluenesulfonate, p-trifluoromethylbenzenesulfonate, hydroxide, aluminates and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. Conventional methods for preparing salt forms are described, for example, in *Handbook of Pharmaceutical Salts: Properties, Selection, and Use*, Wiley-VCH, 2002.

The compounds described herein, including salts thereof, can be prepared using known organic synthesis techniques and can be synthesized according to any of numerous possible synthetic routes.

The reactions for preparing the compounds can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6) (2004), which is incorporated herein by reference in its entirety) and normal phase silica chromatography.

Sensing Compounds

Provided herein are potassium sensing molecules of formula (1):

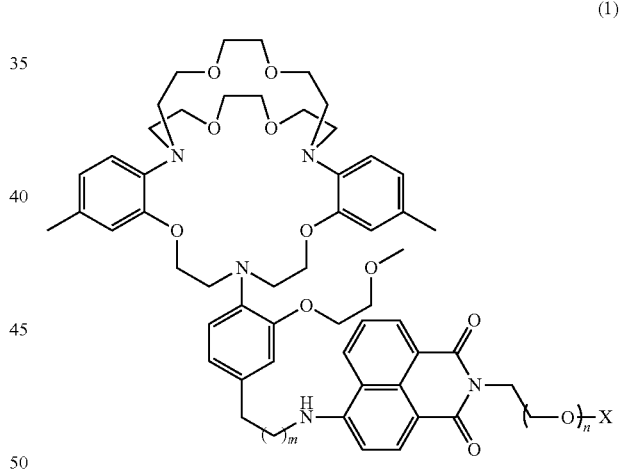

(1)

or a salt form thereof, wherein m is 0 or 1; n is an integer from 0 to 3; and X is selected from:

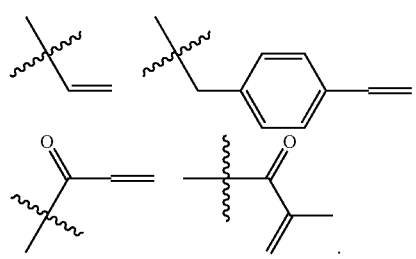

Formula (1) can include, for example,
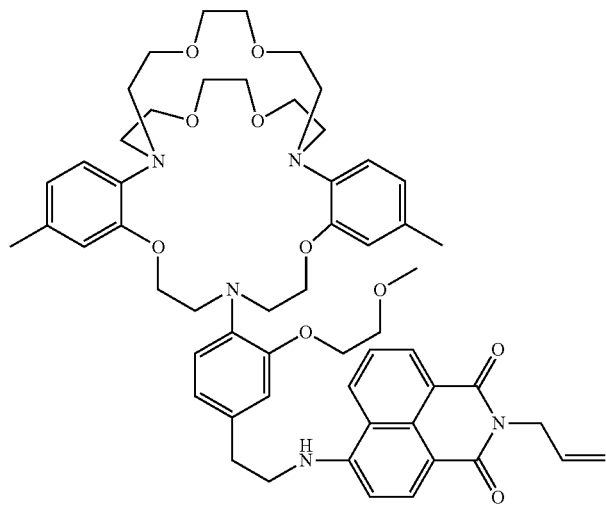
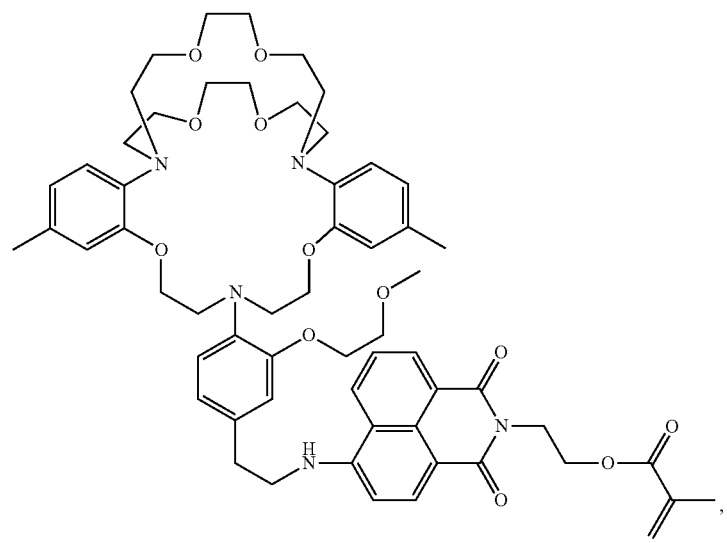
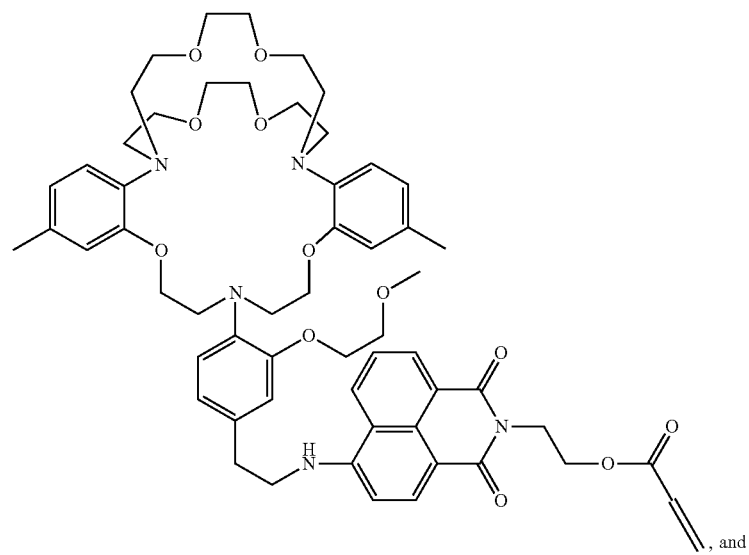
, and

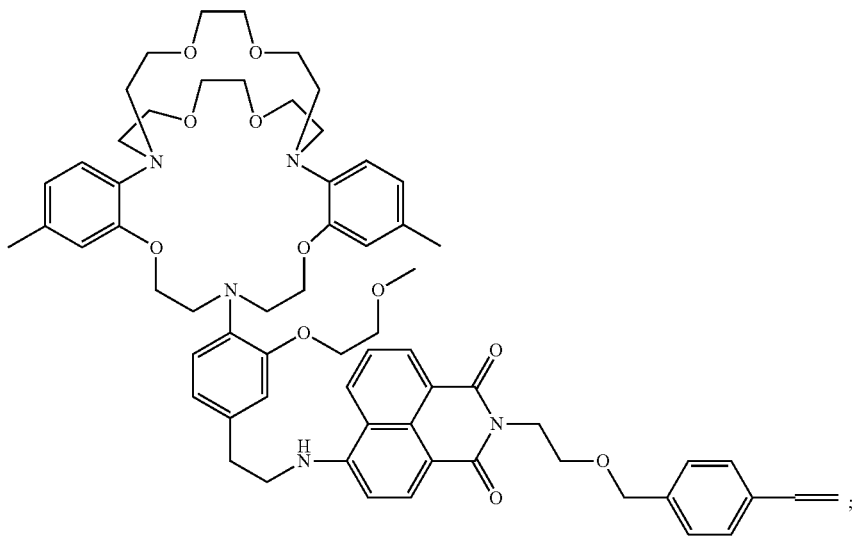 [SMILES: C=Cc1ccc(COCCN2C(=O)c3cccc4c(NCCc5ccc(N6CCOc7cc(C)ccc7N7CCOCCOCCN(CCOCCOCC7)c7ccc(C)cc7OCC6)c(OCCOC)c5)ccc(c34)C2=O)cc1]

or a salt form thereof.

A compound of formula (1) can be prepared, for example, as shown in Scheme 1 and described in Examples 1 and 18. In particular, a compound of formula (1) may be prepared upon reaction of an amino compound (I) and a halo compound (II) in the presence of any reagent which would achieve formation of the compound of the N-aryl amine. For example, an amine of compound (I) can be reacted with a halo compound (II) in the presence of a base. Suitable bases include non-nucleophilic bases such as N,N-diisopropylethylamine (DIPEA), carbonate salts (e.g., $K_2CO_3$ and $Cs_2CO_3$), triethylamine (TEA), pyridine, tributylamine, and 1,8-diazabicycloundec-7-ene (DBU).

Scheme 1

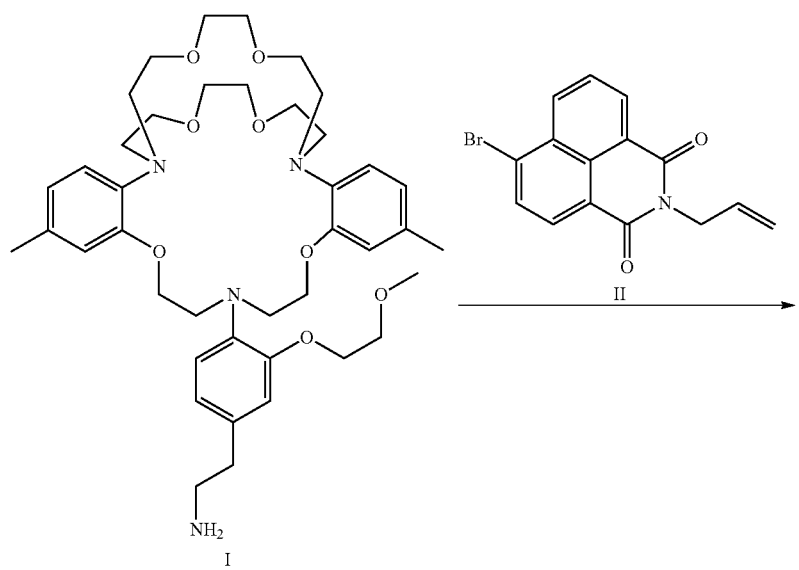

-continued
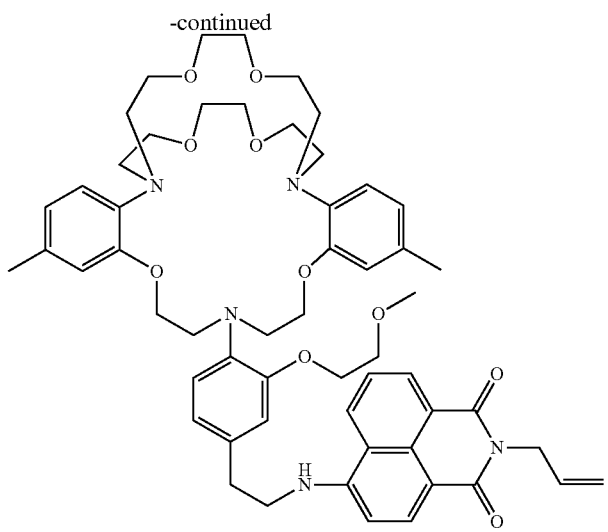
Also provided herein are potassium sensing compounds of formula (2):
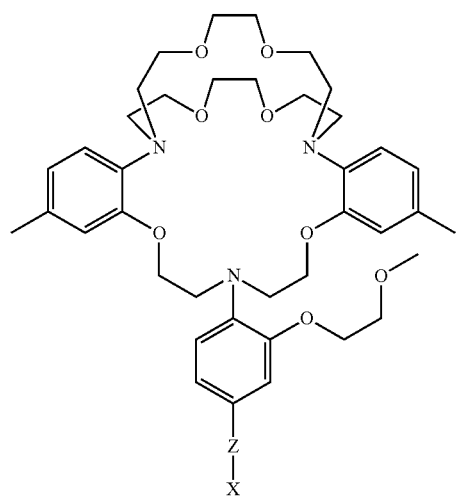
(2)
or a salt form thereof, wherein Z is selected from:
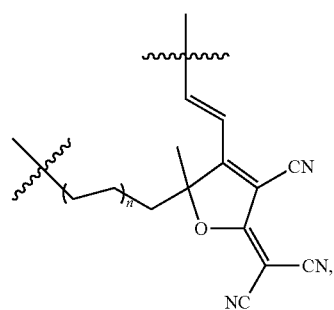
-continued
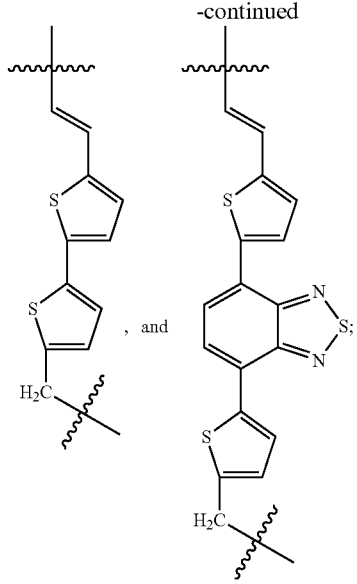
n is an integer from 0 to 3 (e.g., 0, 1, 2, and 3); X is selected from: H, OH,
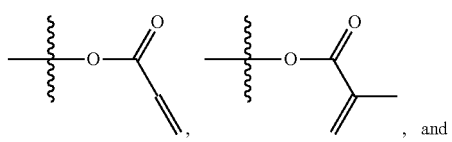
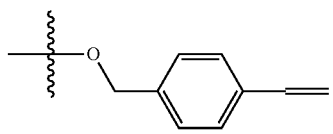

31
Formula (2) can include, for example,
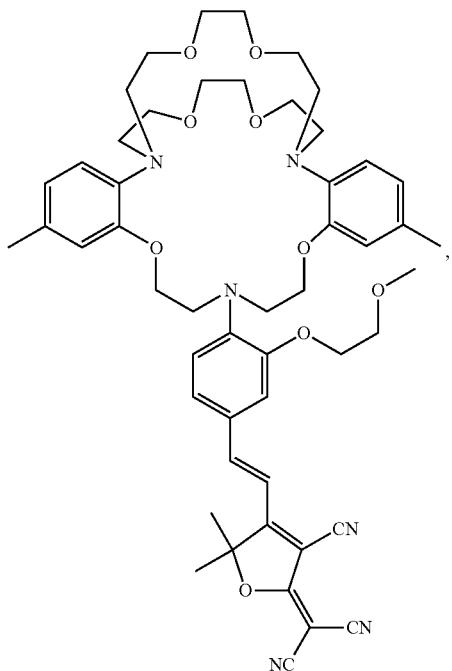
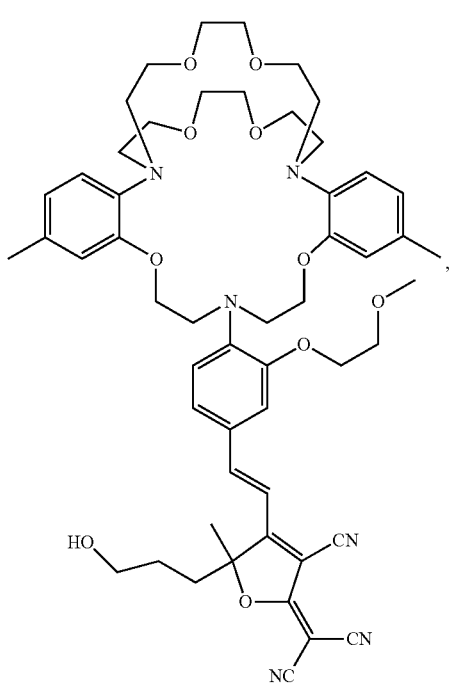
32
-continued
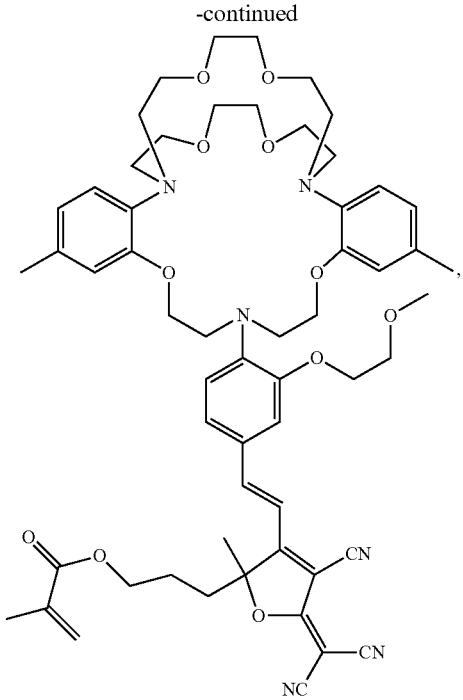
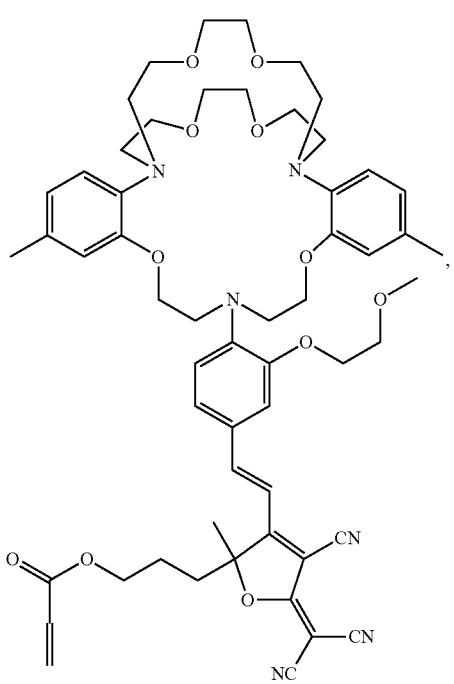

33
-continued
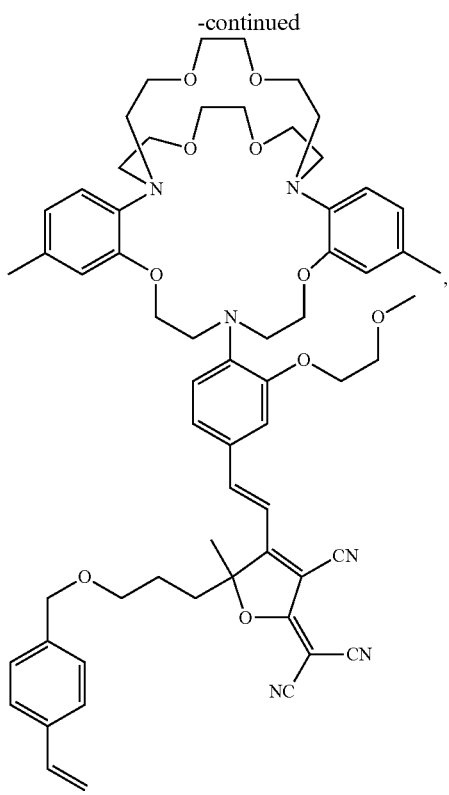
34
-continued
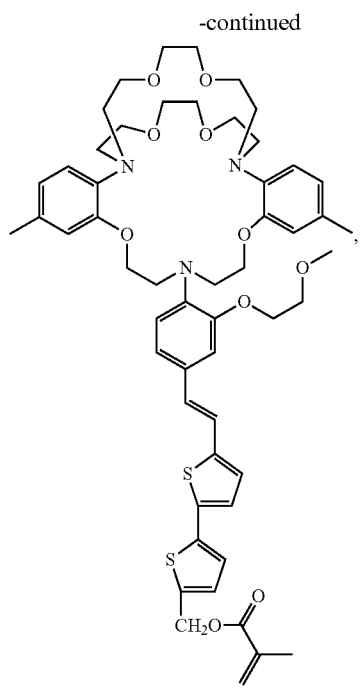
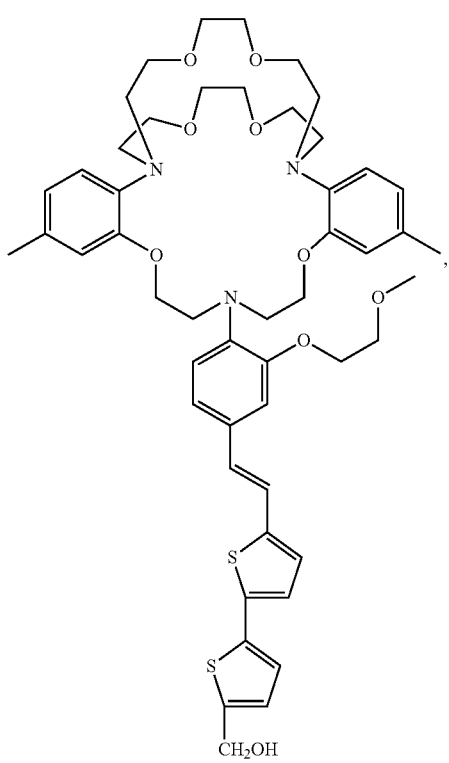
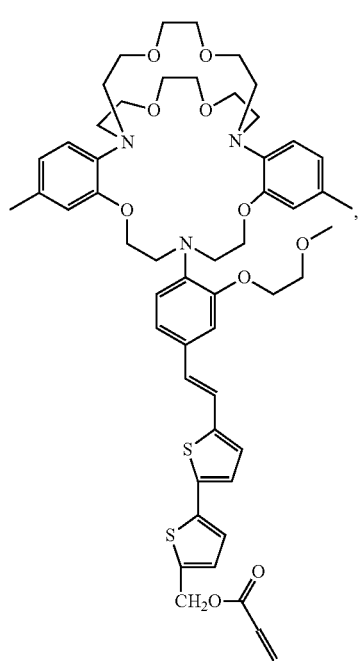

35
-continued
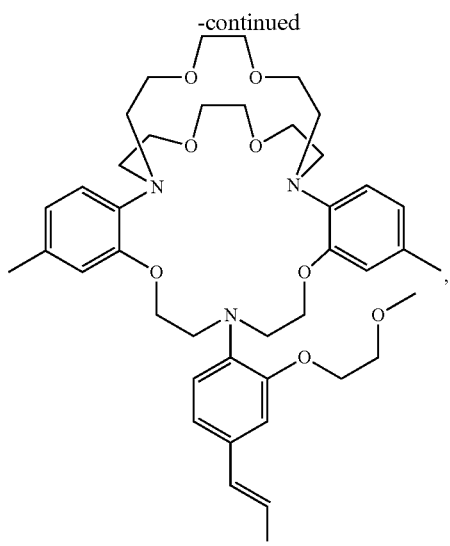
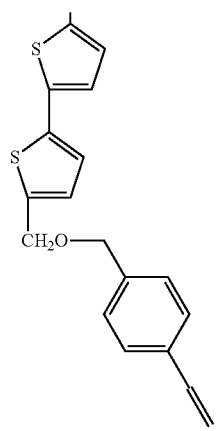
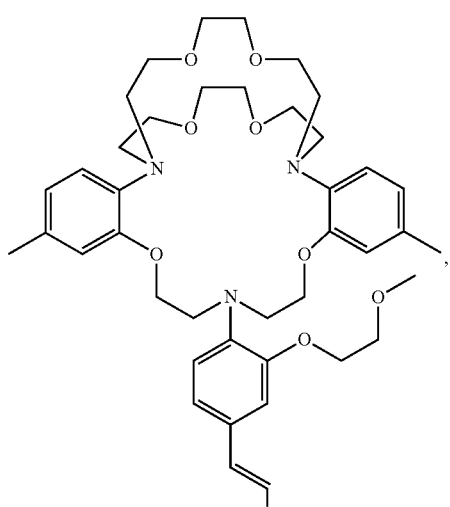
36
-continued
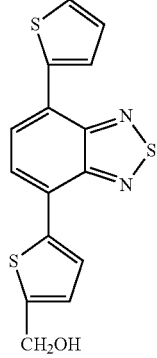
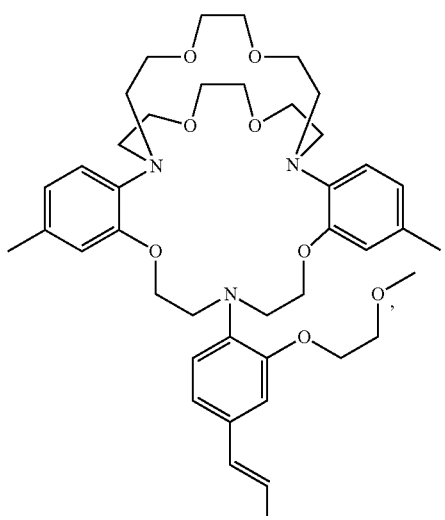
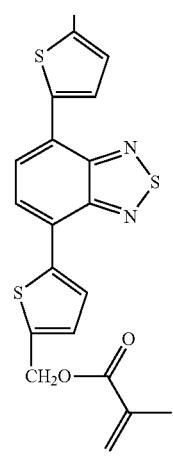

37

-continued

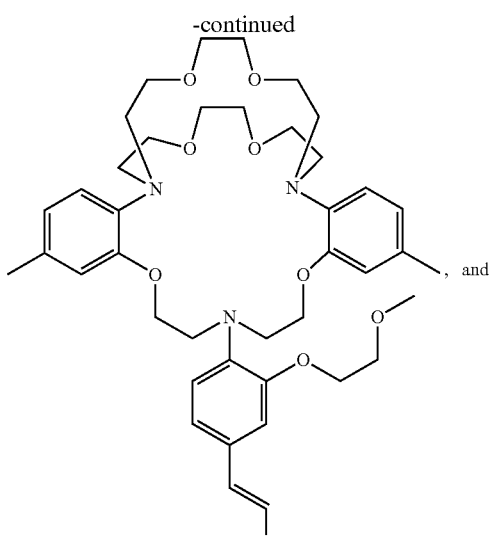
, and

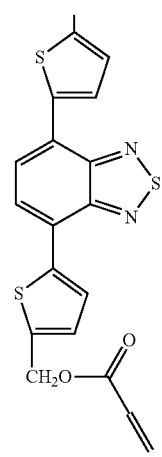

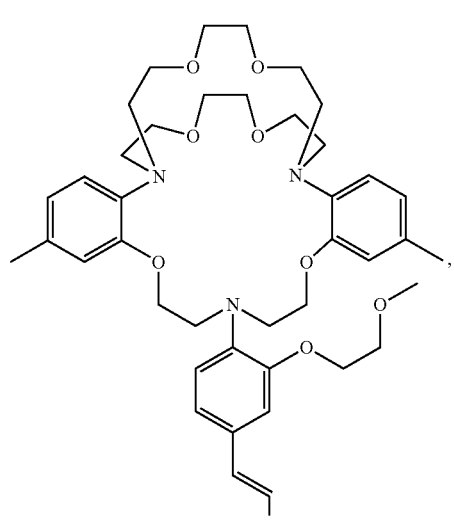

38

-continued

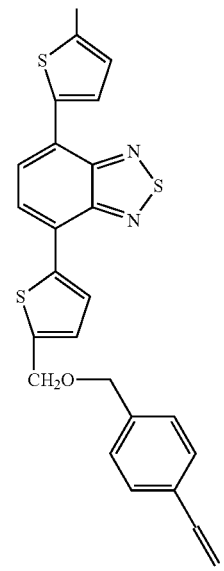

or a salt form thereof.

A compound of formula (2) can be prepared, for example, as shown in Scheme 2 and described in Examples 2 and 10. In particular, a compound of formula (2) may be prepared upon the condensation of an aldehyde compound (III) and a compound (IV) in the presence of any reagent which would achieve formation of targeted probes as potassium ion sensors. For example, an aldehyde of compound (III) can be reacted with an activated compound (IV) in the presence of a catalyst. Suitable catalysts include, but are not limited to, bases such as ammonium acetate, pyridine, diisopropylethyl amine, triethyl amine, lithium ethoxide, and piperidine.

Scheme 2

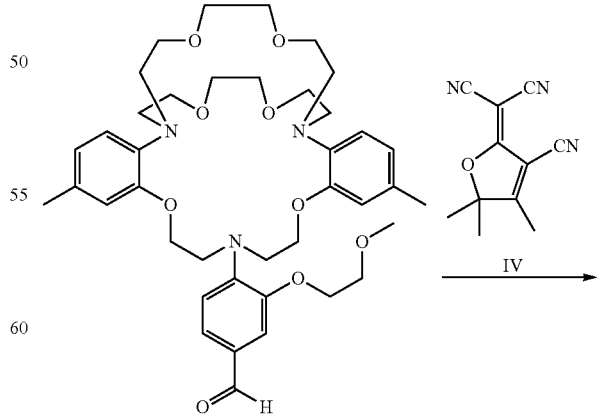

-continued

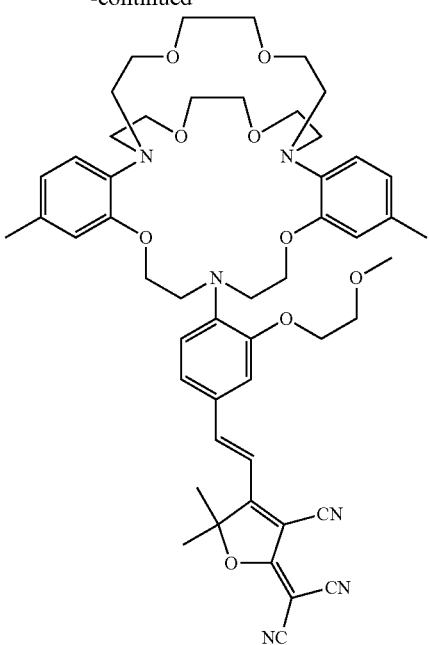

In some embodiments, the compounds described herein may be modified to contain targeting groups. For example, a compound of formula (3):

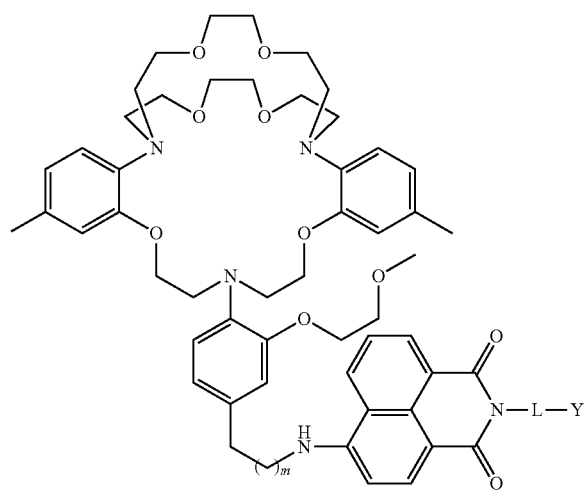

or a salt form thereof, wherein m is 0 or 1; L is a linker; and Y is a targeting group.

Suitable targeting groups include specific and nonspecific targeting groups. For example, nonspecific targeting groups can be used to enhance nonspecific uptake the compounds through the incorporation of groups capable of interacting with the cellular membrane to enhance cellular uptake. Non-limiting examples of suitable nonspecific targeting groups include: glucose, sugar, dimethyl amine, diethyl amine, tetraalkyl ammonium salt, poly(dimethylaminoethyl methacrylate) (PDMEM) and poly(aminoethyl methacrylamide) (PAMEM).

Specific targeting groups can also be used to enhance specific cellular uptake of the potassium sensors. Non-limiting examples of suitable specific targeting groups include polypeptides, antibodies, receptor ligands, carbohydrates, lipids, folic acid, hormones, growth factors, antigens, aptamers, chlorotoxin, and nucleic acids. For example, folic acid can facilitate specific uptake of the compound by folate receptor rich/over expressing cancer cell lines such as human cervical HeLa cells and human nasopharyngeal epidermal carcinoma KB cells. In some embodiments, use of a polypeptide can facilitate specific uptake by targeted cells. For example, cyclic(arginine-glycine-aspartic acid) (cRGD) can target uptake by $\alpha_v\beta_3$-integrin rich cancer cell lines, such as human brain glioblastoma U87-MG cells.

A linker can be any suitable organic group which serves to space the sensor from the targeting group so as to maximize uptake and/or sensing. In some embodiments, L and Y are covalently bound to one another. For example, a linker can include one or more of a $C_{1-20}$ alkyl, $C_{1-20}$ alkoxy, amino, and thiol moiety. In some embodiments, the linker can include a pyrrole-2,5-dione. The linker may also include a polyethylene glycol (PEG) linker. Examples of such linkers are well known to those skilled in the art. In some cases the linker and targeting group are noncovalently bound to one another. Examples of noncovalent means for conjugation of a linker and a targeting group include, e.g., ionic bonding, hydrophobic interactions, ligand-nucleotide binding, chelating agent/metal ion pairs or specific binding pairs such as avidin/biotin, streptavidin/biotin, anti-fluorescein/fluorescein antibodies, anti-2,4-dinitrophenol (DNP)/DNP antibodies, anti-peroxidase/peroxidase, anti-digoxigenin/digoxigenin or, more generally, receptor/ligand.

Non-limiting examples of a compound of formula (3) include:

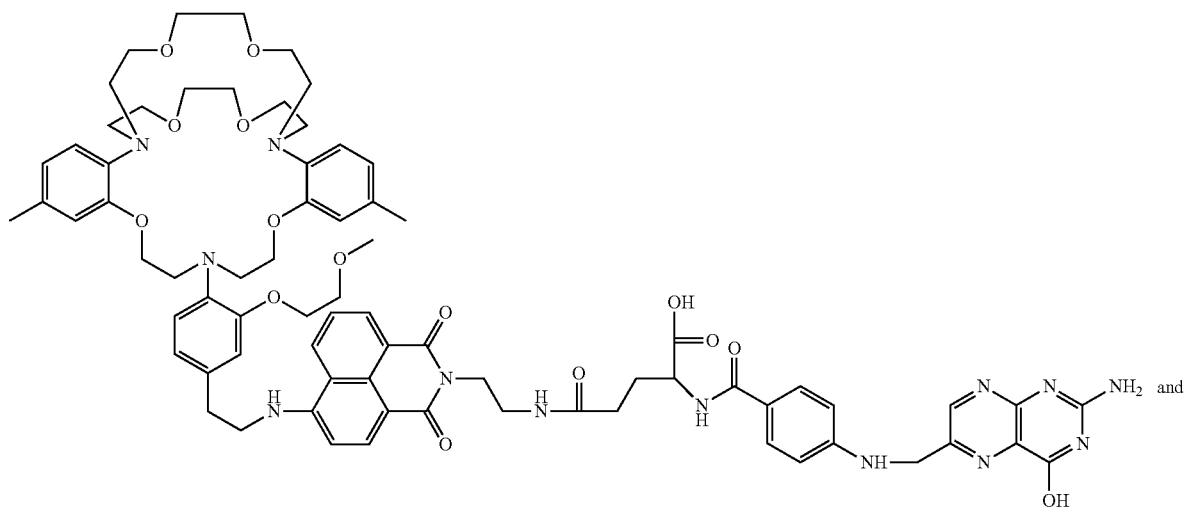

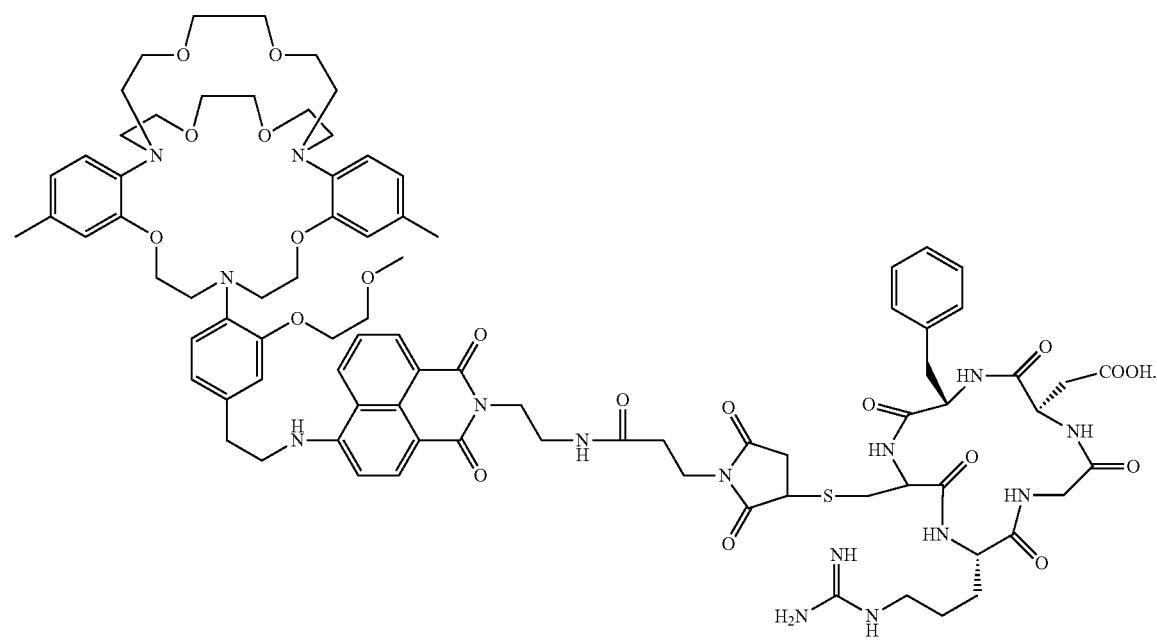

A compound of formula (3) can be prepared, for example, as shown in Schemes 3 and 4. In particular, a compound of formula (3) may be prepared upon the coupling of amine derivative of a compound of formula (1) or (2) and a targeting group in the presence of any reagent which would achieve formation of a peptide bond. For example, as shown in Scheme 3, an amine derivative of a compound of formula (1) can be directly linked to folic acid in the presence of a coupling agent. Suitable coupling agents include, but are not limited to, N-(3-dimethylaminopropyl)-N'-ethylcarbodiimide hydrochloride (EDC), N,N'-dicyclohexylcarbodiimide (DCC), ArB(OH)$_2$ reagents, Sn[N-(TMS)$_2$]$_2$, N,N'-carbonyldiimidazole, POCl$_3$, TiCl$_4$, molecular sieves, Lawesson's reagent, and (MeO$_2$)POCl. See, for example, Klausner, Y. S, and Bodansky, M. *Synthesis,* 1972, 453, which is incorporate herein in its entirety. Alternatively, as shown in Scheme 4, an amine derivative of a compound of formula (1) can be reacted with a linker (e.g., 3-(2,5-dioxo-2,5-dihydro-1H-pyrrol-1-yl) propanoic acid) in the presence of a coupling agent as described above. The resulting derivative of the compound of formula (1) can then be reacted with a typical targeting group possessing a thio (—SH)-containing cRGD moiety, e.g., cyclo(Arg-Gly-Asp-D-Phe-Cys) or cRGDfc in DMSO or buffers (HEPES, PBS, or Tris HCl) through Michael addition reaction.

Scheme 3
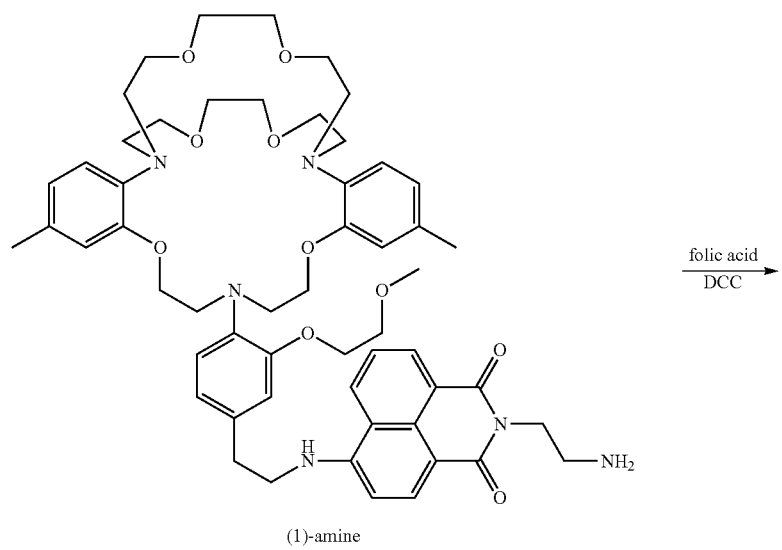
(1)-amine
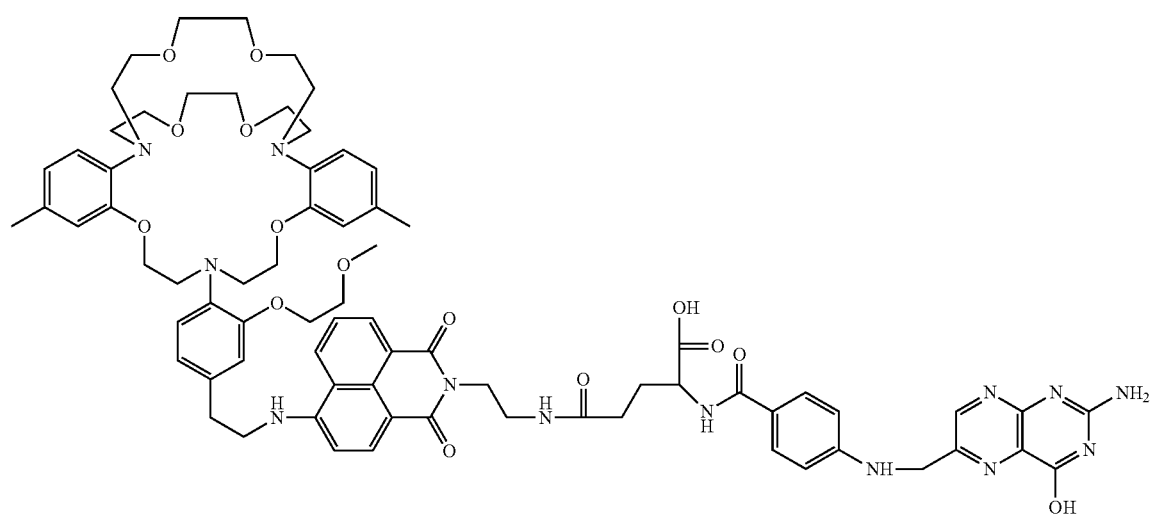
Folated (1)

Scheme 4
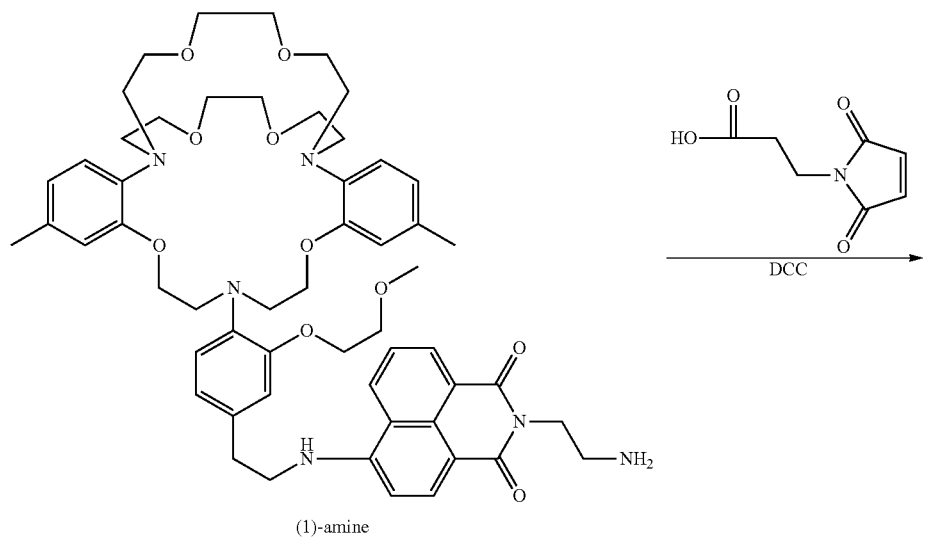
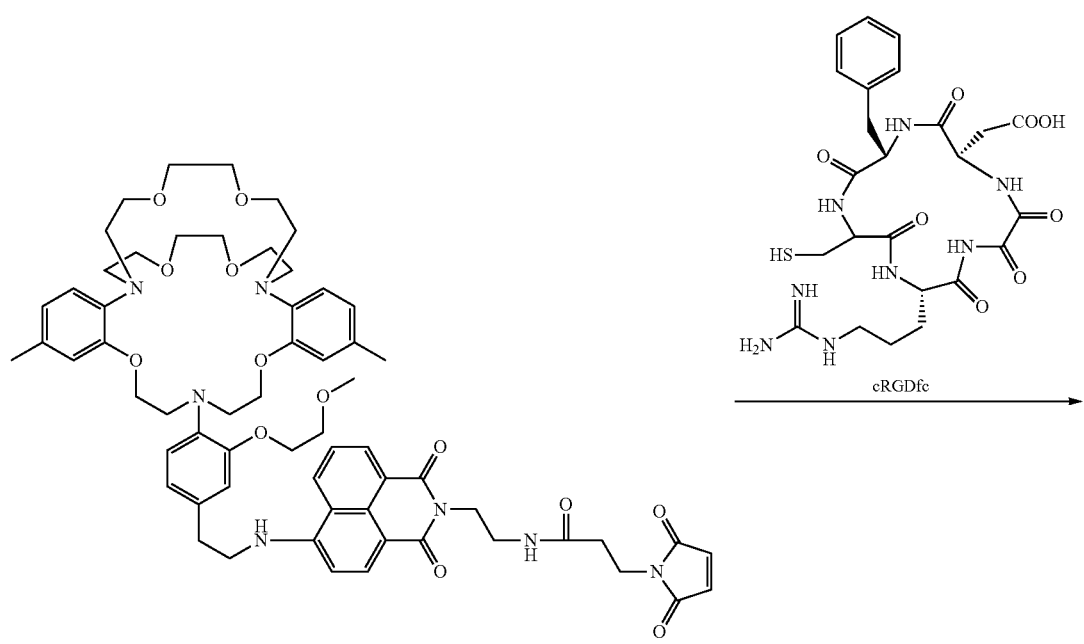

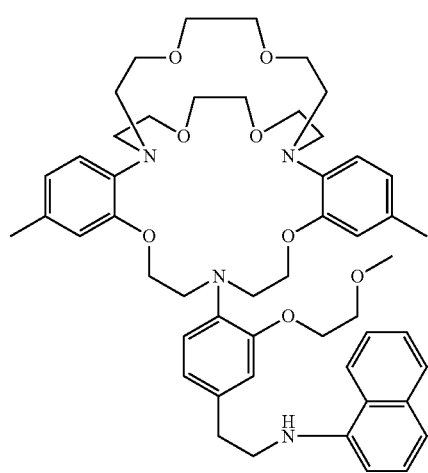
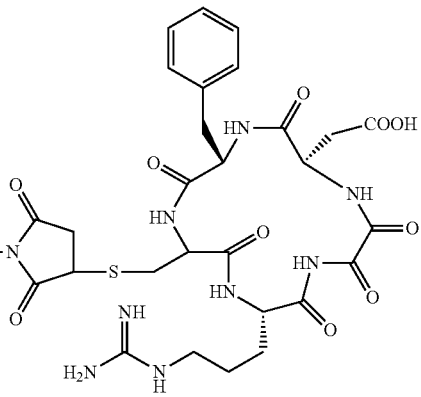
cRGD-(1)
Polymers
Further provided herein are polymers composed of one or more polymerized monomers of a compound of formula (1) as described above. In some embodiments, a polymer comprises one or more polymerized monomers of a compound of formula (2A):
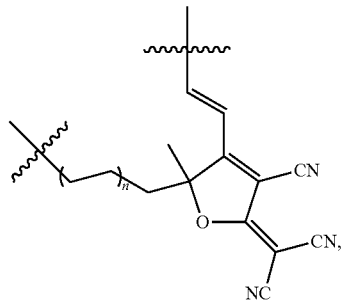
(2)
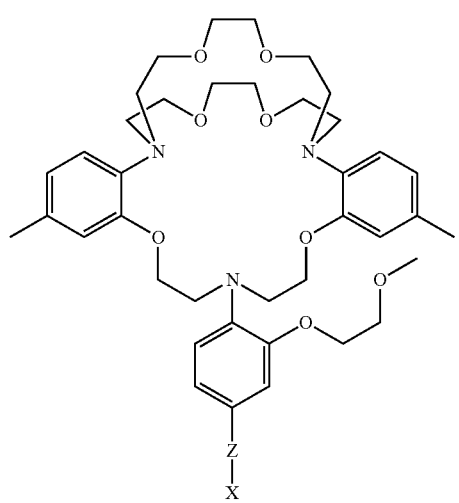
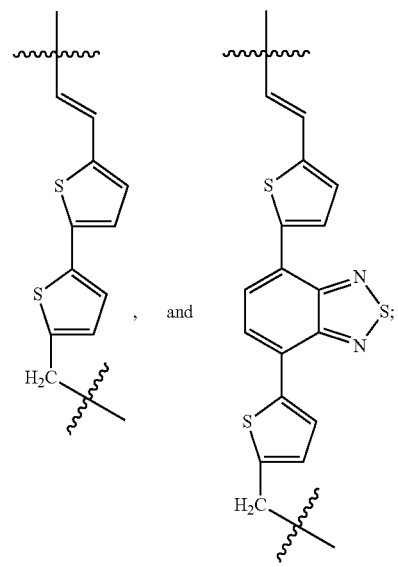
or a salt form thereof, wherein Z is selected from:

n is an integer from 0 to 3 (e.g., 0, 1, 2, and 3); and X is selected from:

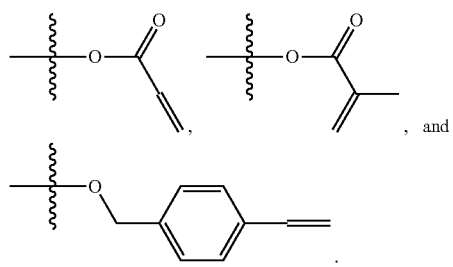

A polymer may be prepared by reacting two or more monomer compounds of formula (1) and/or formula (2A) in the presence of any reagent which would achieve formation of a polymer. In some embodiments, two or more monomer compounds are coupled through thermal polymerization in the presence of a thermal initiator to form a polymer. Suitable thermal initiators include, for example, aliphatic azo compounds such as azobisisobutyronitrile (AIBN), 4,4-azobis(4-cyanovaleric acid), and 1,1'-azobis(cyclohexanecarbonitrile) (ABCN), and organic peroxides such as benzoyl peroxide (BPO), di-t-butylperoxide (tBuOOtBu), methyl ethyl ketone peroxide, lauroyl peroxide, and acetone peroxide, and potassium persulfate. Alternatively, two or more monomer compounds can be coupled through photopolymerization in the presence of a photo-initiator. Suitable photo initiators include, for example, benzophenone, 2,2-dimethoxy-2-phenylacetophenone (DMPA), 2,2-dimethoxyphenylacetophenone (Irgacure 851), and bis(2,4,6-trimethylbenzoyl)-phenylphosphineoxide (Irgacure 819).

In some embodiments, the polymer may be formed into a polymer thin film. The polymer thin film can have a thickness ranging from about 0.1 to about 100 μm (e.g., from about 0.5 to about 100 μm; from about 1 to about 100 μm; from about 10 to about 100 μm; from about 25 to about 100 μm; from about 40 to about 100 μm; from about 55 to about 100 μm; from about 65 to about 100 μm; from about 80 to about 100 μm; from about 0.1 to about 90 μm; from about 0.1 to about 75 μm; from about 0.1 to about 60 μm; from about 0.1 to about 40 μm; from about 0.1 to about 15 μm; from about 0.1 to about 5 μm; from about 0.1 to about 1 μm; from about 5 to about 75 μm; from about 10 to about 80 μm; from about 15 to about 65 μm; and from about 25 to about 50 μm).

In some cases, the polymer thin film may be formed on a substrate, for example, glass, a transparent polymer, or a transparent copolymer polymeric mixture. Suitable substrates include, for example, plasticized or non-plasticized poly(vinyl chloride) (PVC), sol-gel materials, polyvinylformal-silica mixtures, hydrogels, polyurethanes, poly(2-hydroxyethyl methacrylate), polyacrylamide, polydimethylsiloxane, polyethylene terephthalate, polystyrene, and mixtures thereof. In some embodiments, the substrate is an organic or inorganic glass, for example, quartz glass. Alternatively, the substrate can be an optic fiber bundle.

In some embodiments, a random copolymer is provided. A random copolymer can comprise one or more compounds (A) of formula (1) or (2A), one or more biocompatible polymers (B), and one or more targeting groups (C).

Compound (A) can include one or more compounds of formula (1) or (2A) as described above. In some embodiments, a random copolymer can include from about 0.01 to about 10% by weight of a compound (A) (e.g., from about 0.1 to about 10%; from about 0.5 to about 10%; from about 1 to about 10%; from about 2 to about 10%; from about 4 to about 10%; from about 6 to about 10%; from about 8 to about 10%; from about 0.01 to about 8%; from about 0.01 to about 7%; from about 0.01 to about 5%; from about 0.01 to about 3%; from about 0.01 to about 1.5%; from about 0.01 to about 0.8%; from about 0.01 to about 0.4%; from about 0.01% to about 0.1%; from about 0.4% to about 4%; from about 0.75% to about 2.5%; from about 1% to about 6%; from about 3% to about 8%; and from about 2.5% to about 7.5%).

Compound (B) can be any suitable biocompatible polymer. Suitable biocompatible polymers include, for example, dextran, chitosan, glycol chitosan, poly-L-lysine, poly-aspartic acid, PEG and derivatives thereof, poly(amino acid)s, poly(N-isopropyl acrylamide) (PNIPAAm), poly(dimethylaminoethyl methacrylate) (PDMEM), poly(aminoethyl methacrylamide) (PAMEM), poly[(N-2-hydroxypropyl) methacrylamide] (PHPMA), polyacrylamide, poly(2-hydroxyethyl methacrylate), poly(2-methacryloxyethyl sulfonic acid), poly(methacryloxyethyl trimethyl ammonium chloride), poly(vinyl pyridine), and poly[poly(ethylene glycol) methacrylate]. In some embodiments, a compound (B) is selected from:

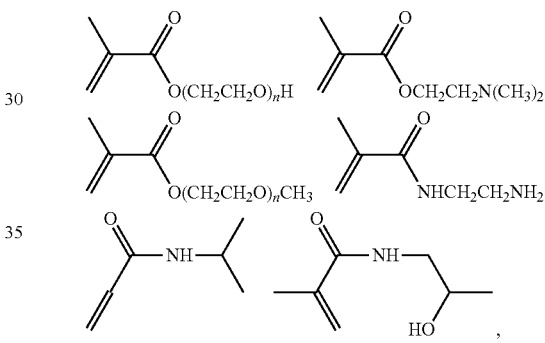

wherein each n is independently an integer from 0 to 30. In some embodiments one or more compound (B) monomers are incorporated into the random copolymer.

A random copolymer can include from about 10 to about 90% by weight of a compound (B) (e.g., from about 10 to about 85%; from about 10 to about 75%; from about 10 to about 66%; from about 10 to about 52%; from about 10 to about 46%; from about 10 to about 37%; from about 10 to about 30%; from about 10 to about 26%; from about 10 to about 13%; from about 15% to about 90%; from about 26% to about 90%; from about 32% to about 90%; from about 40% to about 90%; from about 55% to about 90%; from about 64% to about 90%; from about 77% to about 90%; from about 15 to about 85%; from about 20 to about 70%; from about 25 to about 75%; from about 35 to about 66%; and from about 40 to about 60%).

Suitable targeting groups (C) include specific and nonspecific targeting groups. For example, nonspecific targeting groups can be used to enhance nonspecific uptake the compounds through the incorporation of groups capable of interacting with the cellular membrane to enhance cellular uptake. Non-limiting examples of suitable nonspecific targeting groups include: glucose, dimethyl amine, diethyl amine, tetraalkyl ammonium salts, poly(dimethylaminoethyl methacrylate) (PDMEM) and poly(aminoethyl methacrylamide) (PAMEM).

Specific targeting groups can also be used to enhance specific cellular uptake of the polymers. Non-limiting examples of suitable specific targeting groups include polypeptides, antibodies, receptor ligands, carbohydrates, lipids, folic acid, hormones, growth factors, antigens, aptamers, chlorotoxin, and nucleic acids. For example, folic acid can facilitate specific uptake of the compound by folate receptor rich/over expressing cancer cell lines such as human cervical HeLa cells and human nasopharyngeal epidermal carcinoma KB cells. In some embodiments, use of a polypeptide can facilitate specific uptake by targeted cells. For example, cyclic (arginine-glycine-aspartic acid) (cRGD) can target uptake by $\alpha_v\beta_3$-integrin rich cancer cell lines, such as human brain glioblastoma U87-MG cells.

A targeting group compound (C) can include:

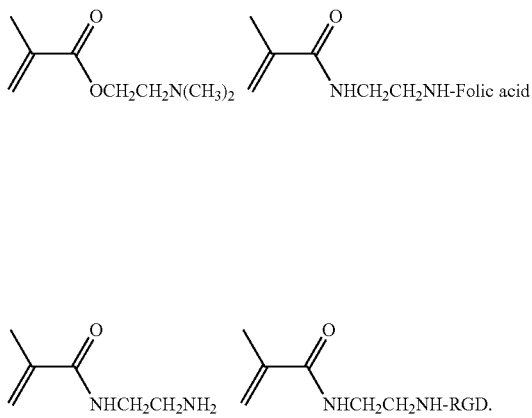

A random copolymer can include from about 10 to about 90% by weight of a compound (C) (e.g., from about 10 to about 85%; from about 10 to about 75%; from about 10 to about 66%; from about 10 to about 52%; from about 10 to about 46%; from about 10 to about 37%; from about 10 to about 30%; from about 10 to about 26%; from about 10 to about 13%; from about 15% to about 90%; from about 26% to about 90%; from about 32% to about 90%; from about 40% to about 90%; from about 55% to about 90%; from about 64% to about 90%; from about 77% to about 90%; from about 15 to about 85%; from about 20 to about 70%; from about 25 to about 75%; from about 35 to about 66%; and from about 40 to about 60%). In some embodiments one or more compound (C) monomers are incorporated into the random copolymer.

In some embodiments, the sum of A, B, and C is 100% of the weight of the random copolymer. Alternatively, in some cases, the random copolymer comprises a fluorescent oxygen sensor, a fluorescent pH sensor, or a combination thereof. For example, a random copolymer can comprise from about 0.01 to about 10% by weight of a compound (A); from about 10 to about 90% by weight of a compound (B); from about 10 to about 90% by weight of a compound (C); and from about 0.01 to about 10% by weight of a compound (D), wherein the compounds of (A), (B), and (C) are as described above, and a compound (D) is a fluorescent oxygen sensor, a fluorescent pH sensor, or a combination thereof.

Any suitable fluorescent oxygen sensor, or derivative thereof, capable of being polymerized can be used in the random polymers described herein. For example, an oxygen sensor of formula (4):

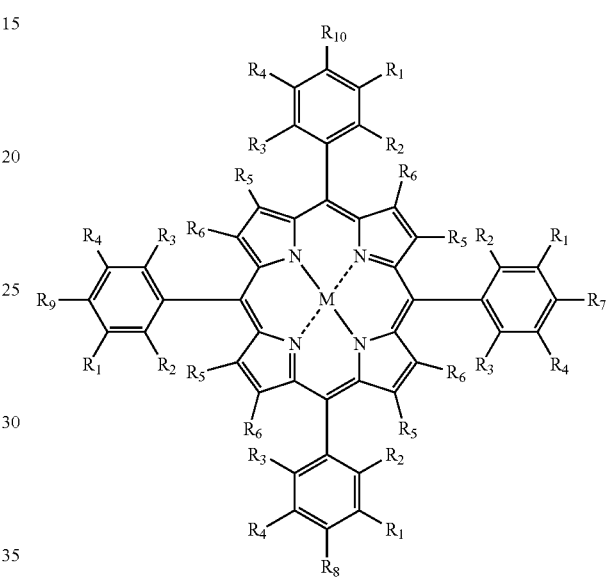

or a salt form thereof, wherein M is Pt or Pd; $R_1$, $R_2$, $R_3$, $R_4$, $R_5$, and $R_6$ are independently selected from the group consisting of: H, F, Cl, Br, I, $CH_3$, $OCH_3$, $OC_2H_5$; $R_7$, $R_8$, $R_9$, and $R_{10}$ are independently selected from the group consisting of: $(CH_2)_nOH$, $O(CH_2)_nOH$, $NH(CH_2)_nOH$, $(CH_2)_nOW$, $O(CH_2)_nOW$, $NH(CH_2)_nOW$, $(OCH_2CH_2)_nOH$, $NH(CH_2CH_2O)_nH$, $(OCH_2CH_2)_nOW$, $NH(CH_2CH_2O)_nW$; W is selected from:

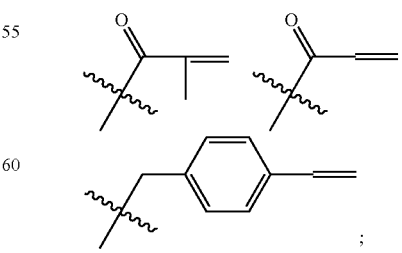

and n is an integer from 0 to 10.

A compound of formula (4) can include, for example:

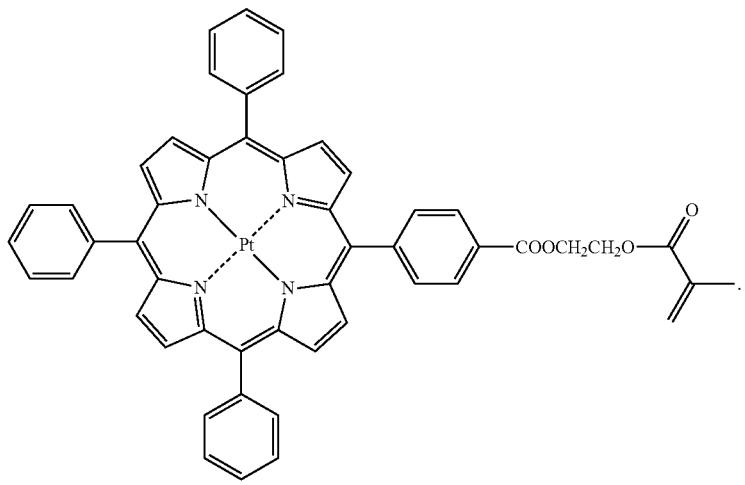

Any suitable fluorescent sensor, or derivative thereof, capable of being polymerized (e.g., having a vinyl moiety) can be used in a random copolymer as described herein. For example, the pH sensor molecules described in U.S. Pat. No. 7,390,462, which is herein incorporated by reference in its entirety.

A random copolymer can include from about 0.01 to about 10% by weight of a compound (D) (e.g., from about 0.1 to about 10%; from about 0.5 to about 10%; from about 1 to about 10%; from about 2 to about 10%; from about 4 to about 10%; from about 6 to about 10%; from about 8 to about 10%; from about 0.01 to about 8%; from about 0.01 to about 7%; from about 0.01 to about 5%; from about 0.01 to about 3%; from about 0.01 to about 1.5%; from about 0.01 to about 0.8%; from about 0.01 to about 0.4%; from about 0.01% to about 0.1%; from about 0.4% to about 4%; from about 0.75% to about 2.5%; from about 1% to about 6%; from about 3% to about 8%; and from about 2.5% to about 7.5%).

In some embodiments, the sum of A, B, C, and D is 100% of the weight of the random copolymer.

A random copolymer can be prepared through reaction of the monomers described above in the presence of any reagent which would achieve formation of a polymer. In some embodiments, two or more monomer compounds are coupled through thermal polymerization in the presence of a thermal initiator to form a polymer. Suitable thermal initiators include, for example, aliphatic azo compounds such as azobisisobutyronitrile (AIBN), 4,4-azobis(4-cyanovaleric acid), and 1,1'-azobis(cyclohexanecarbonitrile) (ABCN), and organic peroxides such as benzoyl peroxide (BPO), di-t-butylperoxide (tBuOOtBu), methyl ethyl ketone peroxide, and acetone peroxide. Alternatively, two or more monomer compounds can be coupled through photopolymerization in the presence of a photo-initiator. Suitable photo initiators include, for example, benzophenone, 2,2-dimethoxy-2-phenylacetophenone (DMPA), 2,2-dimethoxyphenylacetophenone (Irgacure 851), and bis(2,4,6-trimethylbenzoyl)-phenylphosphineoxide (Irgacure 819).

For example, all of the desired monomers (e.g., monomers of formula (1) and/or formula (2A), monomers of compound (B), monomers of compound (C), and/or monomers of compound (D)) can be polymerized in the presence of an initiator as described above in suitable solvents, such as DMF, DMSO, ethanol, THF, and toluene. In some embodiments, the polymerization is performed under inert atmospheric conditions (e.g., $N_2$ or Ar). The resulting polymers can be collected, for example, by precipitating the polymers and further purification (e.g., by fraction and dialysis) can be performed as needed.

In some embodiments, the random copolymer may be formed into a polymer thin film. The polymer thin film can have a thickness ranging from about 0.1 to about 100 μm (e.g., from about 0.5 to about 100 μM; from about 1 to about 100 μm; from about 10 to about 100 μm; from about 25 to about 100 μm; from about 40 to about 100 μm; from about 55 to about 100 μm; from about 65 to about 100 μm; from about 80 to about 100 μm; from about 0.1 to about 90 μm; from about 0.1 to about 75 μm; from about 0.1 to about 60 μm; from about 0.1 to about 40 μm; from about 0.1 to about 15 μm; from about 0.1 to about 5 μm; from about 0.1 to about 1 μm; from about 5 to about 75 μm; from about 10 to about 80 μm; from about 15 to about 65 μm; and from about 25 to about 50

In some cases, the random copolymer thin film may be formed on a substrate, for example, glass, a transparent polymer, or a transparent copolymer polymeric mixture. Suitable substrates include, for example, plasticized or non-plasticized poly(vinyl chloride) (PVC), sol-gel materials, polyvinylformal-silica mixtures, hydrogels, polyurethanes, poly(2-hydroxyethyl methacrylate), polyacrylamide, polydimethylsiloxane, polyethylene terephthalate, polystyrene, and mixtures thereof. In some embodiments, the substrate is an organic or inorganic glass, for example, quartz glass. Alternatively, the substrate can be an optic fiber bundle.

A polymer or random copolymer having one or more terminal amine moieties can be postfunctionalized with a targeting group. Suitable targeting groups (C) include specific and nonspecific targeting groups. For example, nonspecific targeting groups can be used to enhance nonspecific uptake the polymer through the incorporation of groups capable of interacting with the cellular membrane to enhance cellular uptake. Non-limiting examples of suitable nonspecific targeting groups include: glucose, dimethyl amine, diethyl amine, poly(dimethylaminoethyl methacrylate) (PDMEM) and poly(aminoethyl methacrylamide) (PAMEM).

Specific targeting groups can also be used to enhance specific cellular uptake of the polymers. Non-limiting examples of suitable specific targeting groups include polypeptides, antibodies, receptor ligands, carbohydrates, lipids, folic acid, hormones, growth factors, antigens, aptamers, chlorotoxin, and nucleic acids. For example, folic acid can facilitate specific uptake of the compound by folate receptor rich/over expressing cancer cell lines such as human cervical HeLa cells and human nasopharyngeal epidermal carcinoma KB cells. In some embodiments, use of a polypeptide can facilitate specific uptake by targeted cells. For example, cyclic (arginine-glycine-aspartic acid) (cRGD) can target uptake by $\alpha_v\beta_3$-integrin rich cancer cell lines, such as human brain glioblastoma U87-MG cells.

Nanoparticles

Provided herein are nanoparticles comprising one or more polymerized monomer compounds of formula (1) or (2A) as described above. In some embodiments, a nanoparticle can be prepared as a random copolymer as described above.

A nanoparticle, as described herein, can be prepared using methods known to those of skill in the art. For example, a nanoparticle can be prepared through emulsion polymerization. In some embodiments, a nanoparticle can be prepared by combining all desired monomers (e.g., monomers of formula (1) and/or formula (2A), monomers of compound (B), monomers of compound (C), and/or monomers of compound (D)) in water with a suitable surfactant and a suitable initiator. Suitable surfactants can include, for example, fatty acids, sodium dodecyl sulfate (SDS), and alpha olefin sulfonate. In some embodiments, a surfactant can be chosen from Tween 20 and SDS. Suitable initiators include, for example, aliphatic azo compounds such as 4,4-azobis(4-cyanovaleric acid), azobisisobutyronitrile (AIBN) and 1,1'-azobis(cyclohexanecarbonitrile) (ABCN), and peroxides such as benzoyl peroxide (BPO), di-t-butylperoxide (tBuOOtBu), methyl ethyl ketone peroxide, lauroyl peroxide, acetone peroxide and hydroperoxide. In some embodiments, the nanoparticle is prepared under inert atmospheric conditions (e.g., $N_2$ or Ar). Nanoparticles can be purified following polymerization, for example by dialysis.

Nanoparticles may have a diameter from about 1 nm to about 300 nm (e.g., from about 1 nm to about 250 nm, from about 1 nm to about 200 nm, from about 1 nm to about 150 nm, from about 1 nm to about 125 nm, from about 1 nm to about 100 nm, from about 1 nm to about 75 nm, from about 1 nm to about 60 nm, from about 1 nm to about 45 nm, from about 1 nm to about 25 nm, from about 1 nm to about 10 nm, from about 5 nm to about 300 nm, from about 25 nm to about 300 nm, from about 50 nm to about 300 nm, from about 75 nm to about 300 nm, from about 100 nm to about 300 nm, from about 125 nm to about 300 nm, from about 140 nm to about 400 nm, from about 200 nm to about 300 nm, from about 25 to about 150 nm, from about 50 to about 125 nm, from about 75 to about 125 nm, from about 80 to about 120 nm, and from about 90 to about 110 nm). In some embodiments, the nanoparticles have a diameter less than about 100 nm. The sizes of the nanoparticles can be characterized using, for example, dynamic light scattering (DLS), atomic force microscopy (AFM), scanning electron microscopy (SEM), or transmission electron microscopy (TEM).

A nanoparticle having one or more terminal amine moieties can be postfunctionalized with a targeting group. Suitable targeting groups (C) include specific and nonspecific targeting groups. For example, nonspecific targeting groups can be used to enhance nonspecific uptake the compounds through the incorporation of groups capable of interacting with the cellular membrane to enhance cellular uptake. Non-limiting examples of suitable nonspecific targeting groups include: poly(dimethylaminoethyl methacrylate) (PDMEM) and poly(aminoethyl methacrylamide) (PAMEM).

Specific targeting groups can also be used to enhance specific cellular uptake of the nanoparticles. Non-limiting examples of suitable specific targeting groups include polypeptides, antibodies, receptor ligands, carbohydrates, lipids, folic acid, hormones, growth factors, antigens, aptamers, chlorotoxin, and nucleic acids. For example, folic acid can facilitate specific uptake of the nanoparticles by folate receptor rich/over expressing cancer cell lines such as human cervical HeLa cells and human nasopharyngeal epidermal carcinoma KB cells. In some embodiments, use of a polypeptide can facilitate specific uptake by targeted cells. For example, cyclic(arginine-glycine-aspartic acid) (cRGD) can target uptake by $\alpha_v\beta_3$-integrin rich cancer cell lines, such as human brain glioblastoma U87-MG cells.

Sensing Film for Extracellular Detection of Ions

Further provided herein are sensing films comprising a substrate covalently bound to a compound of formula (1) or (2A). In some embodiments, the substrate is covalently bound to the compound through a linker A linker can be any suitable organic group which serves to space the substrate from the compound so as to enable the sensing film to be chemically immobilized on the substrates, maximize sensing sensitivity or signal intensity. For example, a linker can include one or more of a $C_{1-20}$ alkyl, $C_{1-20}$ alkoxy, amino, silane, maleimide, and thiol moiety. The linker may also include a polyethylene glycol (PEG) linker. In some embodiments, the linker can include a vinyl, acrylate, or methacrylate moiety to facilitate polymerization of the compound of formula (1) or (2A) to the linker Examples of such linkers are well known to those skilled in the art.

A substrate can be any substrate suitable for the preparation of sensing membranes. For example, a substrate can include glass, a transparent polymer, or a transparent copolymer polymeric mixture. Suitable substrates also include, for example, plasticized or non-plasticized poly(vinyl chloride) (PVC), sol-gel materials, polyvinylformal-silica mixtures, hydrogels, polyurethanes, poly(2-hydroxyethyl methacrylate), polyacrylamide, polydimethylsiloxane, polyethylene terephthalate, polystyrene, and mixtures thereof. In some embodiments, the substrate is an organic or inorganic glass, for example, quartz glass. Alternatively, the substrate can be an optic fiber bundle.

In some embodiments, a crosslinker comprises at least two of the following: a vinyl, acrylate, methacrylate, acrylamide, and methacrylamide functional group. For example, the crosslinkers can include poly(ethylene glycol) dimethacrylate, ethoxylated trimethylolpropane triacrylate (SR454), and bio(ethylamine)acryamide. In some embodiments, the sensors were copolymerized into suitable matrices. For example, an ion permeable matrix such as poly(2-hydroxyethyl methacrylate), poly(acrylamide), poly[(ethylene glycol) methacrylate] can be used.

Figure 16:
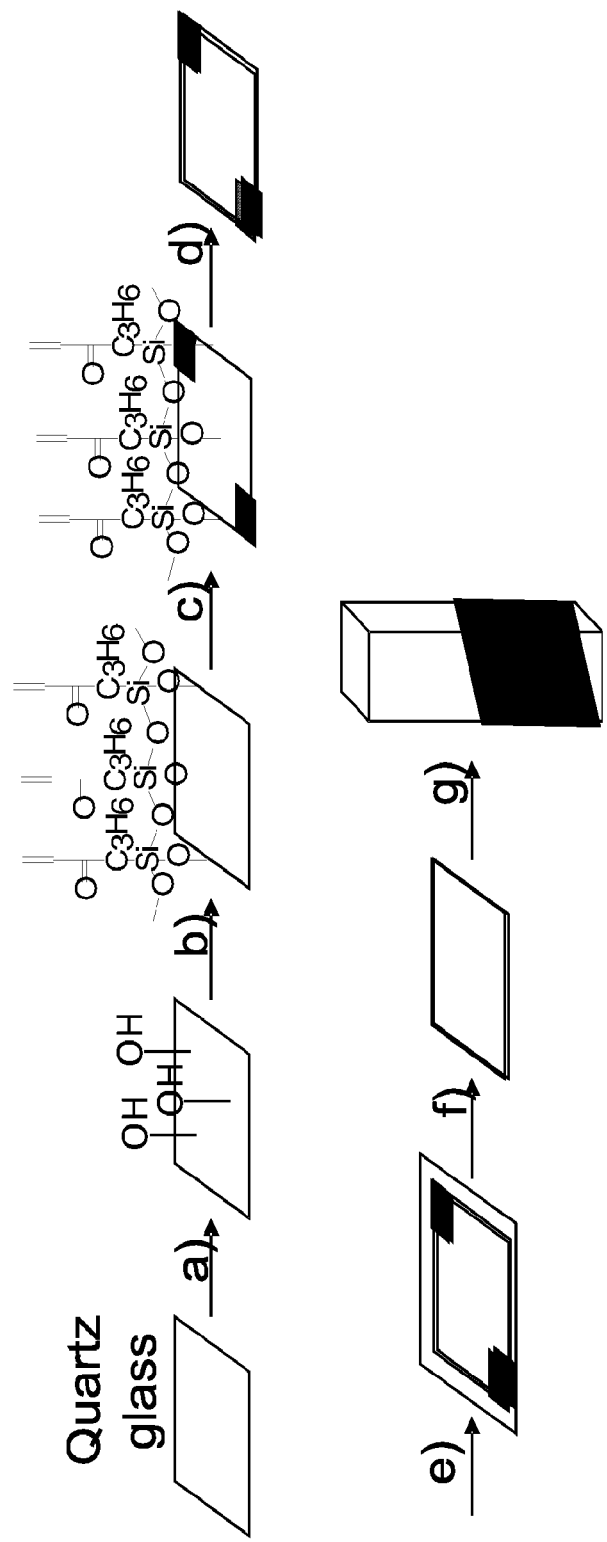
FIG. 16 is a schematic illustration of the preparation of sensing membranes. a) oxygen plasma treatment to generate active hydroxyl groups; b) vapor deposition of thin TMSPA layer; c) 25-mm tape used to control membrane thickness; d) sensor solution dispensed onto modified quartz surface; e) solution covered with a cover glass and polymerized at 80° C. for 1.5 hours; f) cover glass and tape removed; film rinsed using methanol and double-distilled water; and g) sensing membrane on quartz substrate immersed into liquid in cuvette for fluorescence measurements.

A sensing film as described herein can be prepared, for example, as shown in FIGS. 1 and 16. In particular, the sensing film can be prepared by reacting a compound of formula (1) or (2A) with an initiator in the presence of matrix monomers such as the 2-hydroxyethyl methacrylate, acrylamide and a crosslinker in a solvent (e.g., DMF), or a functionalized substrate (e.g., an acrylate-moiety functionalized quartz glass). Polymerization can be carried out under inert atmosphere and at elevated temperature. The sensing film prepared can then be purified as needed to remove any non-polymerized monomers or residual solvent.

Fluorescence Assays

Fluorescence of a sensor (e.g., compound, polymer, nanoparticle, and sensing film) as described herein may be detected by any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor (e.g., filters, diffraction gratings, and dichroic mirrors). Examples of suitable devices include fluorimeters, spectrofluorimeters and fluorescence microscopes. Many such devices are commercially available from companies such as Hitachi, Nikon, Molecular Dynamics or Zeiss. In some embodiments, the device is coupled to a signal amplifier and a computer for data processing.

In general, assays using a sensor as provided herein involve contacting a sample with such a sensor and measuring fluorescence. For example, methods are provided for measuring the concentration of potassium ions in a sample. In some cases, the concentration of oxygen and hydronium ions (pH) may also be determined. The presence of an analyte (e.g., potassium ion, oxygen, or hydronium ion) that interacts with the sensor may alter fluorescence of the sensor in many different ways. Essentially any change in fluorescence caused by the analyte, typically the potassium ion, may be used to determine the presence of the ion and, optionally, the concentration of the ion in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the sensor to fluoresce. To determine the excitation spectrum for a sensor in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by ion in a sample may be used as the basis for determining the presence, and optionally, the concentration of ion in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength, emission intensity, or the shape of the profile that are caused by the presence of an in a sample may be used to determine the presence or concentration of the ion in the sample. Changes in excitation or emission spectra may be measured as ratios of two wavelengths. A range of changes are possible, from about a few nm to 5, 10, 15, 25, 50, 75, 100, or more nm Quantum yield may be obtained by comparison of the integrated area of the connected emission spectrum of the sample with that of a reference solution. A preferred reference solution is a solution of fluorescein in 0.1 N NaOH, quantum efficiency 0.95. The concentration of the reference is adjusted to match the absorbance of the test sample. The quantum yields may be calculated using equations known to those of skill in the art.

A change in quantum yield caused by an ion may be used as the basis for detecting the presence of the ion in a sample and may optionally be used to determine the concentration of the ion. A range of changes are possible. For example, the difference in the quantum yield for a subject sensor in the presence of a ion may be about 10%, 25%, 50%, 75% the quantum yield, or it may be 2, 3, 5, 10, 100, 200, 1000, or 10000 times greater or more. The same values may be used to describe changes observed in intensity in such the subject assays.

It is expected that some samples will contain compounds that compete with the sensor for the ion. In such cases, the fluorescence measurement will reflect this competition. In one variation, the fluorescence may be used to determine the presence or concentration of one or more such ion-competing compounds in a sample. In the case of potassium ion sensing, sodium ions are a common interfering ion for fluorescence measurements. The fluorescent sensing moieties provided herein, however, are largely unaffected by changes in pH and sodium ion concentration.

In some embodiments, the presence of potassium ion in a sample is detected by contacting the sample with a sensor as described herein. The fluorescence of the solution is then determined using one of the above-described devices, for example, a spectrofluorometer. Optionally, the fluorescence of the solution may be compared against a set of standard solutions containing known quantities of the ion, e.g., potassium. Comparison to standards may be used to calculate the concentration of the ion in the sample.

The analyte may be any described above (e.g., potassium ion, oxygen, or hydronium ion). The concentration of the analyte may change over time and the fluorescent signal of the sensor may serve to monitor those changes. For example, the particular form of the potassium ion that interacts with the sensor may be produced or consumed by a reaction occurring in the solution, in which case the fluorescence signal may be used to monitor reaction kinetics.

In some embodiments, a sensor as provided herein can be used to determine and quantitate the antibacterial qualities of a compound. Antibacterial compounds can stimulate a K+ efflux from the bacteria, which can be monitored through time dependent fluorescence intensity changes of the sensor. For example, a solution of a particular bacterium can be prepared in a medium (e.g., NaCl) in the presence of one or more sensing compounds. Upon addition of a candidate antibacterial compound, any K+ releasing from the bacteria into solution can be monitored through an increase in the fluorescence intensity of the sensor. The rate of K+ efflux can be used to observe and quantitate the antibacterial properties of the compound against the particular bacterium. See, for example, Example 23.

In certain embodiments, the sample is a biological fluid, lysate, homogenate or extract. The sample may contain one or more cells. Samples may have a pH of about 5, 6, 7, 8, 9, 10, 11, 12, or higher.

In another variation, the presence of an ion in a biological sample may be determined using a fluorescence microscope and one or more sensors described herein. The biological sample is contacted with the sensor and fluorescence is visualized using appropriate magnification, excitation wavelengths, and emission wavelengths. In order to observe co-localization of multiple analytes, the sample may be contacted with multiple sensors simultaneously. In certain embodiments the multiple sensors differ in their emission and/or excitation wavelengths.

Biological samples may include bacterial or eukaryotic cells, tissue samples, lysates, or fluids from a living organism. In certain embodiments, the eukaryotic cells are cancer cells, for example, folate receptor rich/over expressing cancer cell lines such as human cervical HeLa cells and human nasopharyngeal epidermal carcinoma KB cells, or $\alpha_v\beta_3$-integrin rich cancer cell lines, such as human brain glioblastoma U87-MG cells.

Detection of an ion in a cell may include detection of the ion in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices. In some embodiments, the sensors used for intracellular detection can include a compound of formula (1), (2A) or (3), polymers, random copolymers, or nanoparticles as described herein. Such intracellular measurements may be obtained by contacting the cell with a sensor as described above. In some embodiments, the sensor is contacted with the cell using microinjection.

Target compounds, polymers, and nanoparticles as described above may also be used to image a targeted cell in a patient. For example, the patient can be administered an effective amount of the desired targeted compound and imaged using suitable fluorescence techniques. Any cancer cell can be imaged if an appropriate targeting moiety is used. For example, folate receptor rich/over expressing cancer cell lines such as human cervical HeLa cells and human nasopharyngeal epidermal carcinoma KB cells can be imaged using a folic acid targeting group, or $\alpha_v\beta_3$-integrin rich cancer cell lines, such as human brain glioblastoma U87-MG cells can be imaged using a cRGD targeting group. Suitable fluorescence techniques for in vivo imaging can include a Xeneogen IVIS-200 System. Typically, such imaging will involve excitation of the fluorescent sensor using wavelengths of about 488 nm or longer to provide an emission spectrum in the green and red windows.

Detection of an ion in a fluid sample, for example, in the extracellular matrix of a biological sample, can be performed using an extracellular sensor such as those described above, or a compound of formula (2), such as:

and

-continued

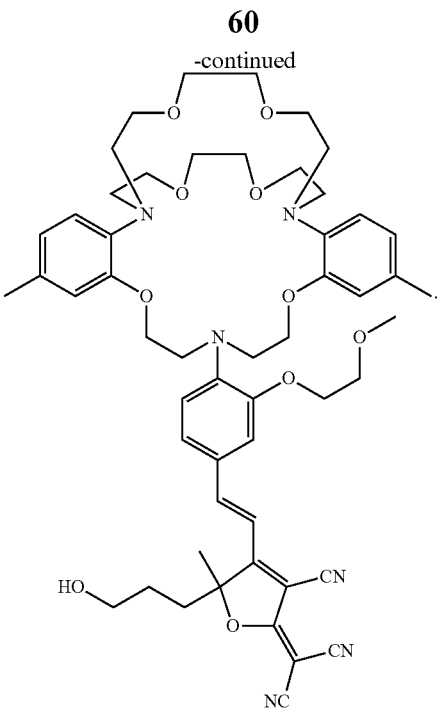

Pharmaceutical Formulations and Dosage Forms

When employed as pharmaceuticals, the compounds, polymers, and nanoparticles described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump.

This invention also includes pharmaceutical compositions which contain, as the active ingredient, a compound, polymer, or nanoparticle of the invention or a pharmaceutically acceptable salt thereof, in combination with one or more pharmaceutically acceptable carriers (excipients). When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatin capsules, suppositories, and sterile injectable solutions.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds, polymers, and nanoparticles described herein may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the area being imaged as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

EXAMPLES

General Methods

An amino-substituted triazacryptand ionophore (TAC-NH2) and an acetate-substituted triazacryptand ionophore (TAC-CHO), N-2-propenyl-4-bromo-naphthalimide (compound 1), and 2-dicyanomethylene-3-cyano-4,5,5-trimethyl-2,5-dihydrofuran (TCF) were synthesized according to known procedures (He, H. et al., *J. Am. Chem. Soc.* 2003, 125, 1468-1469; Konstantinova T. N. et al., *J Appl Polym Sci* 2009; 111:1991-1998; and Gopalan, P. et al., *J. Am. Chem. Soc.* 2004, 126, 1741-1747). Lysosensor SM3 was prepared according to our published procedure (Tian, Y. et al., *Biomaterials* 2010, 31, 7411-7422). HEMA, AM, METAC, trimethylsilylpropyl acrylate (TMSPA), azobisisobutyronitrile (AIBN), N,N-diisopropylethylamine (DIPEA), N-methyl-2-pyrrolidone (NMP), amphotericin, KCl, NaCl, $CaCl_2$, $MgCl_2$, $FeCl_3$, $ZnCl_2$, $CuCl_2$, 4-(2-hydroxyethyl)-1-piperazineethanesulfonic acid (HEPES), nigericin, bumetanide, and ouabain were purchased from Sigma-Aldrich (St. Louis, Mo.). Hoechst 33342, PBFI, and MitroTracker® Green FM were ordered from Invitrogen (Carlsbad, Calif.).

A Varian liquid-state NMR operated at 400 MHz for $^1H$ NMR and at 100 MHz for $^{13}C$ NMR was used for NMR spectra measurements. High resolution mass spectrometry (HRMS) was performed by the ASU Mass Spectrometry Laboratory. A Shimadzu UV-3600 UV-Vis-NIR spectrophotometer (Shimadzu Scientific Instruments, Columbia, Md.) was used for absorption spectra measurements. A Shimadzu RF-5301 spetrofluorophotometer was used for fluorescence measurements.

Example 1

Method of Synthesis of a Compound of Formula (1)

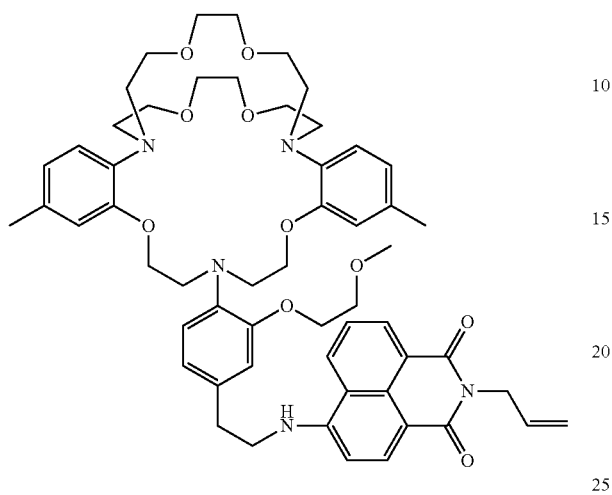

100 mg (138.53 μmol) of amine (compound I), 47.19 mg (149.27 μmol) of compound II, and 21.05 mg of N,N-diisopropylethylamine (DIPEA) were suspended in 1 mL N-methyl-2-pyrrolidone (NMP) and microwaved to 150° C. for 4 h. The mixture was poured into 10 mL water. The resulting precipitate was filtered and washed with 10 mL water. The crude product was then purified with silica gel column using chloromethane/methanol to afford 36 mg (27.3%) of the desired compound as a yellow gum.

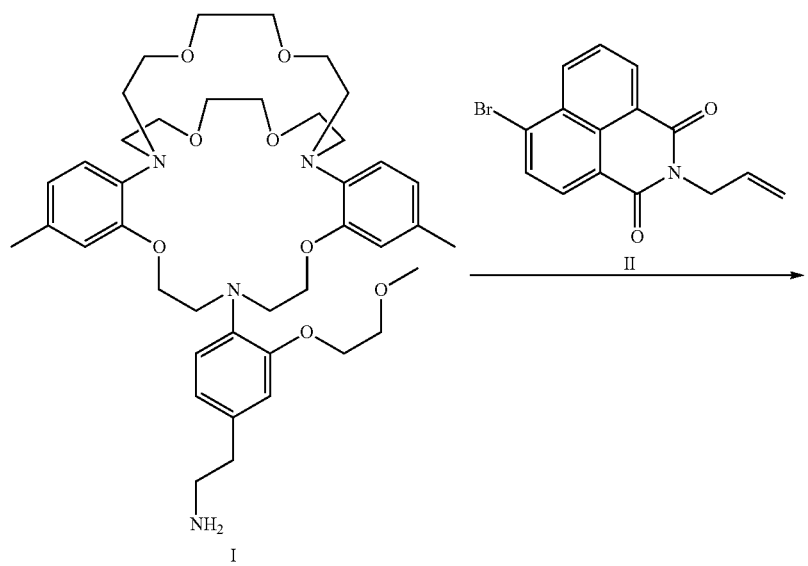

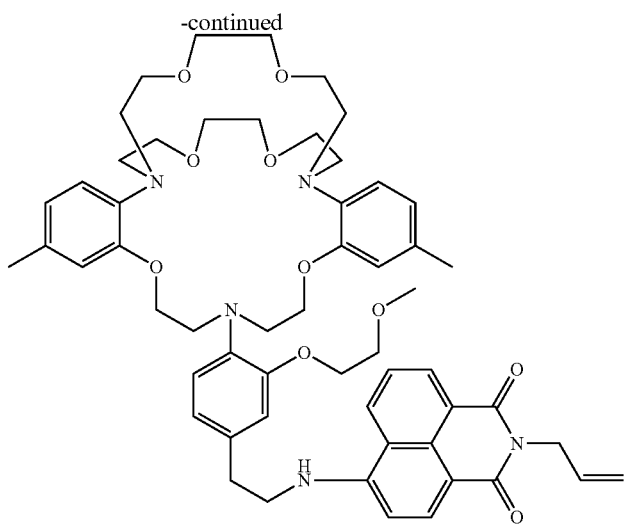

Example 2

A Method of Synthesis of a Compound of Formula (2)

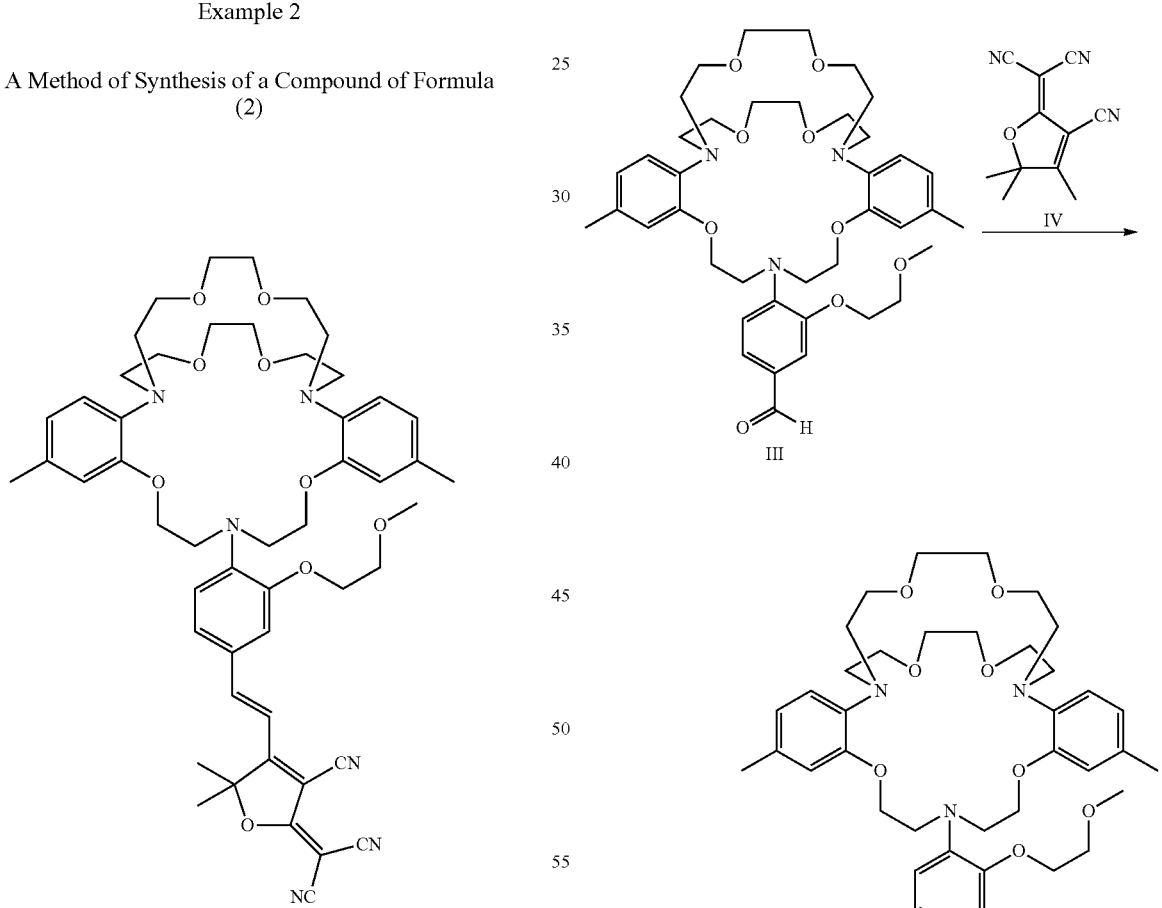

100 mg (138.53 μmol of aldehyde (compound III; TAC-CHO), 2-dicyanomethylene-3-cyano-4,5,5-trimethyl-2,5-dihydrofuran (33.12 mg, 166.23 μmol; compound IV) and ammonium acetate (10.7 mg, 138.53 mmol) were dissolved in a mixture of 1 mL of THF and 5 mL of ethanol. The mixture was stirred for 8 h at room temperature. The products were collected by filtration and washed with ethanol and diethyl ether to obtain 71.2 mg of a red color compound. Yield: 56.9%.

Example 3

General Method of Preparation of Random Copolymers

The desired monomers (including monomeric compounds of formula (1) and (2A), monomers of compounds (D), monomers of compound (B, and monomers of compound (C) with controlled molar or weight ratios) and initiator (e.g., AIBN) will be dissolved in suitable solvent (e.g., DMF, DMSO, ethanol, or water). The mixture will be degassed a few times and filled with nitrogen. The polymerization will be carried out under the nitrogen condition and at 65° C. for a time sufficient to complete polymerization (e.g., 24 hours). After polymerization, the polymer can be precipitated from the reaction mixture. The polymers can be further purified using dialysis approach.

Example 4

General Methods for the Preparation of Nanoparticles

The desired monomers (including monomeric compounds of formula (1) and (2A), monomers of compounds (D), monomers of compound (B, and monomers of compound (C) with controlled molar or weight ratios) and initiator (e.g., AIBN) will be suspended in water with a suitable surfactant (e.g., Tween 20 or SDS). After degassing using nitrogen flow, the polymerization will be carried out under the nitrogen condition and at 65° C. for a time sufficient to complete the polymerization (e.g., 24 hours). After polymerization, the formed nanoparticles will be purified using dialysis. The sizes of the nanoparticles will be characterized using dynamic light scattering (DLS) atomic force microscopy (AFM), scanning electron microscopy (SEM), or transmission electron microscopy (TEM).

Example 5

General Methods for the Preparation of Sensing Membranes for Extracellular Potassium Ion Sensing Sensing films can be prepared either through thermal polymerization (using 4,4-azobis(4-cyanovaleric acid), azobisisobutyronitrile (AIBN) or benzoyl peroxide (BPO) as the thermal initiators) or using a photoinitiator, such as Benzophenone, Irgacure 851 (2,2-dimethoxyphenylacetophenone), or Irgacure 819 (bis(2,4,6-trimethylbenzoyl)-phenylphosphineoxide). A sensor as prepared in Example 1, a thermal polymerization initiator, and comonomers with a crosslinker for the matrix were dissolved in N,N'-dimethyl formamide (DMF). The DMF solution was added onto an acrylate-moiety functionalized quartz glass and the solution was covered with a clean cover slip (untreated) to form a sandwich structure. Film thickness was controlled using a Kapton-type electric tape (typically 25 nm thick, DuPont, Wilmington, Del.). This was placed in a vacuum oven, which was then evacuated and refilled with nitrogen three times. Polymerization was carried out under nitrogen at 80° C. for 1.5 hours. The quartz glass with a polymer film was removed from the oven, and the tape and cover slip were removed. The uniform polymer film on the quartz glass was then washed three times with methanol, followed by three times with double-distilled water, to remove any non-polymerized monomers and the residual DMF. The films were dried and stored in the dark at room temperature.

This method was also used to prepare a dual sensing film for potassium ion and oxygen sensing. The above procedure was followed, except two sensing monomers, the potassium monomer from Example 1 and an oxygen monomer having the structure:

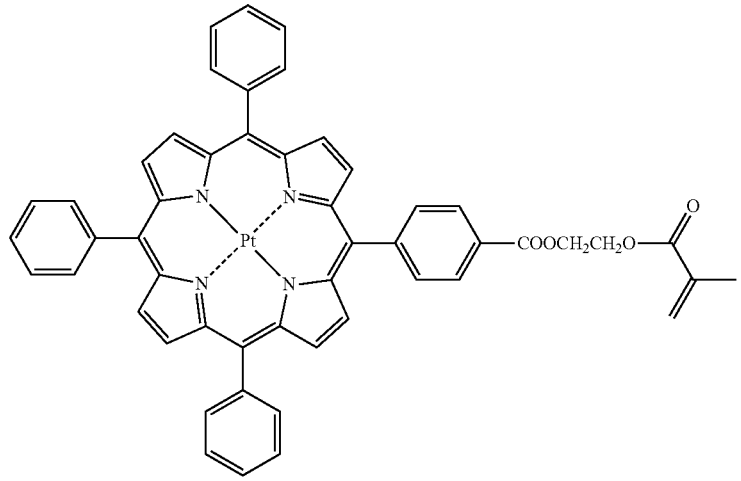

were used simultaneously.

Example 6

Measuring Sensor Response in Aqueous Solution

Figure 2:
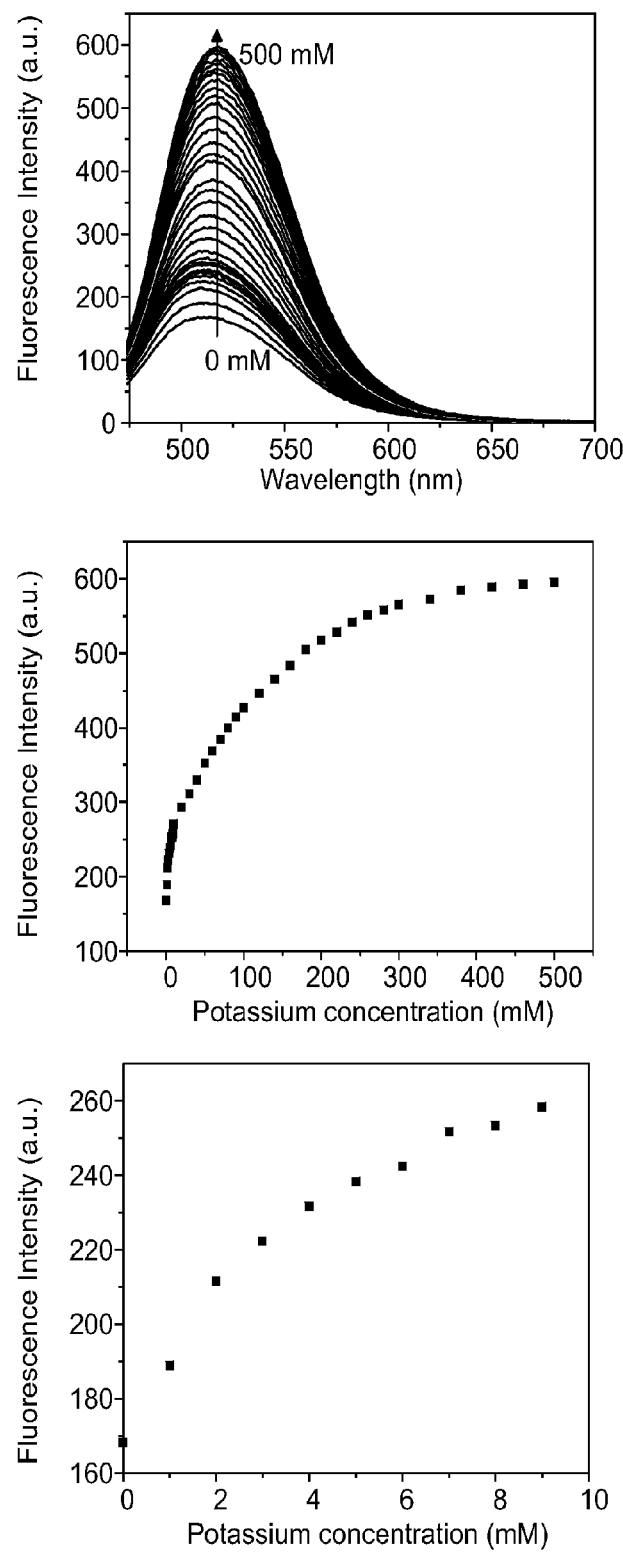
FIG. 2 illustrates the potassium ion response for a sensor of Example 1 for intracellular potassium ion sensing.
Figure 3:
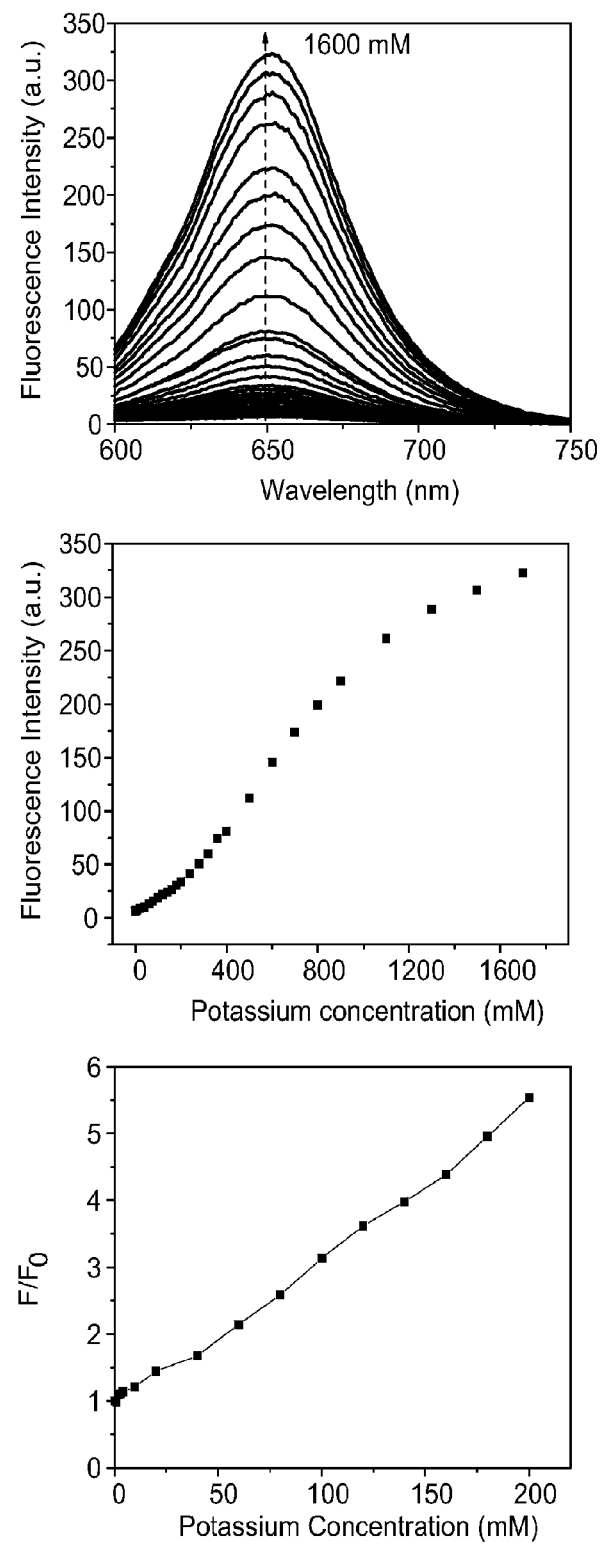
FIG. 3 illustrates the potassium ion response of a sensor of Example 2 for intracellular potassium ion sensing.

A solution of a sensor of Example 1 and Example 2 was prepared at a concentration of 5 µmol/L in HEPES (4-(2-hydroxyethyl)-1-piperazineethanesulfonic acid) buffer was titrated with various potassium ion concentrations. Sensors of Example 1 were excited at 450 nm to generate its green emission (FIG. 2), and collected from 470 nm to 650 nm with a maximum at 520 nm. Sensors of Example 2 were excited at 488 nm to generate its red emission (FIG. 3) collected from 550 nm to 750 nm with a maximum at 650 nm. The response for each sensor is shown in FIGS. 2 and 3.

Example 7

Intracellular Potassium Ion Sensing

Figure 4:
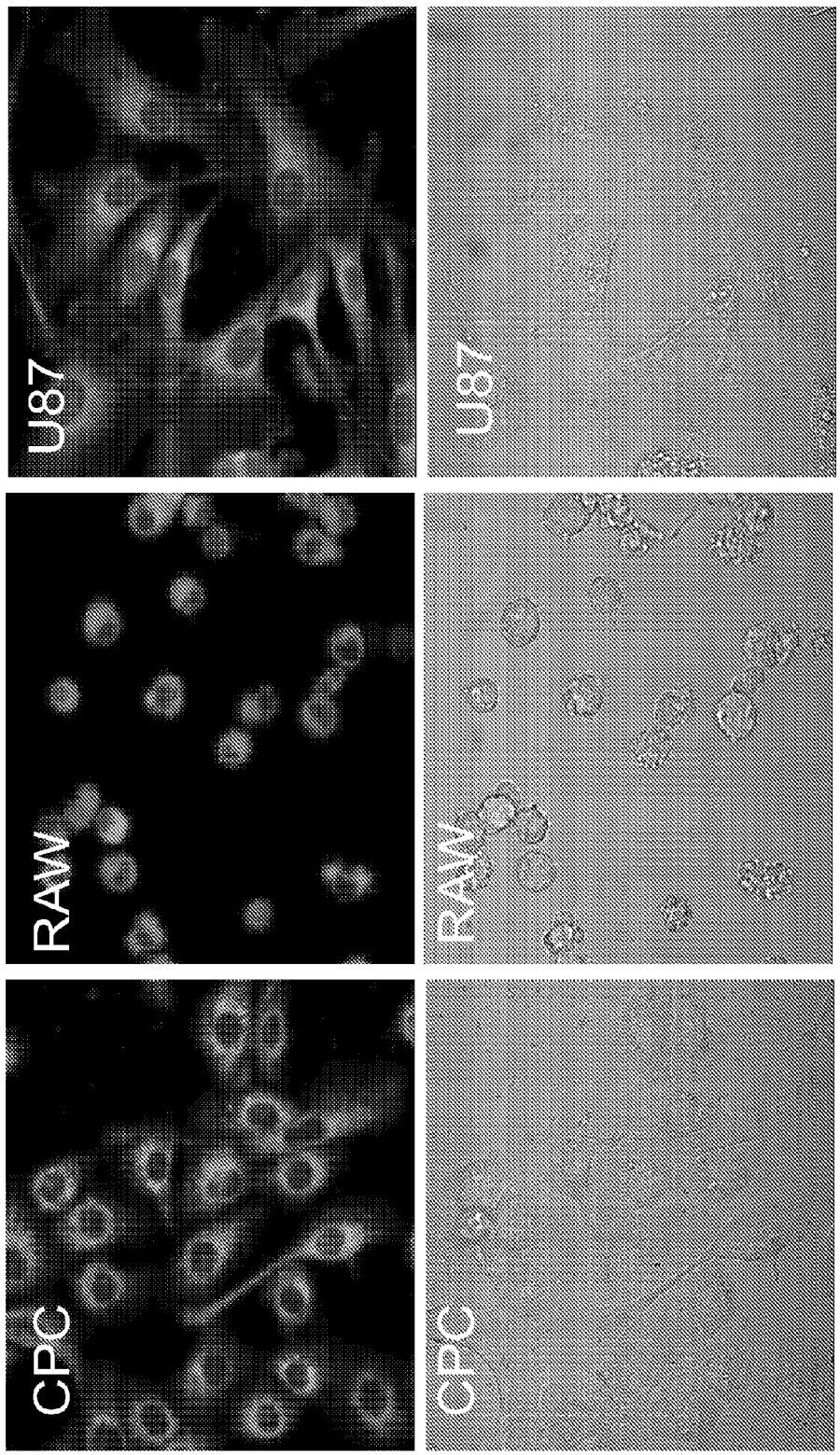
FIG. 4 shows the fluorescent imaging of cells using a sensor of Example 1.
Figure 5:
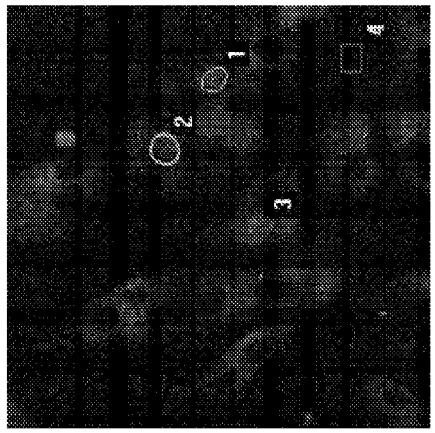
FIG. 5 shows the fluorescent imaging of cells using a sensor of Example 2.
Figure 5:
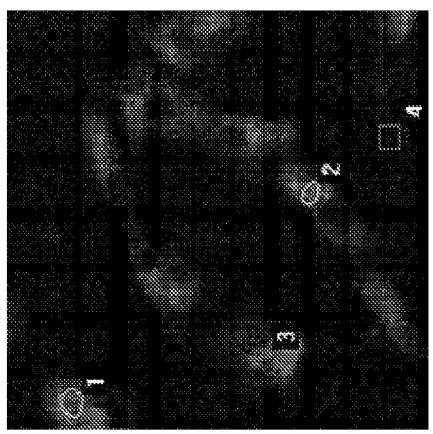
Figure 5:
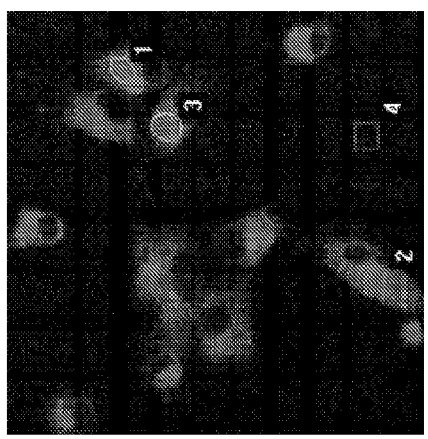
Figure 5:
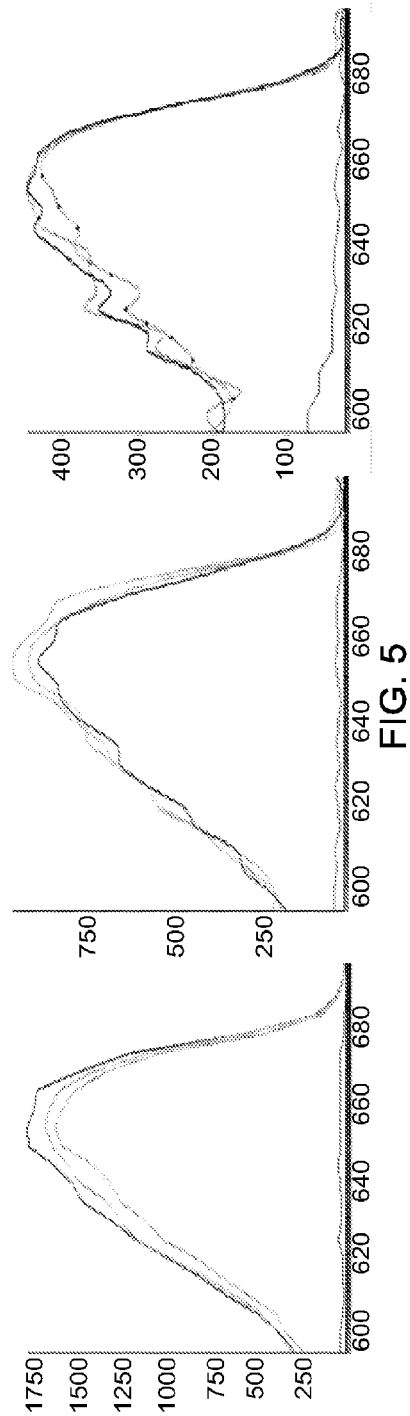

Human glioblastoma U87-MG cells, Barrett's esophagus precancer small cell lung cancer (CPC) cells, and mouse macrophage RAW 264.7 cells were used to test the subcellular distributions of the potassium ion sensors of Example 1 and 2. After cells were cultured in 96 wells at 10,000 cells/well for 24 hours, the sensors (5 µmole/L) were dissolved in DMSO and added into the cell culture medium. After a 30 minute incubation, the subcellular distribution of the sensors was studied by using confocal fluorescence microscopy. Sensors were excited at 405 nm and typical emissions were collected from 515±15 nm for green emission and 605±37.5 nm for red emission. The fluorescent images are shown in FIGS. 4 and 5.

Example 8

Measuring Extracellular Sensing Response in Sensor Films

Figure 6:
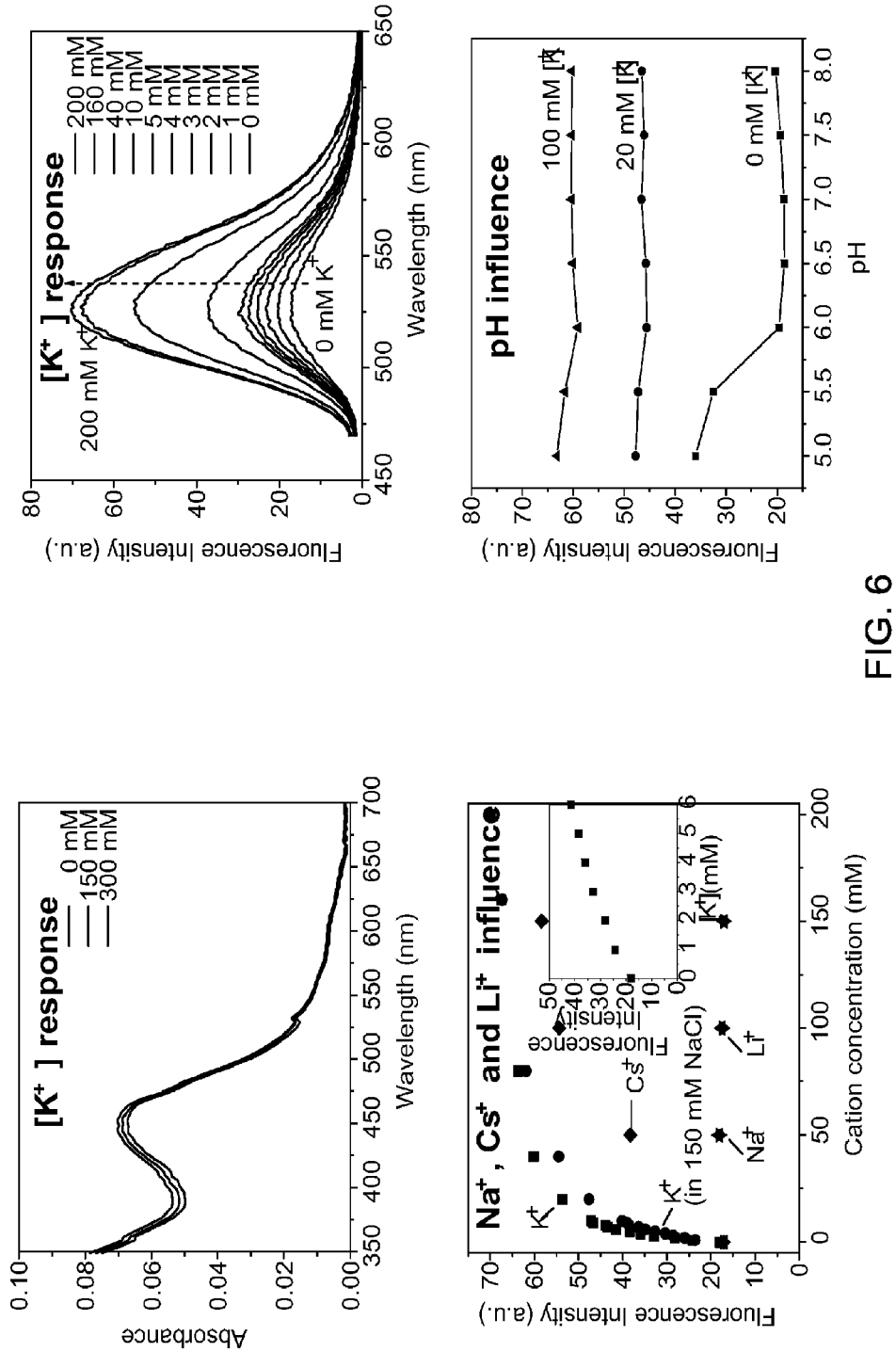
FIG. 6 shows the extracellular potassium sensing of a sensor film having polymerized monomers of a sensor of Example 1.

The potassium ion sensing film prepared in Example 5 was immersed in a buffer and the emissions of the film were monitored upon the change of potassium ion concentration. Sensors were excited at 450 nm and typical emissions were collected from 470 nm to 650 nm for the green emission. The response of the film to varied concentrations of potassium, sodium, and pH is shown in FIG. 6. As can be seen by the figure, the sensing film is specific for potassium and measures little interference from sodium, lithium, and cesium ion also present in solution. In addition, the sensing film is unaffected by changes in pH.

Example 9

Measuring Oxygen and Potassium Ion Response in a Dual Sensing Film

A dual potassium and oxygen sensing film was prepared as described in Example 5. The sensing film was placed diagonally into quartz cuvettes containing buffers or cell culture medium. The sensors were excited at 440 nm to generate the green emission from the potassium ion sensor and the red emission of the oxygen sensor. Oxygen concentration was adjusted by bubbling a nitrogen/oxygen gas mixture into the liquid contained in the cuvette. After the saturation of the liquid using the gas mixture with defined oxygen concentration, the emission spectra were taken. Potassium ion concentration in the solution was adjusted by tuning the concentrations of potassium chloride to measure the responses of the dual sensor film.

Figure 7:
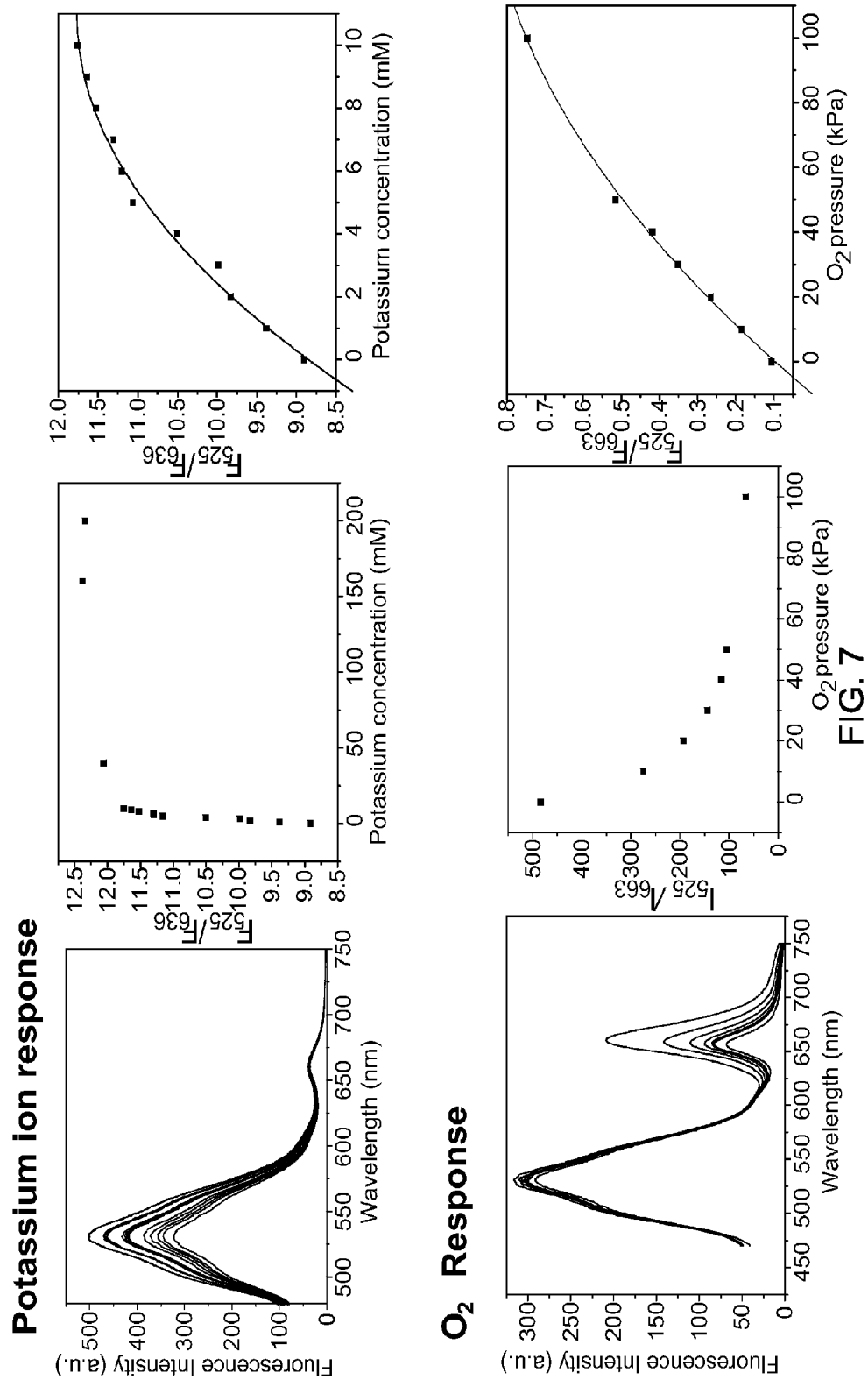
FIG. 7 shows the detection of potassium and oxygen in a dual sensor film.

As shown in FIG. 7, no interference was observed between the potassium and oxygen sensors. Both sensors were able to detect and quantitatively measure their respective ions.

Example 10

A Method of Synthesis of a Compound of Formula (2): (2a)

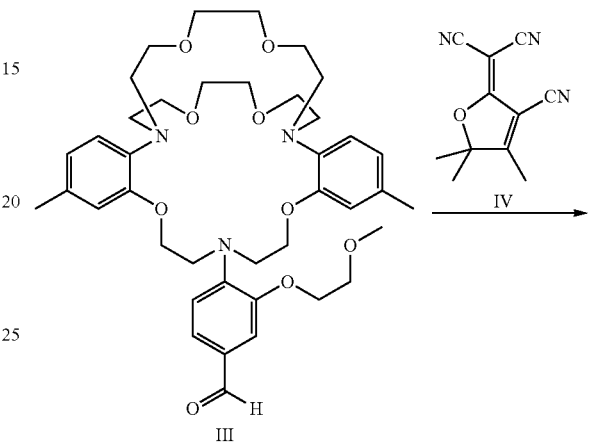

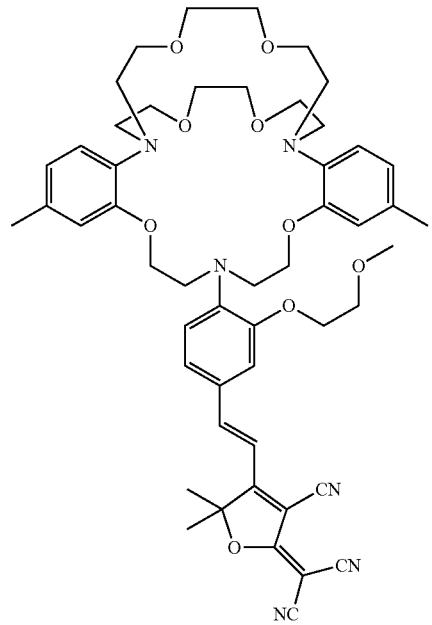

In a round-bottom flask fitted with a reflux condenser, TAC-CHO (compound III; 100 mg, 138.5 µmol), and 2-dicyanomethylene-3-cyano-4,5,5-trimethyl-2,5-dihydrofuran (TCF; compound IV; 33.12 mg, 166.2 µmol) were dissolved in 2 mL of absolute ethanol. NaOH (2 mg) was added to this mixture and refluxed for 12 hrs. The deep violet solution was extracted with dichloromethane from water, and the organic layer was dried with $MgSO_4$. The crude product was purified by column chromatography over silica gel to get a dark-purple solid (62 mg, yield: 49.6%).

Example 11

Measuring Quantum Efficiency and Sensor Responses

The fluorescence quantum yields (η) of samples in solutions were recorded by using Rhodamine B in ethanol (η=0.65) excited at 540 nm and were calculated according to the following equation:

$$\eta_s = \eta_r \left(\frac{A_r}{A_s}\right)\left(\frac{I_s}{I_r}\right)\left(\frac{n_s^2}{n_r^2}\right)$$

where ($\eta_r$) and ($\eta_s$) are the fluorescence quantum yields of standards and the samples, respectively. $A_r$ and $A_s$ are the absorbance of the standards and the measured samples at the excitation wavelength, respectively. $I_r$ and $I_s$ are the integrated emission intensities of standards and the samples, respectively. $n_r$ and $n_s$ are the refractive indices of the corresponding solvents present in the solutions, respectively. The experimental error was approximately 10%.

To determine sensor responses, 50 μL of 2(a) (Example 10) was dissolved in DMSO resulting in a concentration of 200 μM which was then added into 2 mL of HEPES (10 mM, pH 7.2) buffer. This resulted in a final 2(a) concentration of 5 μM in the buffer. Different metal ion concentrations were added into the solution for studying 2(a)'s responses. Although the reaction of the compound and the metal ion was rapid (usually within seconds), the spectra was measured after 2 minutes to ensure stability. 2(a)/metal ion complexes were excited at 561 nm and emissions were collected from 600 to 750 nm.

Figure 8:
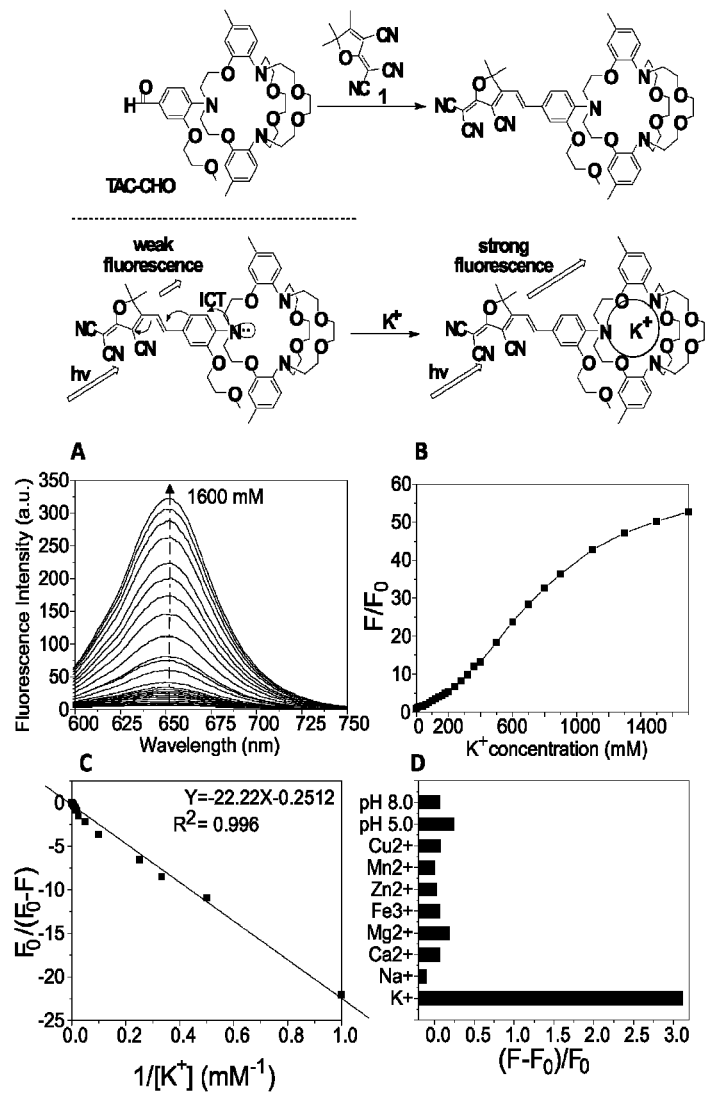
FIG. 8A shows the fluorescence change of 2(a) in HEPES buffer (pH 7.2) containing different KCl concentrations, excited at 561 nm. 8B illustrates the changes of fluorescence intensities at 650 nm at different $K^+$ concentrations. F is the fluorescence intensity at various conditions. $F_0$ is the emission intensity before the titration (with 0 mM $K^+$). 8C is a Benesi-Hildebrand plot of 2(a). 8D shows the fluorescence intensity change of 2(a) in the presence of various biological cations at their physiological concentrations [$K^+$ (150 mM), $Na^+$ (15 mM), $Ca^{2+}$ (2.0 mM), $Mg^{2+}$ (2.0 mM), $Zn^{2+}$ (2.0 mM), $Fe^{3+}$ (50 μM), $Mn^{2+}$ (50 μM), and $Cu^{2+}$ (50 μM)] and different pH values [pH (5.0) and pH (8.0)].

Data for 2(a) is shown in FIG. 8. Because of the strong delocalization of electrons in the push-pull fluorophore in 2(a), the complex ability of the nitrogen atom of the aniline group, a component of the ligand for the potassium ion, decreased significantly. Such a decrease may result in a blunted binding ability of the whole ligand in the compound and decreased sensitivity of the intramolecular charge transfer (ICT) to the complexation with $K^+$ to achieve a $K_d$ of around one-tenth mole level.

2(a) is constructed using strong electron-donating (aniline) and electron-withdrawing (TCF) groups, yielding an absorption maximum at 560 nm. The extinction coefficient(s) at 560 nm is $3.84 \times 10^4$ $M^{-1}$ $cm^{-1}$. 2(a) displays weak fluorescence in its free form with a quantum yield (η) of 0.11%. Upon addition of $K^+$, the fluorescence intensity of 2(a) increases by ca. 4 and 50 fold at $K^+$ concentrations of 140 mM and 1400 mM (FIGS. 8A and 8B), respectively, resulting in corresponding η of 0.52% and 5.6%. $K_d$ was determined by the Benesi-Hildebrand equation:

$$F_0/(F_0-F) = F_0/(F_0-F_{complex}) + F_0/(F_0-F_{complex}) \times K_d \times 1/[M] \quad (1)$$

where $F_0$ is the integrated fluorescence intensity of a free sensor, F is the observed integrated fluorescence intensity, $F_{complex}$ is the emission of the ligand-metal ion complex, and [M] is the metal ion concentration. When $F_0/(F_0-F)$ is plotted against 1/[M], the binding constant is given by the ratio intercept/slope. Curve fitting of 2(a) fluorescence intensity against the reciprocal of the $K^+$ concentration (1/[$K^+$]), this Benesi-Hildebrand plot yields a linear fit (FIG. 8C), where the $K_d$ was estimated to be 88 mM. The linear fit evidences a 1:1 complexation behavior.

Figure 9:
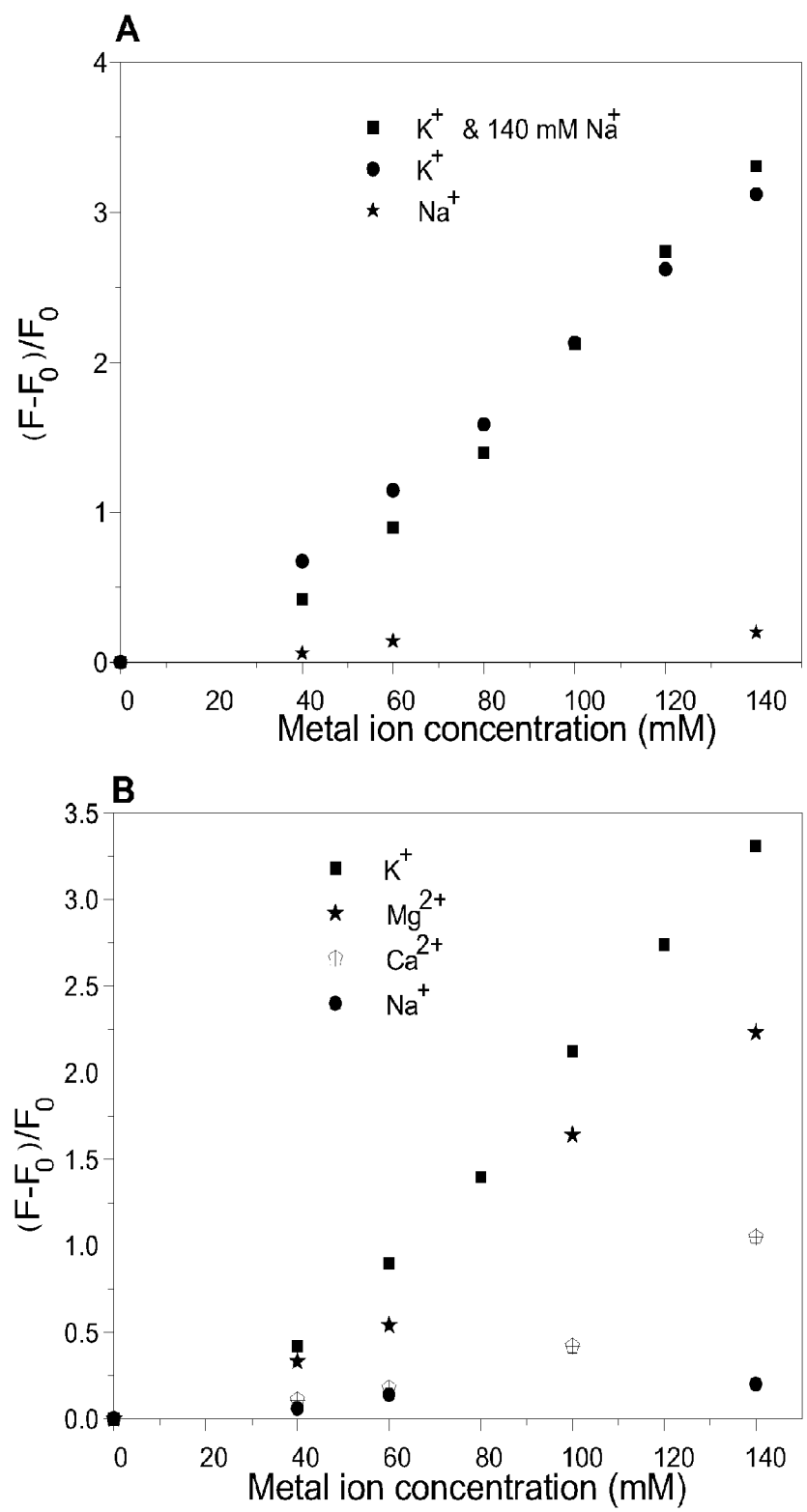
FIG. 9A illustrates the responses of 2(a) to sodium ion, potassium ion, and potassium ion at 140 mM sodium ion condition. 9B shows 2(a)'s responses to sodium ion, calcium ion, magnesium ion, and potassium ion.

2(a) was also tested against physiological concentration levels of the following metal ions: $K^+$, $Na^+$, $Ca^{2+}$, $Mg^{2+}$, $Fe^{3+}$, $Zn^{2+}$, $Mn^{2+}$, and $Cu^{2+}$. The results revealed that the potassium ion had the greatest influence on the sensor's emissions (FIG. 8D). Furthermore, this trend was also present when the concentrations of $Na^+$, $Ca^{2+}$, and $Mg^{2+}$ were increased to 140 mM (FIG. 9). These results showed the high selectivity of 2(a) to $K^+$. 2(a) was not sensitive to pH in the range of 5 to 8. The high selectivity to $K^+$ with a large $K_d$ suggested that 2(a) is useful for intracellular $K^+$ sensing in a wide range of biological condition.

Example 12

Cell Culture for Imaging and Subcellular Distribution of the Sensor

U87MG cells (American Type Culture Collection, ATCC, Manassas, Va.) were cultured in Eagle's minimum essential medium (EMEM) supplemented with 10% fetal bovine serum, 100 μl mL penicillin, 2 mM L-glutamine (Sigma-Aldrich), and incubated at 37° C. in 5% $CO_2$ atmosphere. Cells were then seeded onto 96 well plates at 10,000 cells per well, and incubated for 1 day at 37° C. CP-A cells (kindly provided by Dr. Brian J. Reid at Fred Hutchison Cancer Research Center, Seattle, Wash.) were cultured in Keratinocyte-serum free medium (Invitrogen, Carlsbad, Calif.) supplemented with Bovine Pituitary Extract (BPE) and human recombinant Epidermal Growth Factor (rEGF, Invitrogen) at 37° C. in a 5% $CO_2$ atmosphere. Cells were seeded onto 96 well plates at 10,000 cells per well, and incubated for 1 day. Sensors dissolved in DMSO were added to the medium to make the sensor concentrations in a range of 0.5-5 μM. 10 min of internalization was found to be sufficient for achieving satisfactory images. To achieve images with satisfactory signal-to-noise ratio, a sensor concentration of 4 μM was usually used for intracellular study.

A study was conducted to test whether or not the sensor had specific subcellular distributions in cells: cells were co-stained using the sensor in combination with Hoechst 33342, Lysosensor SM3, and MitoTracker® Green FM, respectively. To co-stain the nuclei, Hoechst 33342 was used. Cells were first internalized with 2(a) (4 μM in cell culture medium) for 10 minutes. After removing medium and washing the cells with fresh medium, Hoechst 33342 dissolved in the fresh medium and was then added into the wells to stain cell nuclei for 30 min at 37° C. In order to co-stain the cell's mitochondria, MitoTracker® Green FM was used. The cells were treated in the same manner as the Hoechst staining method, but with a MitoTracker® Green FM in DMSO solution. To co-stain the lysosomes, Lysosensor SM3 was used. Again the cells were treated using the previously stated protocol while using a SM3 in DMSO solution. The resulting concentrations of Hoechst 33342, MitoTracker® Green FM, and Lysosensor SM3 in the cell medium were 10 μM, 50 nM, and 2 μM respectively.

Under a Nikon Eclipse TE2000E confocal fluorescence microscope (Melville, N.Y.), Hoechst 33342 was excited at 405 nm and its blue emission was collected using a 450/35 nm filter set. Sensor (1(a)) was excited at 440 nm and the green emission was collected using a 515/30 nm filter set. Sensor (2(a)) was excited at 561 nm and its red emission was collected using a 605/75 nm filter set. Lysosensor SM3 was excited at 405 nm and its green emission was collected using a 515/30 nm filter set. And MitoTracker® Green FM was excited at 488 nm and its green emission was collected using a 515/30 nm filter set.

There are some co-localizations of 2(a) with mitochondria and lysosome, since the mitochondria and lysosome also contain potassium ions. These results indicated the non-specific cellular distribution of the potassium ion sensor, 2(a). The non-specific distribution of 2(a) indicated that it can be used to monitor potassium ions in the cytoplasm and in any of these compartments.

Example 13

Cytotoxicity

Cytotoxicity of 2(a) to human glioblastoma U87MG cells was studied using Trypan blue staining. To cell culture medium (100 µL) with eukaryotic cells in a 96 well microplate with 10,000 cells/well that had internalized 2(a) for 2 hours, 10 mL of 0.4% Trypan Blue stain was added and mixed thoroughly with the medium. After standing for 5 min at room temperature (23° C.), the cells were imaged using an optical microscope in bright field mode. Dead cells appeared blue from the Trypan Blue stain, whereas healthy cells appeared transparent as a result of the cell's resistance to stain. The cells were then counted and the ratio of dead cells to live cells was calculated. Each experiment was repeated three times.

Figure 10:
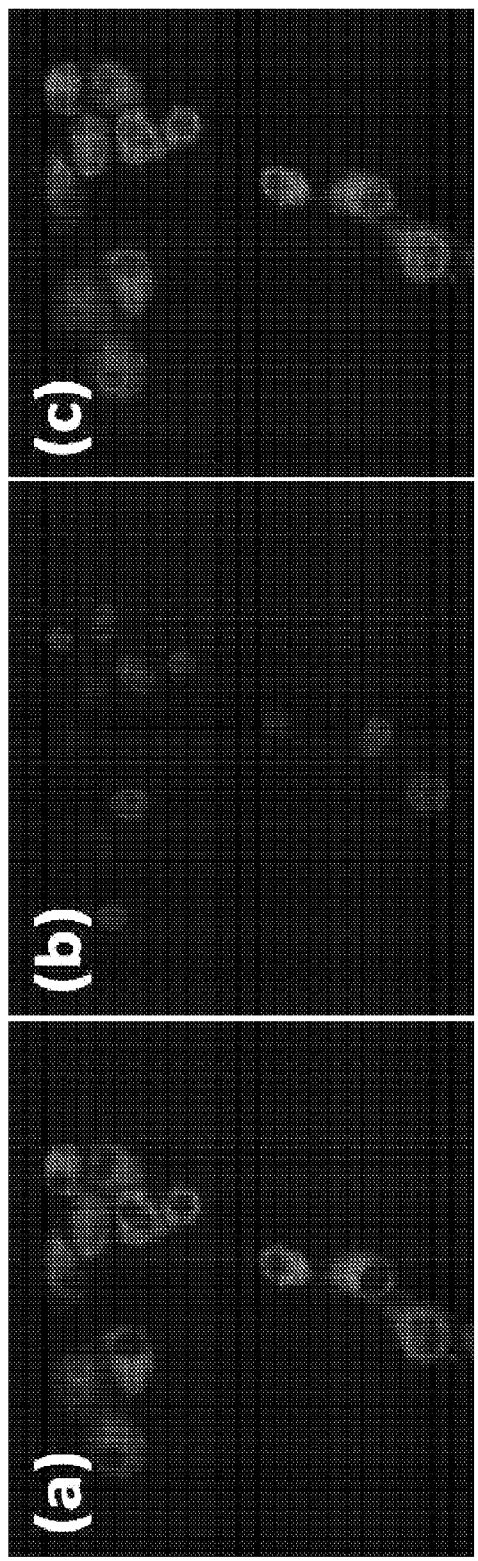
FIG. 10 displays confocal fluorescence images of 2(a) (4 μM) in U87MG cells co-stained with Hoechst 33342 (10 μM). 10(a) is a red emission from 2(a) excited at 561 nm; 10(b) is a blue emission from Hoechst 33342 excited at 405 nm; 10(c) shows an overlay of (a) and (b).
Figure 11:
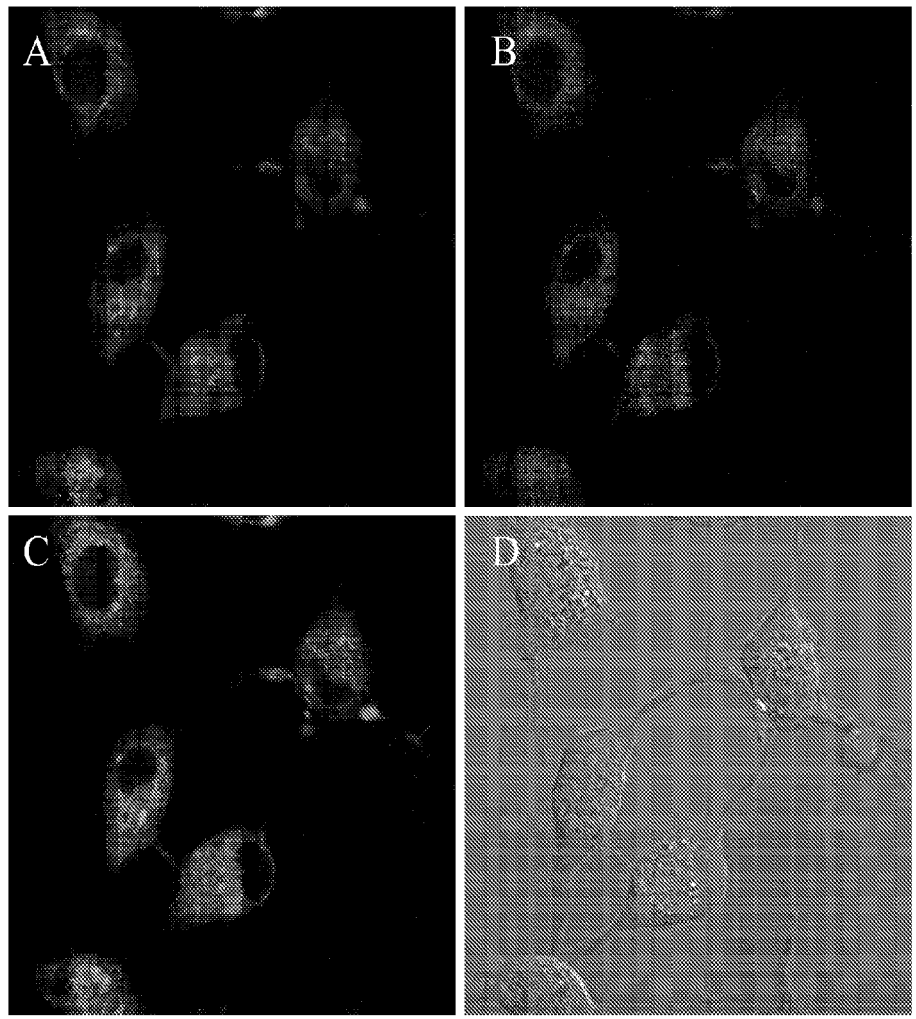
FIG. 11 shows confocal fluorescence images of U87MG cells. 11A depicts the green fluorescence image of cells stained with MitoTracker® Green. 11B depicts the red fluorescence image of cells stained by 2(a). 11C is the overlay of 11A and 11B. 11D is the bright field image of cells.
Figure 12:
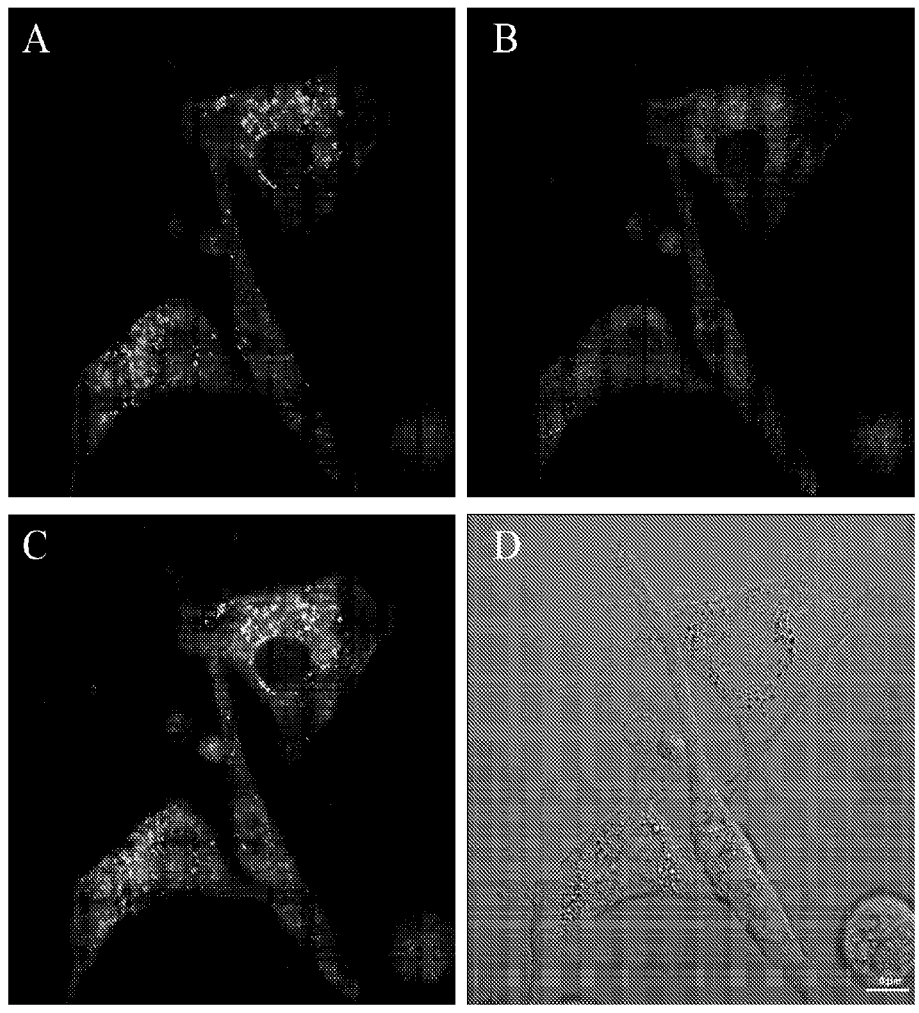
FIG. 12 shows confocal fluorescence images of U87MG cells. 12A depicts the green fluorescence image of cells stained by SM3. 12B depicts the red fluorescence image of cells stained by 2(a). 12C is the overlay of 12A and 12B. 12D is the bright field image of cells. 12E is the chemical structure of SM3.
Figure 12:
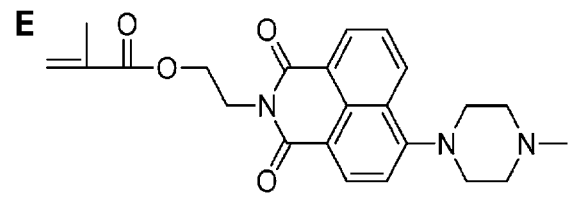

After internalizing the sensor with cells for 2 hours, more than 97% of the cells were viable, showing the non-cytotoxicity of 2(a) to U87MG cell line under our experimental conditions. Confocal images of U87MG cells internalized with 2(a) showed that 2(a) could be taken up by cells within 10 minutes. Red fluorescence was observed in the cytoplasm area, which was further confirmed by a minimum colocalization with blue emission from the nucleic staining probe (Hoechst 33342) (FIG. 10). Furthermore, the sensor did not have a specific colocalization in mitochondria or lysosomes, showing that 2(a) has a non-specific distribution and will therefore monitor potassium ions in the cytoplasm and in any of these compartments (FIGS. 11 and 12).

Example 14

Monitoring the Intracellular $K^+$ Efflux Using 2(a)

To monitor the stimuli-response of the intracellular $K^+$ level, cells internalized with 4 µM of 2(a) for 10 minutes were treated with a mixture of nigericin, bumetanide, and ouabain (FIG. 13) at 37° C. Specifically, U87MG cells were seeded onto 96 well plates at 10,000 cells per well in 100 µL medium overnight at 37° C. On the following day, the cells were internalized with 2(a) (4 µM) for 10 min at 37° C. A mixture of nigericin, bumetanide, and ouabain was then added. Final concentrations of nigericin, bumetanide, and ouabain in the cell culture medium were 5 µM, 10 µM, and 10 µM, respectively. Fluorescence in cells was visualized by Nikon Eclipse TE2000E confocal fluorescence microscope (Melville, N.Y.) at 37° C.

Figure 13:
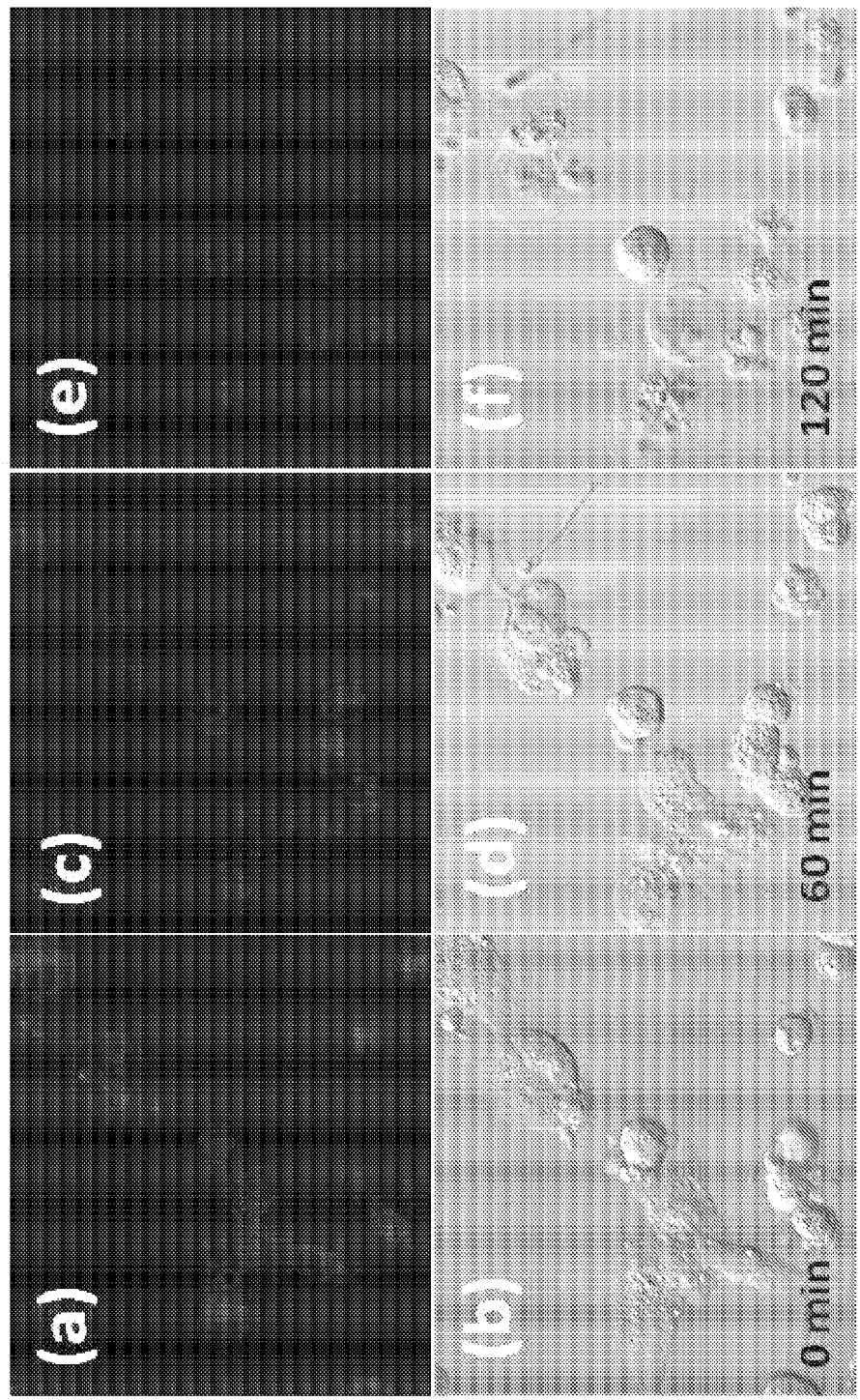
FIG. 13 illustrates the time-dependent intracellular $K^+$ in U87MG cells after treatment with a mixture of nigericin, bumetanide, and ouabain for 0 min (13a and 13b), 60 minutes (13c and 13d), and 120 minutes (13e and 13f). Top: fluorescence images; Bottom: bright field images. Concentrations of 2(a), nigericin, bumethanide, and ouabain for this study were 4 µM, 5 µM, 10 µM, and 10 µM, respectively.

The decrease of the fluorescence intensities indicated the efflux of the intracellular $K^+$ from cells (FIGS. 13a, 13c, and 13e). The combination of the ionophore nigericin with influx inhibitors of bumetanide (inhibitor of $Na^+$, $K^+$, $2Cl^-$-cotransport) and ouabain (inhibitor of $Na^+$, $K^+$, ATPase pump) is an effective $K^+$-efflux stimulator. This mixture effectively induced $K^+$ efflux as shown in fluorescence images (FIG. 13). Meanwhile, cell shrinkage with a preservation of an intact plasma membrane was observed after 60 mins of stimulation. It has been known that depletion of intracellular $K^+$ will result in cell shrinkage, activated caspases, and DNA fragmentation, all of which are features of apoptosis. Therefore, the phenomenon observed in FIG. 13 indicated that U87MG cells underwent the apoptotic change through the $K^+$ efflux induced by nigericin, ouabain, and bumetanide. A control experiment without the drug stimulation did not show obvious fluorescence intensity changes or morphological shrinkages.

Example 15

Monitoring the Intracellular $K^+$ Influx Using 2(a)

2(a) can also be used to monitor $K^+$ influx through stimuli. U87MG cells were seeded onto 96 well plates at 10,000 cells per well in 100 µL medium overnight at 37° C. On the following day, the cells were internalized with 2(a) (4 µM) for 10 min at 37° C. The influx stimulator (isoproterenol in KCl-containing PBS buffer) was added. Final concentrations of the added isoproterenol and KCl in the cell culture medium were 5 µM and 20 mM, respectively. Fluorescence in cells was visualized by Nikon Eclipse TE2000E confocal fluorescence microscope (Melville, N.Y.) at 37° C.

Figure 14:
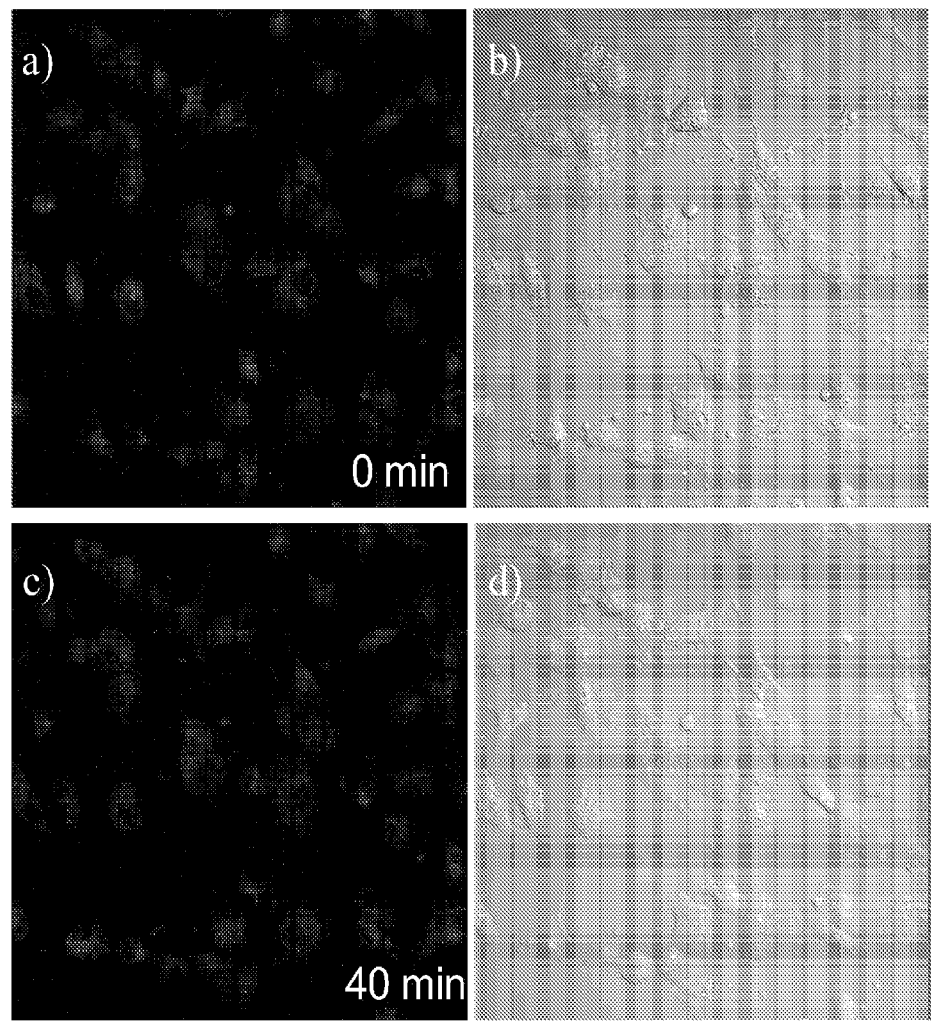
FIG. 14 provides fluorescence images of 2(a) at high concentrated KCl (20 mM) and isoproterenol (5 µM)-containing medium. 14a and 14c are fluorescence images. 14b and 14d are the fluorescence images superimposed with bright field images. 14a and 14b are for time of 0. 14c and 14d are for time of 40 minutes. Average fluorescence intensity increased 33% by the isoproterenol stimulation analyzed using ImageJ.

Internalization with 2(a) only induced a slight fluorescence intensity increase, while obvious fluorescence increase was observed after cells were treated with 5 µM isoproterenol and the 20 mM KCl in medium for 40 minutes at 37° C. (FIG. 14). Isoproterenol was reported to be a potassium ion influx stimulator by stimulating cyclic adenosine monophosphate (cAMP) generation, which associates with physiology change in $K^+$ transport. The average fluorescence intensity of cells after the treatment was 33% greater than that before the treatment; which was quantified using ImageJ software—a public domain developed at the National Institute of Health.

Example 16

Dynamic Potassium Ion Influx and Efflux

Figure 15:
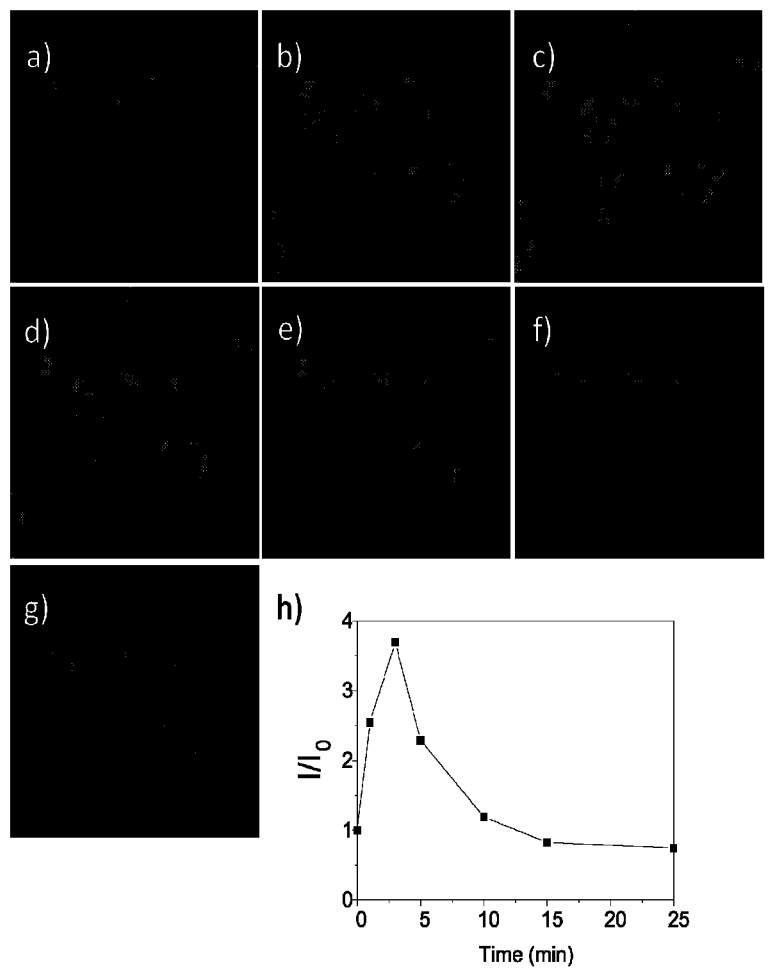
FIG. 15 shows the time-dependent fluorescence of U87MG cells stimulated by nigericin observed under confocal fluorescence microscope. 15a is time of 0 before the addition of nigericin; 15b, 15c, 15d, 15e, 15f, and 15g are time of 1, 3, 5, 10, 15 and 25 minutes, respectively, after the addition of nigericin (20 µM, final concentration) into the 20 mM KCl-containing medium; 15h gives the average fluorescence intensity ratios measured by ImageJ. I0 is the average fluorescence intensity from FIG. 15a; I is the average fluorescence intensity at different times.

2(a) was further tested for in-situ observation of dynamic potassium ion influx and then efflux through the changes of fluorescence (FIG. 15) stimulated by an ionophore nigericin. Cells internalized with 4 µM of 2(a) at 37° C. for 10 minutes were washed with 20 mM KCl-containing fresh medium. Nigericin (20 µM at its final concentration) was added in 20 mM KCl-containing medium to help $K^+$ to across cell membrane. Enhanced fluorescence was immediately observed after the addition of nigericin, indicating potassium ion influx occurred. The potassium influx peaked after 3 minutes with an average of fluorescence increase of 370%. After 3 minutes, potassium efflux was observed by the decrease of the fluorescence. The efflux stabilized after 15 minutes, and the fluorescence intensity after the stabilization was about 25% below that of before the stimulation by nigericin. The ionophore nigericin was used to stimulate $K^+$ influx for yeast *Saccharomyces cerevisiae*. It was also reported to be a $K^+$ efflux stimulator for human colorectal adenocarcinoma HT-29 cells. The observation of the $K^+$ influx and then efflux of U87MG cells using 2(a), demonstrating its further utility in measuring the kinetic of $K^+$ transport.

Example 17

Interference of Benzofuran Isophthalate (PBFI) on 2(a) Uptake

For this comparison, two independent experiments were carried out. In the first experiment, cells were internalized with 2(a) for 10 minutes at a concentration of 2 µM at 37° C. for 10 minutes. Then the medium containing the sensor was removed, and new medium was added for imaging at 37° C. While in the second experiment, the cells were first internalized with PBFI at a concentration of 10 µM in cell culture medium for 30 minutes at 37° C. Then 2(a) (at a concentration of 2 µM) was added to the cell medium. Cells were further incubated at 37° C. for 10 minutes. After which the sensor and medium were removed, and new medium was added for imaging at 37° C. The excitation wavelength was 561 nm and the emissions were collected using a 605/75 nm filter set. Both of the experiments were carried out using the same optical procedure.

Example 18

Synthesis of a Compound of Formula (1): 1(a)

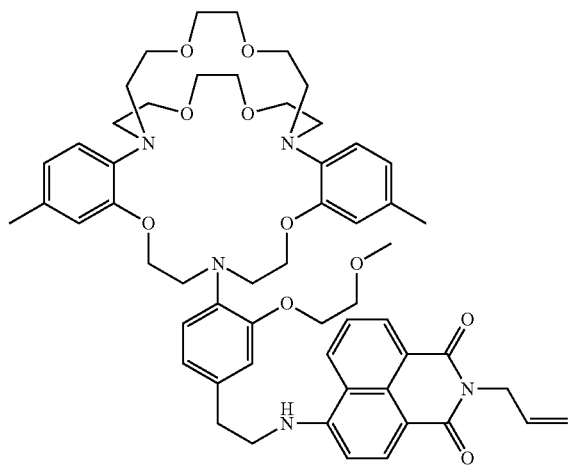 [SMILES: C=CCN1C(=O)c2cccc3c(NCCc4ccc(N5CCOc6cc(C)ccc6N6CCOCCOCCN(CCOCCOCC6)c6ccc(C)cc6OCC5)c(OCCOC)c4)ccc(c23)C1=O]

100 mg (135.7 μmol) of TAC-NH$_2$, 51.5 mg (149.27 μmol) of compound 1, and 21.1 mg of DIPEA were suspended in 1 mL NMP and microwaved to 150° C. for 4 h. The mixture was poured into 10 mL water. The resulting precipitate was filtered off, and then washed with 10 mL water. The crude product was purified using a silica gel column to yield 36 mg yellow gum. Yield: 27.3%.

Example 19

Typical Procedure for Extracellular Sensing Film Preparation

Thin films were prepared according to our published protocols (Tian Y. et al., *Biomaterials* 2010; 31:7411-7422; and Tian Y. et al., *Chem Mater* 2010; 22:2069-2078). A schematic drawing of the film preparation is given in FIG. 16. F4 film is described as a typical example. The components of other films are given in Table 1.

TABLE 1

Compositions of the films F1 to F8, their sensitivity, and K$_d$ values.

| Films | Polymer compositions and their weight ratios[a] | Sensitivity (F/F$_0$)[b] | K$_d$ (mM) |
|---|---|---|---|
| F1 | PAM | 1.02 (±0.01) | N/A |
| F2 | PHEMA | 1.77 (±0.03) | 18.5 |
| F3 | PHEMA:PAM (50:40) | 2.03 (±0.03) | 14.9 |
| F4 | PHEMA:PAM (80:15) | 2.34 (±0.02) | 7.25 |
| F5 | PHEMA:PAM:PMETAC (80:15:20) | 1.59 (±0.02) | 26.3 |
| F6 | PHEMA:PAM:PMETAC (80:15:5) | 1.90 (±0.02) | 15.8 |
| F7 | PHEMA:PAM:PMESA (80:15:5) | 2.69 (±0.03) | 6.04 |
| F8 | PHEMA:PAM:PMESA (80:15:20) | 3.03 (±0.03) | 4.96 |

[a] Each film contains a 5%-weight percent SR454 crosslinker.
[b] The sensitivity of the sensing films to K$^+$ was at the 0 and 10 mM KCl conditions for comparison because this range is usually enough for extracellular K$^+$ sensing. F$_0$ is the fluorescence intensity before the titration using KCl. F is the fluorescence intensity at 10 mM KCl.

1 mg of the monomeric 1(a), 800 mg of HEMA, 150 mg of AM, 50 mg of SR454, and 10 mg of AIBN were dissolved in 1 mL DMF as a stock solution. 15 μL of the stock solution was added onto the surface of the TMSPA-modified quartz glass and covered with a clean but untreated cover slip to make a sandwich structure. Using TMSPA to modify the quartz glass was to enable the sensors and matrices to be chemically grafted onto a quartz substrate (Tian Y, et al., *Chem Mater* 2010; 22:2069-2078). The thickness was controlled using 25 μm Kapton tape (DuPont, Wilmington, Del.). The sandwich set-up was placed into a vacuum oven, which was then evacuated and refilled with nitrogen three times. Polymerization was carried out under nitrogen at 80° C. for 1.5 h in the oven. The quartz glasses with polymer membranes were removed from the oven, then the Kapton tape and non-surface modified glass was removed from the polymerized membrane surface. The polymerized membranes on the quartz glasses were washed three times with methanol to remove any remaining non-polymerized monomers and residual DMF. The films were dried and stored away from light at room temperature. The sensing films were stable in water for at least 3 months without any leaching of the sensing moieties or change in sensing performance.

Example 17

Culture of *E. Coli* and *B. Subtilis* for Potassium Release Study

*E. coli* JM 109 and *B. subtilis* 168 were cultured overnight in LB medium (Difco®, Becton, Dickinson and Company, Sparks, Md.) by shaking at 180 rpm at 37° C. The concentration of *E. coli* and *B. subtilis* in culture was estimated by measuring the optical density at 600 nm (OD$_{600}$). OD$_{600}$ value of 1 indicated a concentration of 5.0×10$^8$ cfu/mL. After the microorganism density was determined, bacterial cells were collected by centrifuge at 2000×g for 20 minutes at room temperature. Then appropriate densities of bacteria were made using fresh buffer (150 mM NaCl, pH 7.4) to achieve the desired initial concentrations for experiments.

The F4 film (Example 16) was placed diagonally into quartz cuvettes with 2 mL of bacteria suspension at different densities. Potassium release from the bacteria was stimulated by adding 100 μL of 20 mg/mL lysozyme. Emission measurements were taken every 5 min at the sensor's peak emission (525 nm) using an excitation wavelength of 450 nm. The potassium ion concentration was calculated from the measured fluorescence ratio (F/F$_0$).

Example 18

Sensing Performance of 1(a) in Buffer

Figure 17:
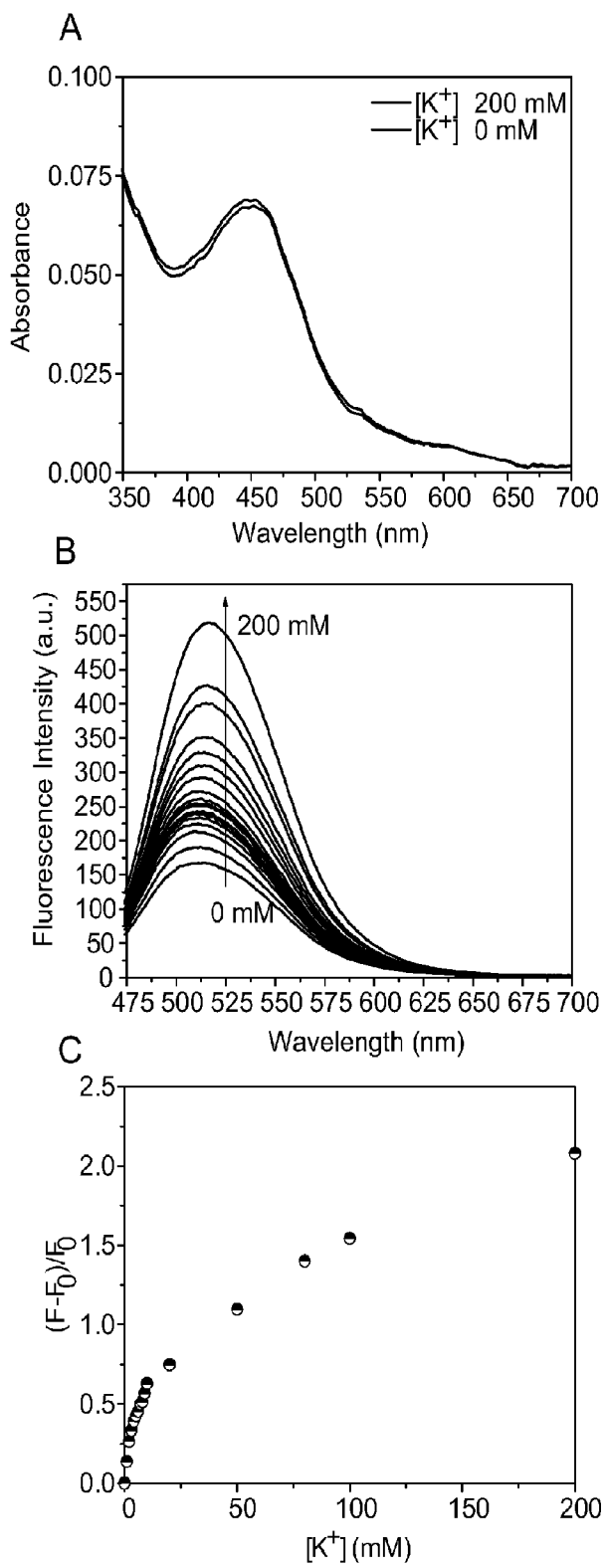
FIG. 17A is a UV-Vis spectra of 1(a) at 0 mM and 200 mM potassium chloride (KCl) conditions. 17B shows the fluorescence spectral change of 1(a) in 10 mM HEPES buffer containing different KCl concentrations using an excitation wavelength at 450 nm. 17C provides the change of fluorescence intensity at 525 nm at different potassium ion concentrations. F is the fluorescence intensity at various conditions. F0 is the emission intensity before the titration (with 0 mM $K^+$). 17D is the Benesi-Hildebrand plot of 1(a). 17E shows the fluorescence intensity change of 1(a) in the presence of various biological cations at their physiological concentrations: $Na^+$ (15 mM), $Ca^{2+}$ (0.5 mM), $Mg^{2+}$ (2.5 mM), $Fe^{3+}$ (18 mM), $Zn^{2+}$ (45 mM), $Mn^{2+}$ (0.9 mM), and $Cu^{2+}$ (16 mM).
Figure 17:
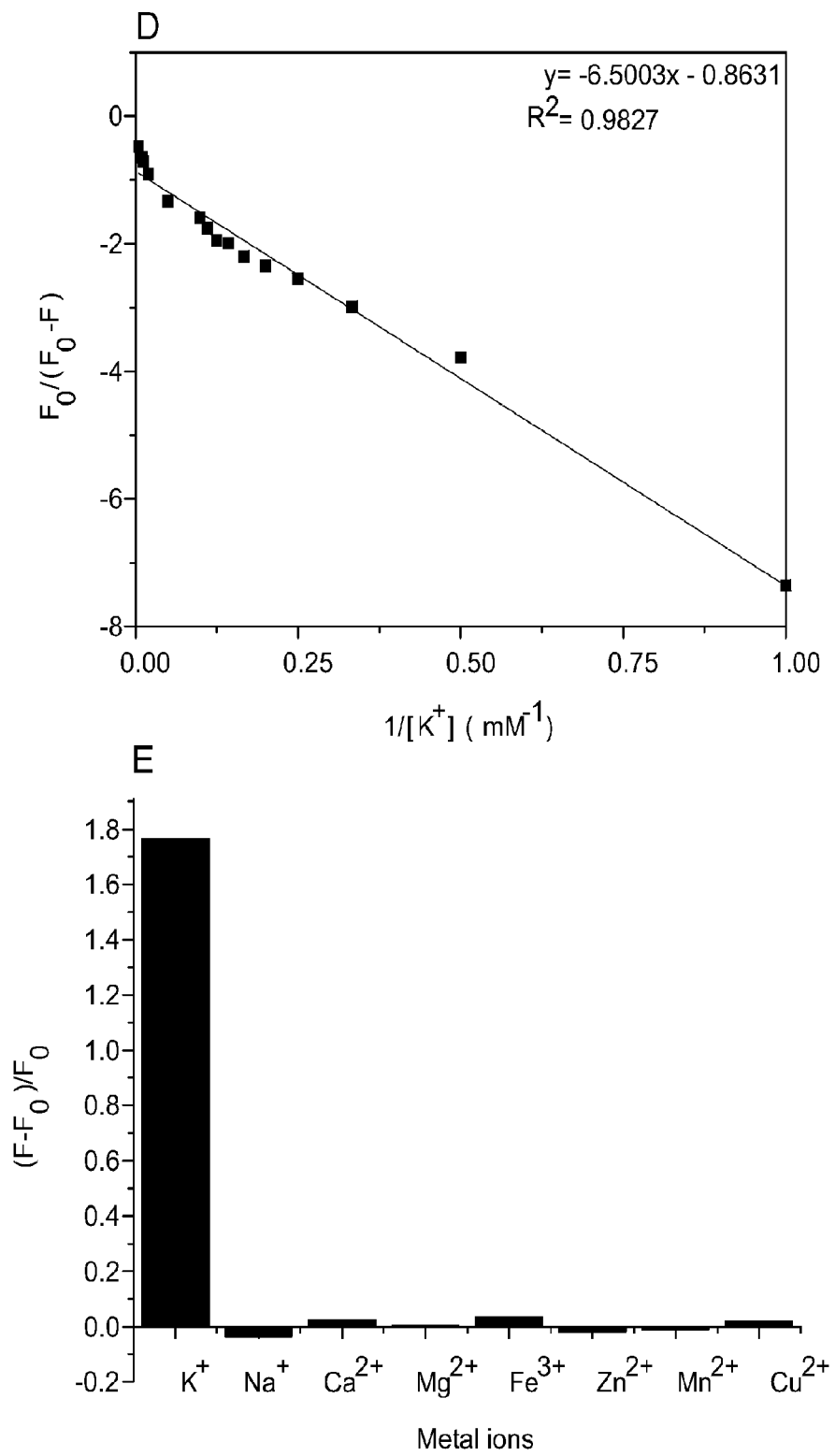

FIGS. 17A and 17B show the UV-Vis and emission spectral changes upon the interaction of 1(a) with potassium chloride (KCl) in 10 mM HEPES buffer (pH 7.4). The absorption spectra before and after interaction with K$^+$ did not change, while emission intensities increased with increasing K$^+$ concentrations. This fluorescence change was attributed to photo-induced electron transfer. The lone electron pairs of the amino groups in the triazacryptand ligand quench the emission of the fluorophore of the amino-naphthalimide through PET. After interaction with K$^+$, the lone electron pairs of the ligand were occupied due to the formation of the ligand-K$^+$ complex. This change restores the emission of the amino-naphthalimide fluorophore. Fluorescence intensity change at 525 nm was plotted again K$^+$ concentration, which is illustrated in FIG. 17C. Binding constant K could be determined by the fluorescence spectral change using the Benesi-Hildebrand equation as described above.

Curve fitting of the fluorescence intensity of 1(a) against the reciprocal of the K$^+$ concentration (1/[K$^+$]), the Benesi- Hildebrand plot, gives a linear fit (FIG. 17D). This is a characteristic of a 1:1 complexation behavior from which the binding constant (K) is estimated to be 0.133 mM$^{-1}$, corresponding to the disassociation constant ($K_d$) of 7.53 mM.

1(a) shows a high selectivity against a few biologically relevant metal ions (FIG. 17E) including Na$^+$. Na$^+$ is usually an interference ion to K$^+$ for the typical K$^+$ probes including PBFI, CD18, C18, and MCC.

Example 19

Monitoring the Intracellular K$^+$ Efflux Using 1(a)

U87MG and CP-A cells were seeded onto 96 well plates at 10,000 cells per well and maintained in 100 μL medium overnight. The following day, the cells were loaded with 1(a) (2 μM) for 20 min, then the excess 1(a) was removed by washing with medium. The test substances were added and the experiment was terminated after 2.5 h by washing the cells with physiological NaCl solution. A microplate reader (Molecular Device, Downingtown, Pa.) was used to read the fluorescence intensities from the intracellular 1(a). 444 nm was used to excite the sensor and the emission was measured at 538 nm. The measured fluorescence intensities were corrected with background fluorescence. Each experiment was repeated in triplicate.

Example 20

Sensing Performances of 1(a) in the Membranes of F1 to F8

Figure 18:
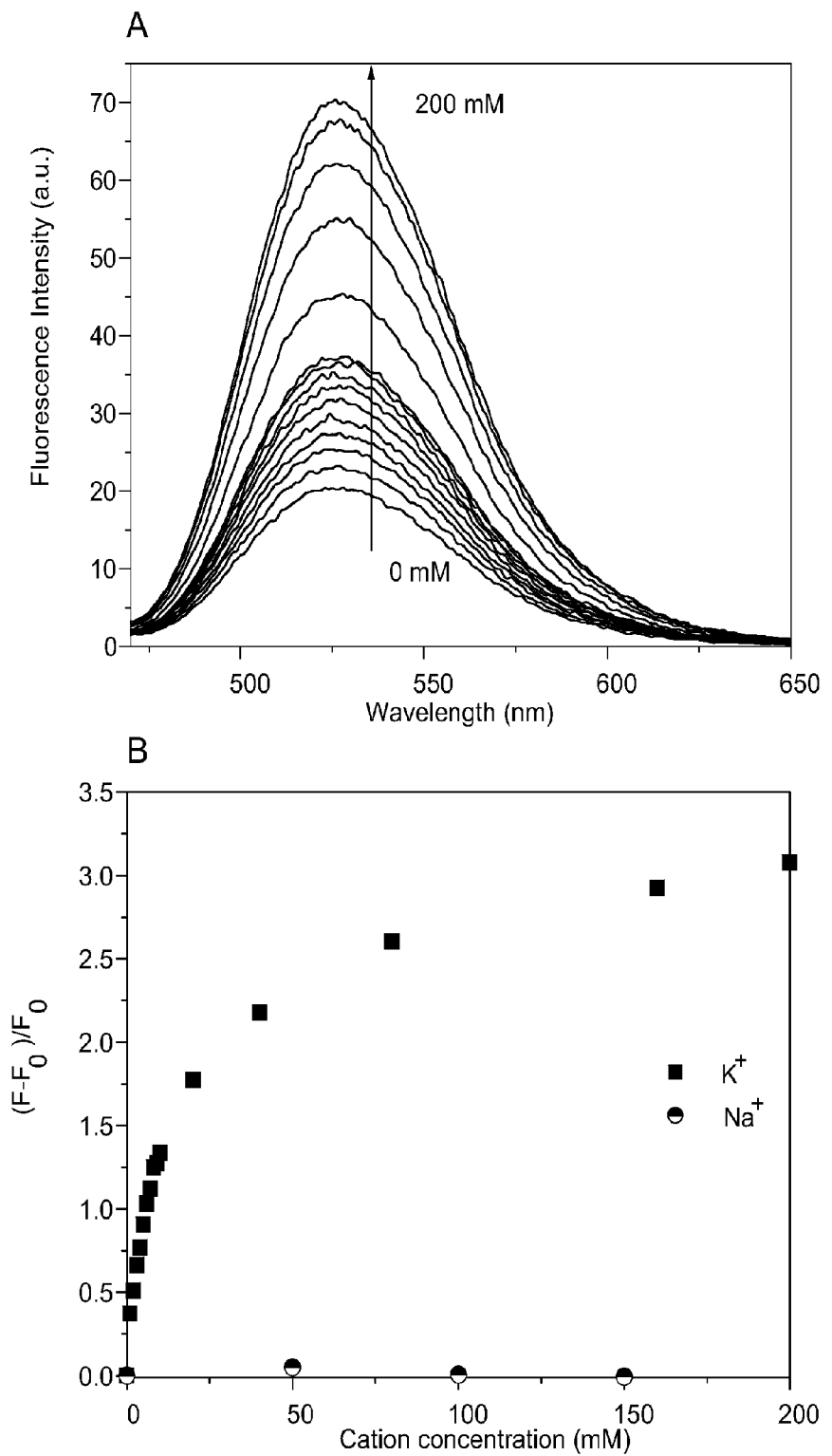
FIG. 18A is an emission intensity change of the 1(a)-conjugated PHEMA-co-PAM (F4) with KCl in buffer. 18B illustrates the change of fluorescence intensity at 525 nm at different KCl and NaCl concentrations. F is the fluorescence intensity at various conditions. F0 is the emission intensity before titration (with 0 mM $K^+$). 18C is a Benesi-Hildebrand plot of F4. 18D shows the influence of pH values on the fluorescence intensities at 525 nm of F4 film before and after the complexation with variable potassium ions.
Figure 18:
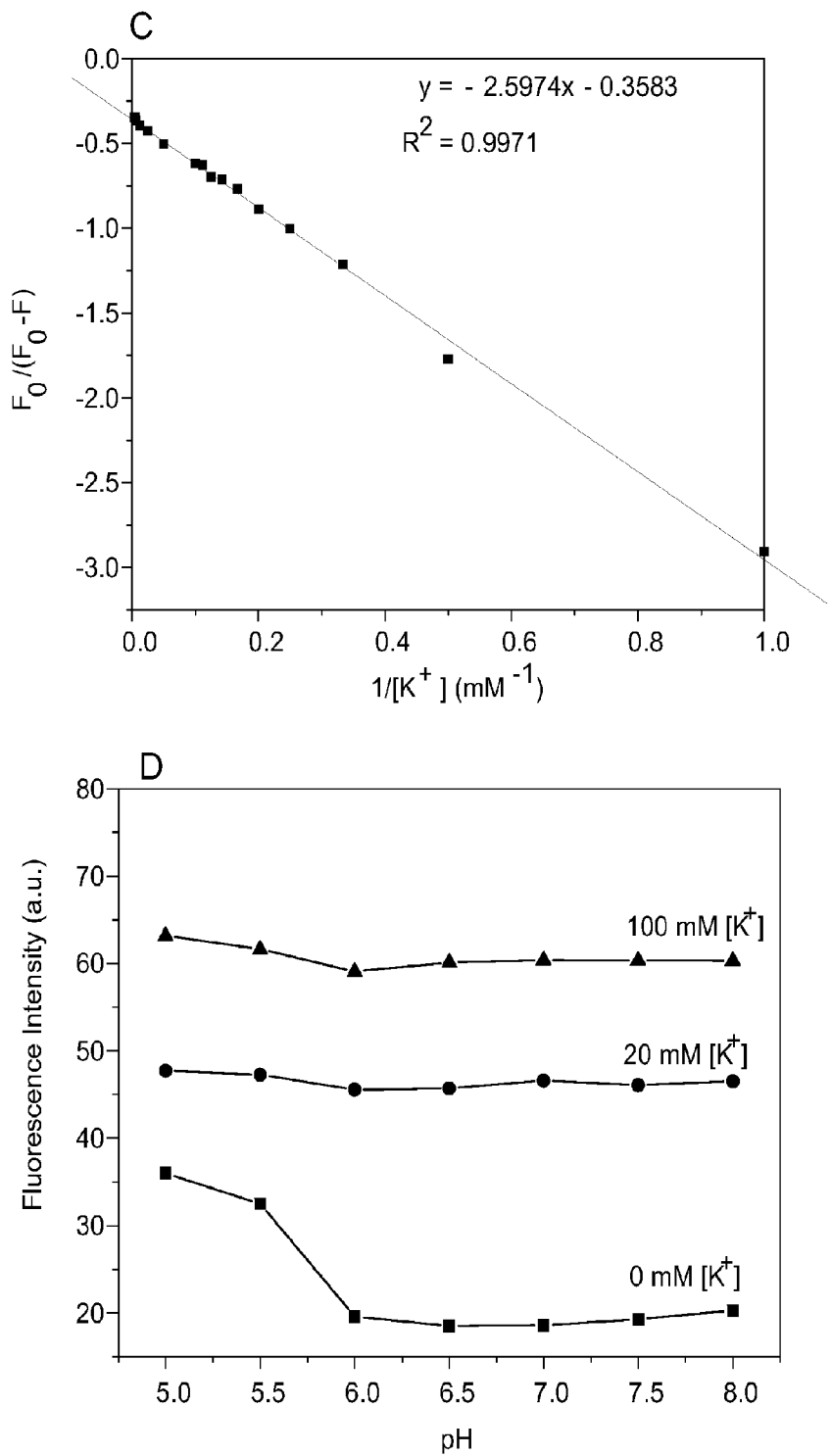

Typical K$^+$ sensing using film F4, made of PHEMA-co-PAM with 80:15 by weight, is shown in FIG. 18. FIG. 18A shows the emission change upon titration with KCl. Its corresponding fluorescence intensities at 525 nm were given in FIG. 18B. The sensing response to Na$^+$ was also given in FIG. 18B, showing the high selectivity of K$^+$ to Na$^+$. This trend is in accordance with that of pure 1(a) in buffer. However, the sensitivity of this sensing film F4 is better than that of pure 1(a), which may possibly be due to the fact that this sensing film can be swollen by water, resulting in a better interaction of the sensing moiety in the PHEMA-co-PAM hydrogel with K$^+$. Curve fitting of the fluorescence intensity of F4 against the reciprocal of K$^+$ concentration (1/[K$^+$]) using the Benesi-Hildebrand equation 1 gives a linear fit (FIG. 18C). This suggests the characteristic of a 1:1 complexation behavior from which the association constant (K) is estimated to be 0.138 mM$^{-1}$, corresponding to the disassociation constant ($K_d$) of 7.25 mM.

For K$^+$ sensors, besides the interference by Na$^+$, pH value is another factor to be concerned. FIG. 18D plots the pH dependent fluorescence changes at different pH values. Results showed that this sensing membrane before the complexation with K$^+$ had no response to pH from 6 to 8. After the complexation with the K$^+$, the sensing membrane did not respond to pH from 5 to 8. These results are in accordance with other K$^+$ sensors derived from the triazacryptand ligand. These results showed our K$^+$ sensors are minimally influenced by biological pH values.

Figure 19:
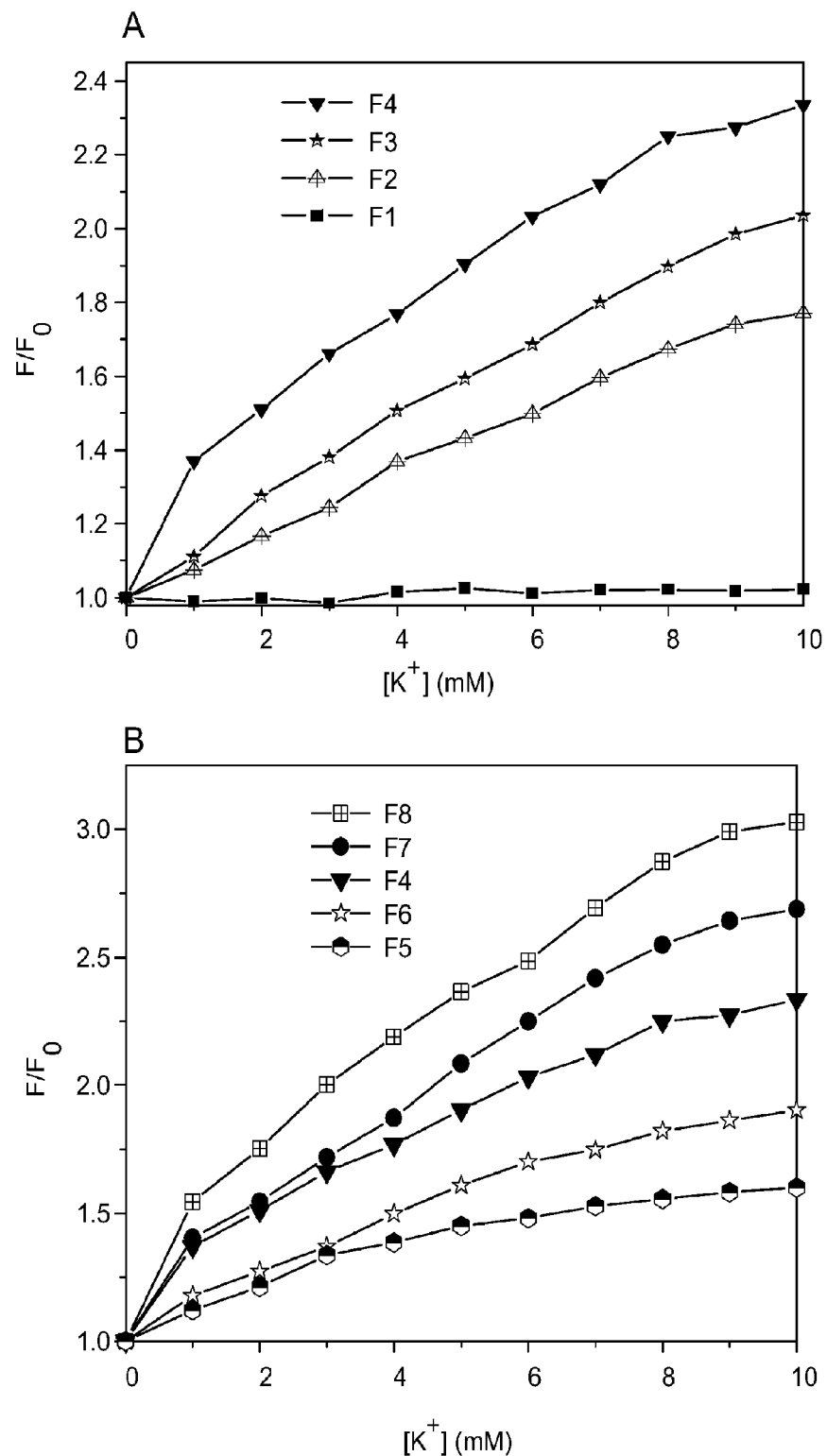
FIG. 19A shows the fluorescence intensity changes of F1, F2, F3, and F4 titrated using KCl in the concentration range of 0 to 10 mM. 19B illustrates the fluorescence intensity changes of F4, F5, F6, F7, and F8 titrated using KCl in the concentration range of 0 to 10 mM.

FIG. 19 gives the comparison of the responses of the eight thin films to K$^+$. The sensing membrane made of PAM matrix (F1) did not response to K$^+$, indicating its poor K$^+$ permeability. Sensing membrane F2 made of PHEMA has better response to K$^+$ than that of F1. Interestingly, the two films of F3 and F4 show much better sensitivity than F2, indicating the chemical composition of the PHEMA-co-PAM improves K$^+$ permeability. It is known that PHEMA can have good swelling properties and ion permeability. However, its swelling and ion permeability could be further improved by the copolymerization with other water soluble polymers, such as PAM. The composite materials can increase the swelling degree ($W_\infty$) and therefore increase the range of pore sizes and size distribution in the hydrogel film. To our knowledge, this is the first study of matrix influence on potassium ion sensitivity of a K$^+$ probe Charges of polymers also affect the sensing activities of sensing films. Increasing the density of negative charge on the film by MESA obviously improved the sensitivity of K$^+$ response. In contrast, increasing the density of positive charge by METAC decreased the response sensitivity to K$^+$. At present the detailed mechanism is not completely understood, but it is believed to be related to the ion permeability of the matrix and the water swelling properties of the various composite materials.

The above studies demonstrate that by taking the advantages of the polymerizable vinyl group, different sensing membranes could be prepared through the tuning of the structures of monomeric precursors for matrices and their composited ratios. Through the tuning of the chemical composites, the sensing performances were also manipulated.

Example 20

Demonstration of the Applicability of 1(a) for Intracellular Sensing

Figure 20:
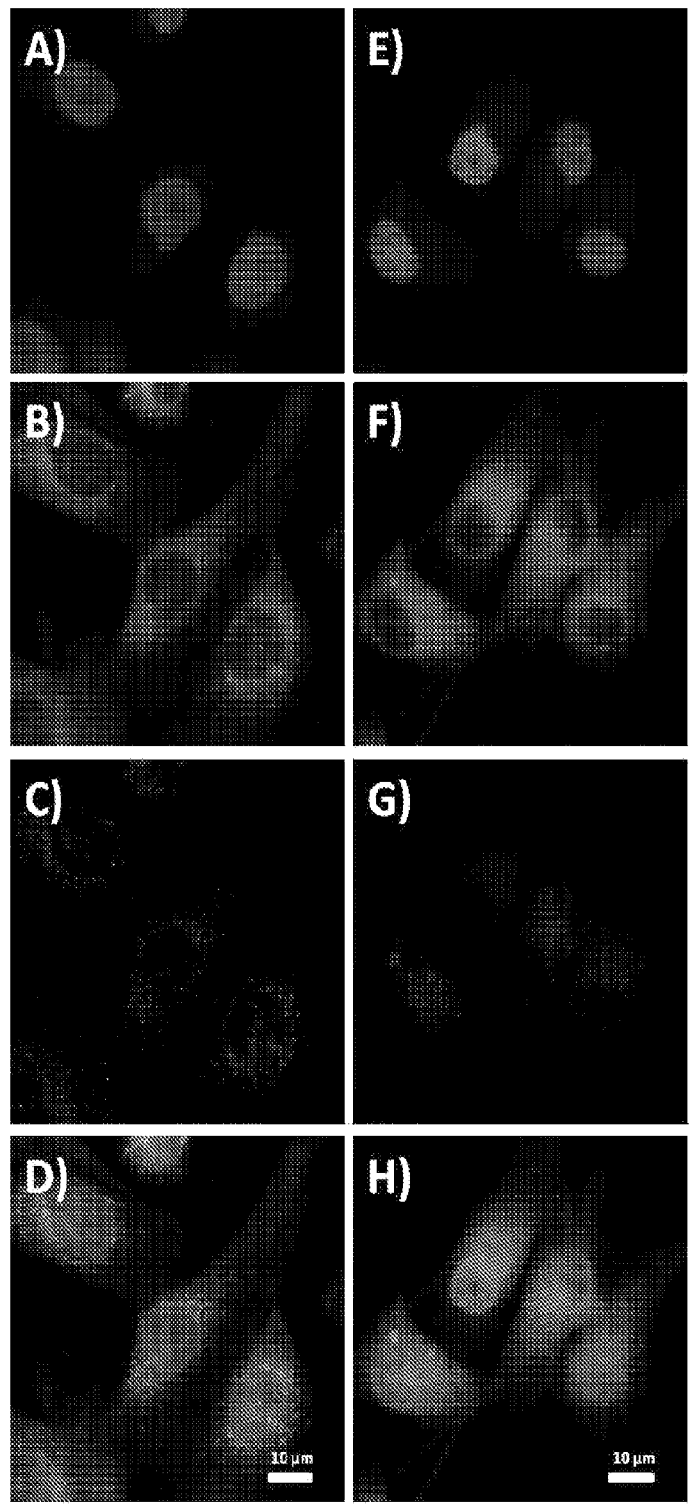
FIG. 20 illustrates the confocal fluorescence images of CP-A (A-D) and U87MG (E-H) cells. 20A and 20E depict the blue channel, showing nuclei stained with Hoechst 33342. 20B and 20F depict the green channel, showing the loading of 1(a) into the cells. 20C and 20G depict the red channel, showing lysosomes loaded with LysoTracker Red®. 20D is the overlay of 20A, 20B and 20C. 20H is the overlay of 20E, 20F and 20G.

Two cell lines (U87MG and CP-A) were used for intracellular sensing. It is well known that cells usually contain about 150 mM of K$^+$, which is within the sensing range of 1(a). FIG. 20 shows the confocal fluorescence images of 1(a). 1(a) can internalize with cells within a short time, as few as 10 minutes. A 1(a) concentration of 0.5 μM in cell culture medium was able to stain cells, but the signal was weak. To achieve images with satisfactory signal-to-noise ratios, a sensor concentration of 2 μM was used for intracellular study. Bright green fluorescence was not uniform throughout the cells, implying the nonuniform K$^+$ distribution of the intracellular K$^+$ in the cytoplasm area. The subcellular distribution of the sensor in the cytoplasm region was further confirmed by a minimum colocalization of the green emission of 1(a) with blue emission from the nuclear staining probe (Hoechst 33342). For intracellular sensing, a significant concern is whether the sensor is affected by the intracellular pH value, especially the low pH value (around 4.5 to 5.5) of the lysosome. To assess this, cells were co-stained with 1(a) and LysoTracker Red®, which is a specific staining reagent for lysosome with red emission. Only minimum overlay of the green emission from 1(a) with red emission from LysoTracker Red® was observed from the yellow color, indicating 1(a) responds to K$^+$, rather than pH. This could be attributed to 1(a) not responding to biologically relevant pH values. Therefore, 1(a) has been demonstrated as a good K$^+$ sensor for intracellular potassium ion imaging.

Example 21

Cytotoxicity

Cytotoxicity of the sensor 1(a) to cells was studied using Trypan blue staining. After 30 minutes internalization of the sensor with cells, more than 97% cells were viable, showing the non-cytotoxicity of 1(a) to the two cell lines under our experimental conditions.

Example 22

Stimuli Responsive Change of the Intracellular K+ Level

Figure 21:
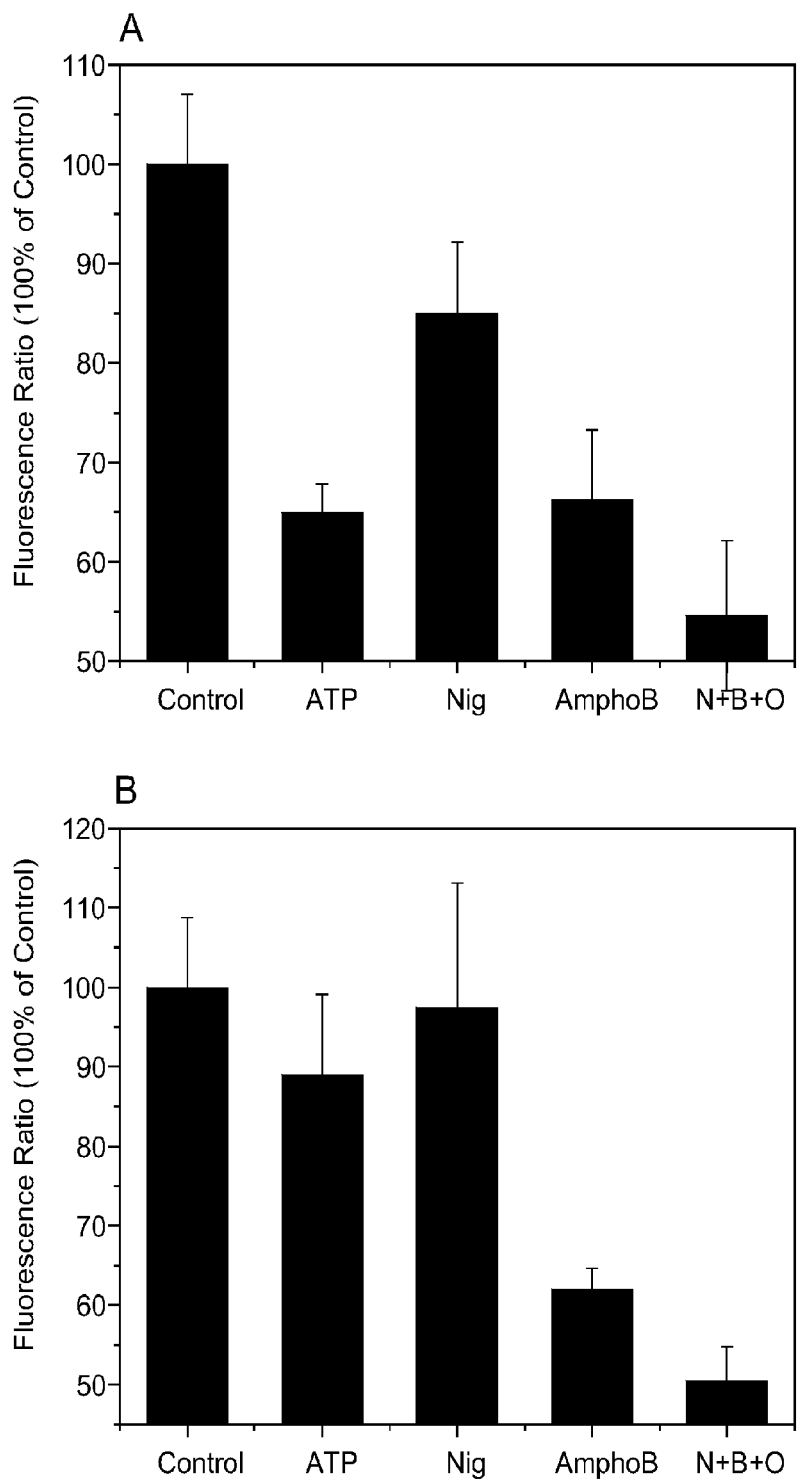
FIG. 21 shows the fluorescence change of cells loaded with 1(a) stimulated with ATP, amphotericin (amphoB), nigericin (Nig), and the mixture of nigericin, bumetanide, and ouabain (N+B+O). 21A represents the U87MG cell line. 21B represents the CP-A cell line. Concentrations of the stimuli materials were: ATP (100 µM), nigericin (5 µM), amphotericin B (3.25 µM), bumetanide (10 µM), and ouabain (10 µM). 444 nm was used as the excitation wavelength and emission was measured at 538 nm using a microplate reader.

To monitor the stimuli-responsive change of the intracellular K+ level, cells internalized with 2 μM 1(a) for 20 minutes were treated with ATP, nigericin (Nig), amphotericin B (Ampho B), and a mixture of nigericin, bumetanide, and ouabain (FIG. 21). The decrease of the fluorescence intensities indicates the efflux of the intracellular potassium ions from the cells. ATP is stimulating molecule of ATP-gated K+ channels. Amphotericin B (AmphoB) is an efflux stimulator. Nigericin is an ionophore. The relative percentages of the fluorescence intensities before and after the addition of the stimuli materials are given in FIG. 21. It was found that nigericin ionophore was not an efficient K+ efflux stimulator. However, the combination of the ionophore with influx inhibitors bumetanide (B) (inhibitor of Na+, K+, 2Cl−-cotransport) and ouabain (O) (inhibitor of Na+, K+, ATPase pump) has been shown to induce an obvious K+ efflux in the two cell lines. These results are in accordance with the trends of other studies. Therefore, 1(a) was demonstrated to be a new candidate for the monitoring of intracellular potassium ion balance.

Example 23

Application of the K+ Sensing Films for Studying Antimicrobial Reagents

Figure 22:
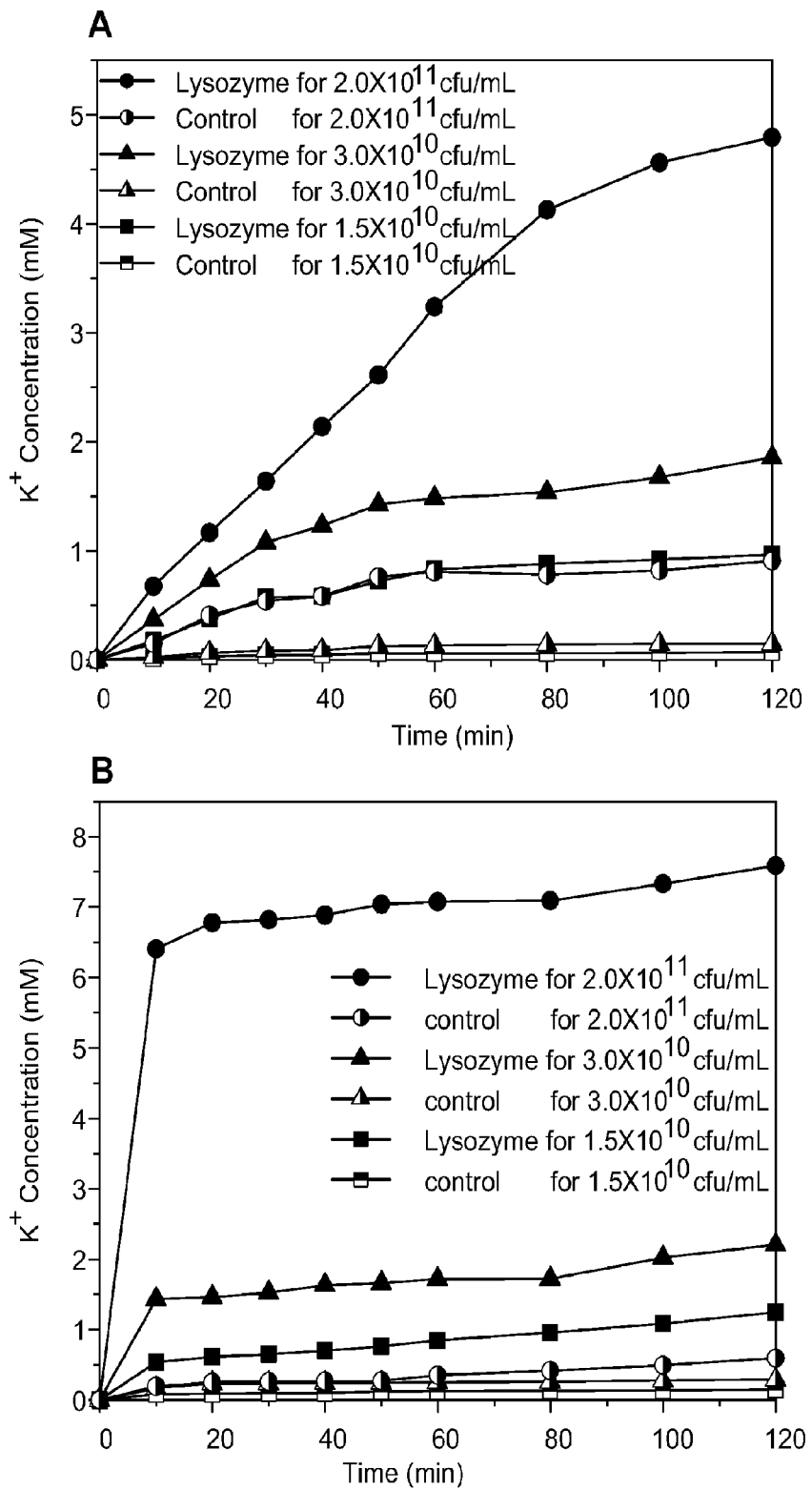
FIG. 22 show the effect of lysozyme on $K^+$-release from *E. coli* (22A) and *B. subtilis* (22B) visualized by F4 film.

F4 film was used for both gram positive (i.e. *B. subtilis*) and negative (i.e. *E. coli*) bacteria and lysozyme was used as a model drug to stimulate K+ efflux from the organisms. The bacteria were cultured at 37° C. overnight, centrifuged, and washed three times with potassium-free buffer with 150 mM NaCl at pH of 7.4. The washed organisms were resuspended in 2 mL of the potassium-free buffer in quartz cuvettes at a concentration range of $1.5 \times 10^{10}$ to $1.0 \times 10^{11}$ cfu/mL F4 was immersed into the above prepared mixtures, and then lysozyme was added into the cuvettes to stimulate the K+ efflux, which was monitored through the time dependent fluorescence intensity changes of F4 film. With the K+ releasing from the bacteria into the NaCl solution, the fluorescence intensity of F4 increases. FIG. 22 plots the time and bacterial concentration-dependent K+ concentration changes measured by using F4 film. For *E. coli*, K+ efflux increased slowly over time; while for *B. subtilis*, K+ efflux was very fast, within the first 10 minutes, and then very slow within the rest of time course. The difference between *E. coli* and *B. subtilis* is due to the antibacterial properties and action mode of lysozyme, which is more facile and faster in *B. subtilis* (gram-positive bacteria) compared to *E. coli* (gram-negative bacteria). The bactericidal properties of lysozyme are primarily ascribed to its N-acetylmuramoyl hydrolase enzymatic activity, resulting in peptidoglycan hydrolysis and cell lysis. Gram-negative bacteria are relatively insensitive to lysozyme by the virtue of their outer membrane that acts as a physical barrier preventing access of the enzyme.

A number of embodiments of the invention have been described. Nevertheless, it will be understood that various modifications may be made without departing from the spirit and scope of the invention. Accordingly, other embodiments are within the scope of the following claims.

What is claimed is:

1. A compound having the formula:

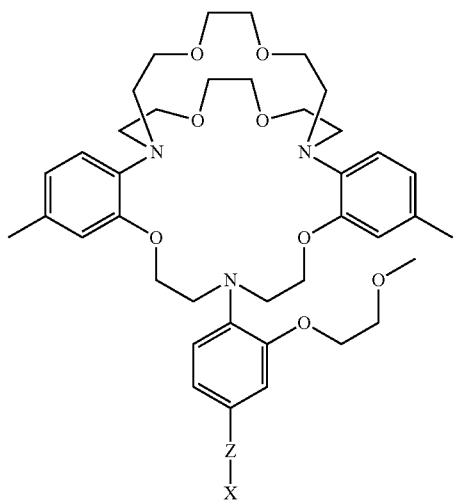

or a salt form thereof,
wherein:
Z is selected from the group consisting of:

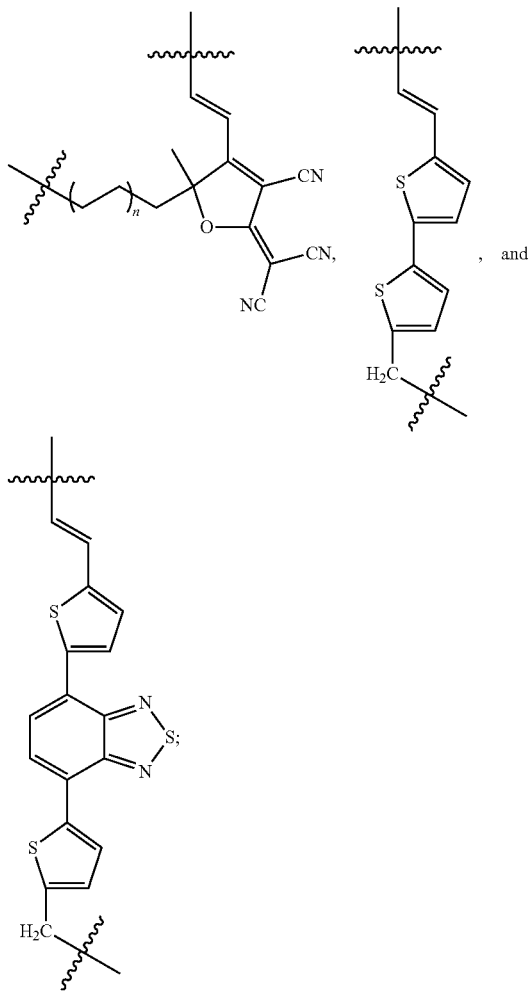

n is an integer from 0 to 3; and

X is selected from the group consisting of: H, OH,
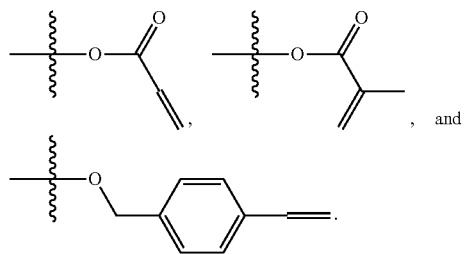, and
2. The compound of claim 1, wherein the compound is selected from the group consisting of:
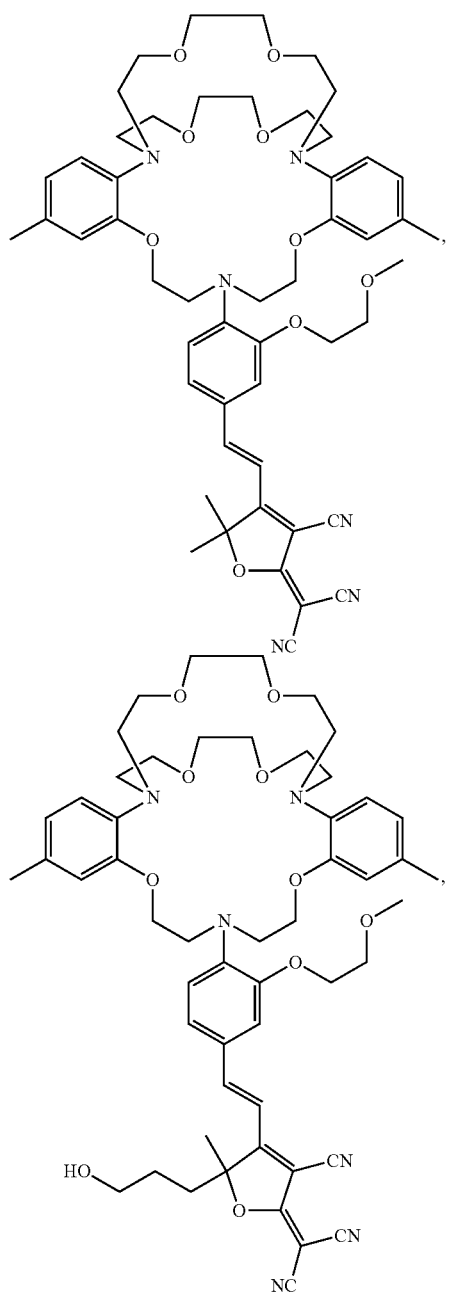
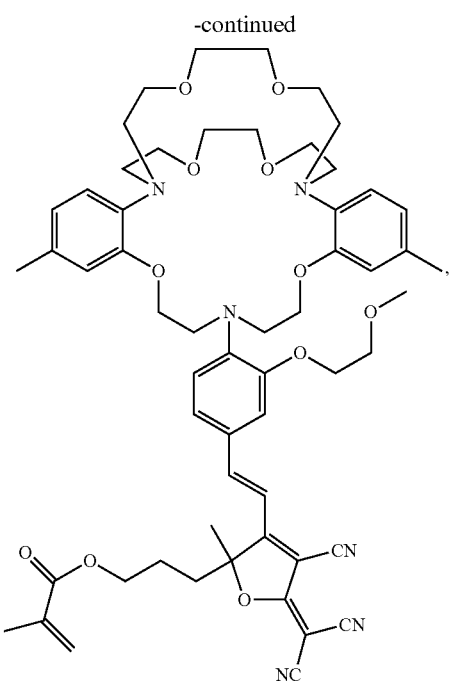
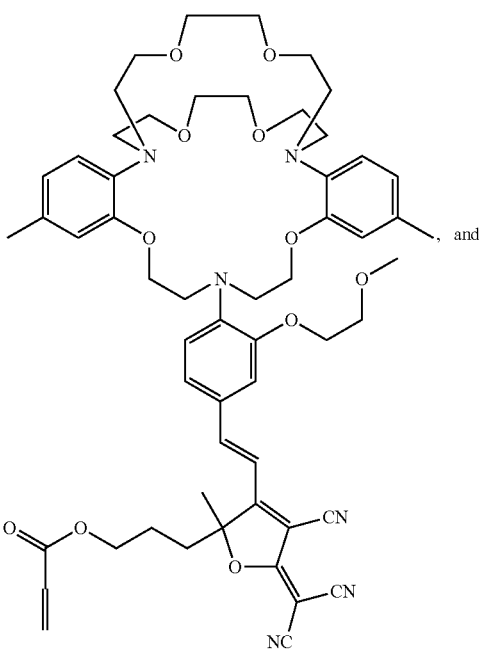

83
-continued
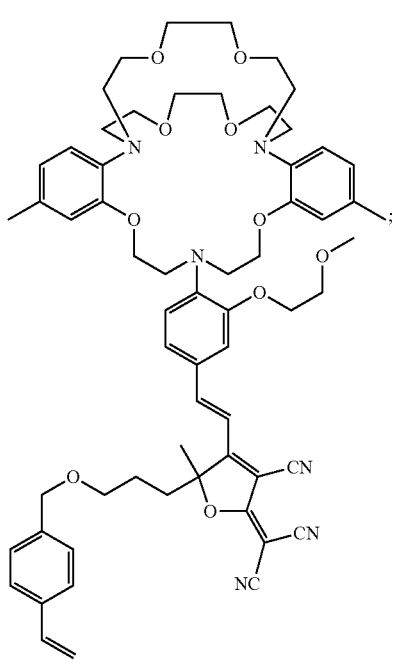
or a salt form thereof.
3. The compound of claim 1, wherein the compound is selected from the group consisting of:
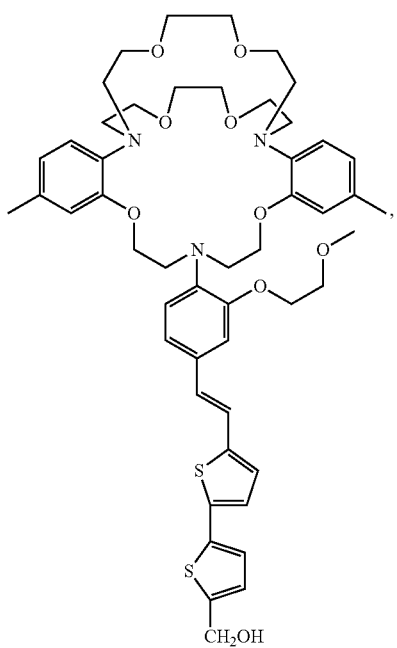
84
-continued
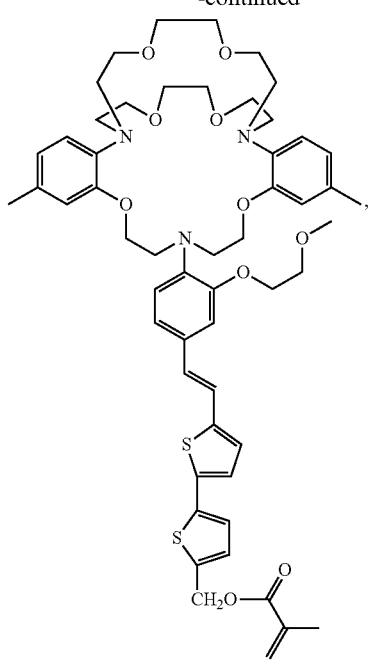
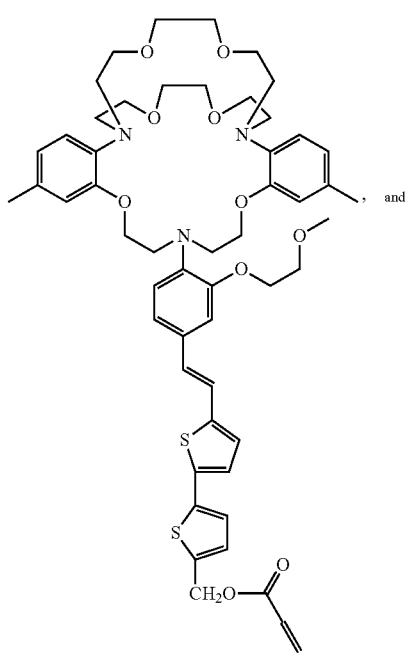, and 85
-continued
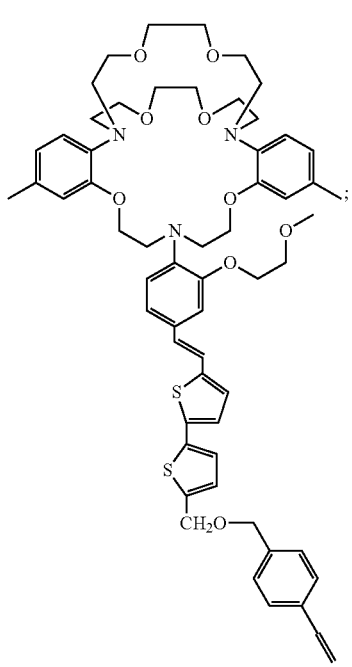
or a salt form thereof.
4. The compound of claim 1, wherein the compound is selected from the group consisting of
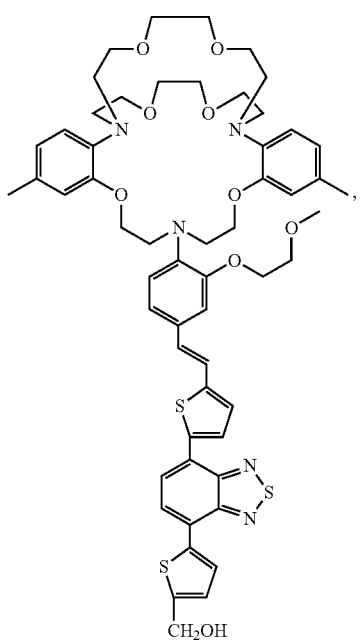
,
86
-continued
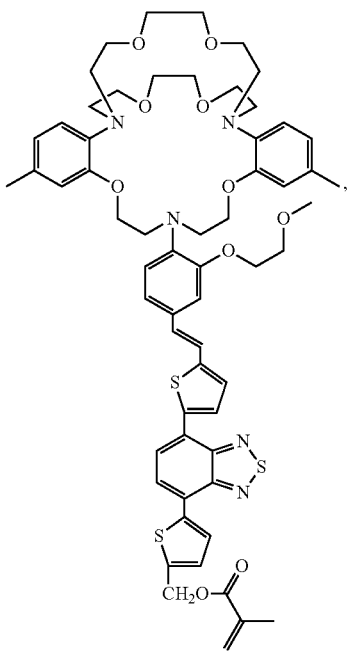
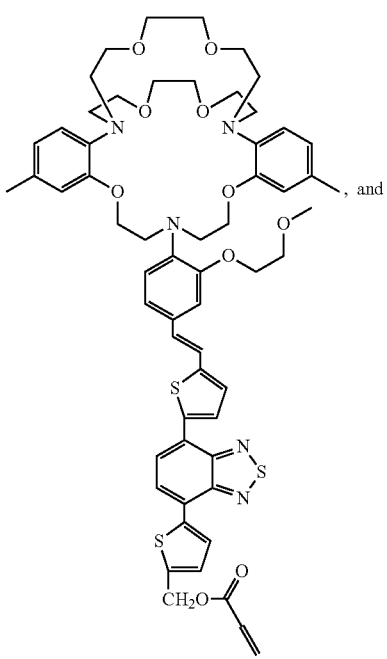
, and 87
-continued
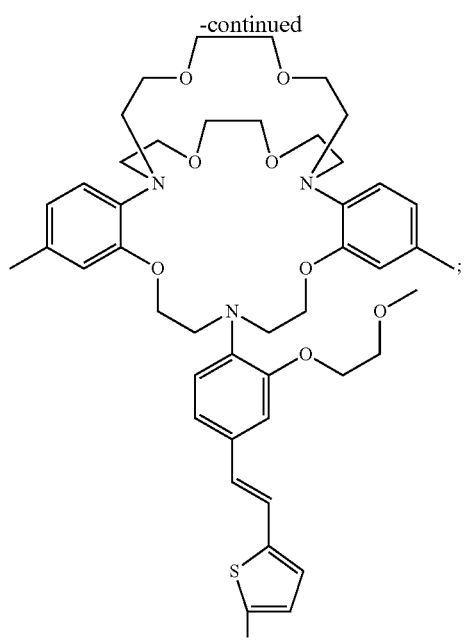
;
88
-continued
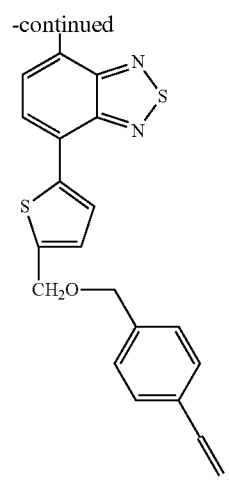
or a salt form thereof.
* * * * *